(12) United States Patent
Erion et al.

(10) Patent No.: US 6,752,981 B1
(45) Date of Patent: Jun. 22, 2004

(54) PRODRUGS FOR LIVER SPECIFIC DRUG DELIVERY

(75) Inventors: Mark D. Erion, Del Mar, CA (US); K. Raja Reddy, San Diego, CA (US)

(73) Assignee: Metabasis Therapeutics, Inc., San Diego, CA (US)

( * ) Notice: Subject to any disclaimer, the term of this patent is extended or adjusted under 35 U.S.C. 154(b) by 0 days.

(21) Appl. No.: 09/657,919

(22) Filed: Sep. 8, 2000

Related U.S. Application Data

(60) Provisional application No. 60/153,128, filed on Sep. 8, 1999.

(51) Int. Cl.[7] .................................................. A61K 49/00
(52) U.S. Cl. ........................ 424/9.1; 424/600; 424/1.11; 424/9.2; 424/1.65; 424/601; 514/7
(58) Field of Search .......................... 424/9.1, 600, 1.11, 424/9.2, 1.65, 601; 514/7, 33, 34, 35, 908

(56) References Cited

U.S. PATENT DOCUMENTS

| | | |
|---|---|---|
| 3,796,700 A | 3/1974 | Yoshioka et al. ......... 260/211.5 |
| 4,255,566 A | 3/1981 | Carrico et al. ................. 536/26 |
| 4,318,982 A | 3/1982 | Hornby et al. .................. 435/7 |
| 4,340,668 A | 7/1982 | Hornby et al. .................. 435/7 |
| 4,376,165 A | 3/1983 | Hornby et al. .................. 435/7 |
| 4,447,529 A | 5/1984 | Greenquist et al. ............. 435/7 |
| 6,312,662 B1 * | 11/2001 | Erion et al. ................... 424/9.1 |

FOREIGN PATENT DOCUMENTS

| | | |
|---|---|---|
| EP | 0 481 214 A | 4/1992 |
| WO | 98/39343 | 1/1994 |
| WO | 98/39342 | 3/1997 |
| WO | 98/39344 | 9/1998 |
| WO | 99/45016 A | 9/1999 |

OTHER PUBLICATIONS

Bedford, et al., "Synthesis of water–soluble prodrugs of the cytotoxic agent combretastatin A4," Bioorganic & Medicinal Chemistry Letters vol. 6(2): 157–160 (1996).
Bentrude, et al., "Stereo–and Regiochemistries of the Oxidations of 2–Methoxy–5–tert–butyl–1,3,2–dioxaphosphorinanes and the Cyclic Methyl 3', 5'–Phosphite of Thymidine by H2O/I2 and O2/AIBN to P–Chiral Phosphates. 170 NMR Assignment of Phosphorus Configuration to the Diastereomeric Thymidine Cyclic Methyl 3', 5'–Monophosphates," *J. Am. Chem. Soc.*, 111:3981–3987 (1989).
Farquhar, et al., "Synthesis and Biological Evaluation of Neutral Derivatives of 5–Fluoro–2'–deoxyuridine 5'–Phosphate," *J. Org. Chem.* 26:1153 (1983).
Farquhar, et al., "Biologically–Cleavable Phosphate Protective Groups: 4–Acyloxy–1,3,2–Dioxaphosphorinanes as Neutral Latent Precursors of Dianionic Phosphates," *Tetrahedron Lett.* 36:655 (1995).
Hayakawa, et al., "Benzimidazolium Triflate as an Efficient Promoter for Nucleotide Synthesis via the Phosphoramidite Mehtod," *J. Org. Chem.* 61:7996 (1996).
Meier, et al. "ADA–Bypass by lipophilic *Cyclo*–Sal–d–dAMP Pro–Nucleotides A second Example of the Efficiency of the *cyclo*Sat–Concept," *Bioorg, Med. Chem. Lett.* 7:1577 (1997)..
Nagamatsu, et al., "New Phosphorylating Agents for General Synthesis of Mixed Phosphate Esters," *Tetrahedron Lett.* 28:2375 (1987).
Nakayama, et al., "A Highly Enantioselective Synthesis of Phosphate Triesters," *J. Am. Chem. Soc.* 112:6936 (1990).
Ogg, et al., "A reporter gene assay to assess the molecular mechanisms of xenobiotic–dependent induction of the human CYP3A4 gene in vitro," *Xenobiotica* 29(3):269–279 (1999).
Shih, et al., "Studies on Potential Antitumor Agents (III). Synthesis of 4–Arylcyclophosphamides," *Heterocycles* 9 (9):1277–1285 (1978).
Wantanabe, et al., "Dibenzyl Phosphorofluoridate, A New Phosphorylating Agent," *Chem Pharm. Bull.* 38:562 (1990).
Yip, et al., "Use of High–Performance Liquid Chromatography in the Preparation of Flavin Adenine Dinucleotide Analyte Conjugates," *Journal of Chromatography* 326:301–310 (1985).

* cited by examiner

*Primary Examiner*—James O. Wilson
*Assistant Examiner*—Patrick Lewis
(74) *Attorney, Agent, or Firm*—Paul Hastings Janofsky & Walker

(57) ABSTRACT

The present invention is directed towards novel cyclic phosph(oramid)ate prodrugs of alcohol, amine-, and thiol-containing drugs, their preparation, their synthetic intermediates, and their uses. Another aspect of the invention is the use of the prodrugs to treat diseases that benefit from enhanced drug distribution to the liver and like tissues and cells that express cytochrome P450, including hepatitis, cancer, liver fibrosis, malaria, other viral and parasitic infections, and metabolic diseases where the liver responsible for the overproduction of the biochemical end product, e.g. glucose (diabetes); cholesterol, fatty acids and triglycerides (hyperlipidemia) (atherosclerosis) (obesity). In one apscet, the invention is directed towards the use of the prodrugs to enhance oral drug delivery. In another aspect, the prodrugs are used to prolong pharmacodynamic half-life of the drug. In addition, the prodrug methodology of the current invention is used to achieve sustained delivery of the parent drug. In another aspect, the prodrugs are used to increase the therapeutic index of the drug. In another aspect of the invention, a method of making these prodrugs is described. In another aspect, the prodrugs are also useful in the delivery of diagnostic imaging agents to the liver.

92 Claims, No Drawings

PRODRUGS FOR LIVER SPECIFIC DRUG DELIVERY

RELATED APPLICATIONS

This application claims benefit of U.S. Provisional Application No. 60/153,128 filed Sep. 8, 1999 and which is incorporated by reference herein in its entirely, including figures.

FIELD OF THE INVENTION

The present invention is directed towards novel prodrugs of alcohol, amine, and thiol-containing compounds, to their preparation, to their synthetic intermediates, and to their uses. Prodrugs of the invention may be used to deliver drugs to the liver with high tissue specificity.

BACKGROUND OF THE INVENTION

The following description of the background of the invention is provided to aid in understanding the invention, but is not admitted to be, or to describe, prior art to the invention. All cited publications are incorporated by reference in their entirety.

Drug induced toxicities and pharmacological side effects are often associated with interactions by the drug or drug metabolite in tissues not associated with the pharmacological benefits of the drug therapy. In other cases, the desired pharmacological effect is poorly achieved either because of dose-limiting toxicities or inadequate drug levels in the target tissues. Thus, there is a need to deliver drugs to specific tissues or organs. High organ specificity can be achieved by a variety of mechanisms including local administration to the target organ and drug-protein conjugates. Local administration to the target organ is an invasive procedure. Drug-protein conjugates exhibit poor oral bioavailability, limitations in carrier manufacturing and drug loading, a potential for diminished liver uptake due to down regulation of the receptor in diseased tissue, and a high incidence of antibody induction. A third approach entails use of prodrugs that are activated by enzymes highly enriched in the target organ.

There is particularly a need to deliver drugs to the liver to treat diseases such as hepatitis, cancer, malaria, and fibrosis which are poorly treated with current therapies. Many therapies for these conditions have narrow therapeutic indices. Other diseases such as hyperlipidemia where the liver is responsible for the overproduction of biochemical endproducts that directly contribute to the pathogenesis of disease can also be treated with liver specific drug delivery. Thus, there is still a need for prodrugs to enhance specificity.

SUMMARY OF THE INVENTION

The present invention is directed towards novel cyclic phosph(oramid)ate prodrugs of alcohol-, amine-, and thiol-containing drugs, their preparation, their synthetic intermediates, and their uses. Another aspect of the invention is the use of the prodrugs to treat diseases that benefit from enhanced drug distribution to the liver and like tissues and cells that express cytochrome P450, including hepatitis, cancer, liver fibrosis, malaria, other viral and parasitic infections, and metabolic diseases where the liver is responsible for the overproduction of the biochemical end product, e.g. glucose (diabetes); cholesterol, fatty acids and triglycerides (hyperlipidemia) (atherosclerosis) (obesity). In one aspect, the invention is directed towards the use of the prodrugs to enhance oral drug delivery. In another aspect, the prodrugs are used to prolong pharmacodynamic half-life of the drug. In addition, the prodrug methodology of the current invention is used to achieve sustained delivery of the parent drug. In another aspect, the prodrugs are used to increase the therapeutic index of the drug. In another aspect of the invention, a method of making these prodrugs is described. In another aspect, the prodrugs are also useful in the delivery of diagnostic imaging agents to the liver.

One aspect of the present invention concerns prodrugs of formula I

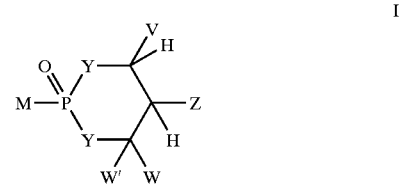

wherein:

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 additional carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S) OR³, —CHR²OC(O)SR³, —CHR²OCO₂R³, —OR², —SR², —CHR²N₃, —CH₂aryl, —CH(aryl)OH, —CH (CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)ₚ—OR¹², and —(CH₂)ₚ—SR¹²;

p is an integer 2 or 3;

with the provisos that:

a) V, Z, W, W' are not all —H; and b) when Z is —R²OR², then at least one of V, W, and W' is not —H, alkyl, aralkyl, or alicyclic;

c) when Z is CHR²OH, then M is not —NH(lower alkyl), —N(lower alkyl)₂, —NH(lower alkylhalide), —N(lower alkylhalide)$_2$ or —N(lower alkyl)(lower alkylhalide); and d) when V is aryl or substituted aryl, then M is not —O(D) where D is hydrogen, a metal ion or an ammonium ion;

$R^2$ is selected from the group consisting of $R^3$ and —H;

$R^3$ is selected from the group consisting of alkyl, aryl, alicyclic, and aralkyl;

$R^6$ is selected from the group consisting of —H, lower alkyl, acyloxyalkyl, alkoxycarbonyloxyalkyl, and lower acyl;

$R^{12}$ is selected from the group consisting of —H, and lower acyl;

each Y is independently selected from the group consisting of —O—, and —NR$^6$—;

M is selected from the group consisting of drugs MH containing an —OH, —NHR$^2$, or —SH group, and that is attached to the phosphorus in formula I via O, N, or S of said OH, —NHR$^2$, or SH group;

and pharmaceutically acceptable prodrugs and salts thereof.

Since these compounds have asymmetric centers, the present invention is directed not only to racemic and diastereomeric mixtures of these compounds, but also to individual stereoisomers. The present invention also includes pharmaceutically acceptable and/or useful salts of the compounds of formula I, including acid addition salts. The present inventions also encompass prodrugs of compounds of formula I.

Definitions

In accordance with the present invention and as used herein, the following terms are defined with the following meanings, unless explicitly stated otherwise.

The term "aryl" refers to aromatic groups which have 5–14 ring atoms and at least one ring having a conjugated pi electron system and includes carbocyclic aryl, heterocyclic aryl and biaryl groups, all of which may be optionally substituted. Suitable aryl groups include phenyl and furanyl.

Carbocyclic aryl groups are groups, wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted including bicyclic aromatics, e.g. benzimidazole.

The term "biaryl" refers to aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. "Substituted aryl" and "substituted heteroaryl" preferably refers to aryl and heteroaryl groups substituted with 1–3 substituents. Preferably these substituents are selected from the group consisting of lower alkyl, lower alkoxy, lower perhaloalkyl, halo, hydroxy, and amino.

The term "aralkyl" refers to an alkylene group substituted with an aryl group. Suitable aralkyl groups include benzyl, picolyl, and the like, and may be optionally substituted. "Heteroarylalkyl" refers to an alkylene group substituted with a heteroaryl group.

The term "alkylaryl" refers to an aryl group substituted with an alkyl group. "Lower alkylaryl" refers to such groups where alkyl is lower alkyl.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl or aryl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and $R^1$ can form a cyclic ring system.

The term "-carboxylamido" refers to —CONR$_2$ where each R is independently hydrogen or alkyl.

The term "halogen" or "halo" refers to —F, —Cl, —Br and —I.

The term "alkylaminoalkylcarboxy" refers to the group alkyl-NR-alk-C(O)—O— where "alk" is an alkylene group, and R is a H or lower alkyl.

The term "alkyl" refers to saturated aliphatic groups including straight-chain, branched chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic of 3 to 10 atoms, more preferably 3 to 6 atoms. Suitable cyclic groups include norbornyl and cyclopropyl. Such groups may be substituted.

The term "heterocyclic" and "heterocyclic alkyl" refer to cyclic groups of 3 to 10 atoms, more preferably 3 to 6 atoms, containing at least one heteroatom, preferably 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The term "phosphono" refers to —PO$_3$R$_2$, where R is selected from the group consisting of —H, alkyl, aryl, aralkyl, and alicyclic.

The term "sulphonyl" or "sulfonyl" refers to —SO$_3$R, where R is H, alkyl, aryl, aralkyl, and alicyclic.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a W substituent attached to the cyclic phosph(oramid)ate, it is attached at the first carbon.

The term "alkynyl" refers to unsaturated groups which contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g. it is a W substituent attached to the cyclic phosph (oramid)ate, it is attached at the first carbon.

The term "alkylene" refers to a divalent straight chain, branched chain or cyclic saturated aliphatic group.

The term "acyloxy" refers to the ester group —O—C(O)R, where R is H, alkyl, alkenyl, alkynyl, aryl, aralkyl, or alicyclic.

The term "aminoalkyl-" refers to the group NR$_2$-alk- wherein "alk" is an alkylene group and R is selected from H, alkyl, aryl, aralkyl, and alicyclic.

The term "alkylaminoalkyl-" refers to the group alkyl-NR-alk- wherein each "alk" is an independently selected alkylene, and R is H or lower alkyl. "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, aralkyl, and alicyclic. In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, and alicyclic. In "lower alkylaminoaryl-", the alkylene group is lower alkyl.

The term "alkoxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy" or "alkyloxy-" refers to the group alkyl-O—.

The term "alkoxyalkyl-" or "alkyloxyalkyl-" refer to the group alkyl-O-alk- wherein "alk" is an alkylene group. In "lower alkoxyalkyl-", each alkyl and alkylene is lower alkylene.

The terms "alkylthio" and "alkylthio-" refer to the groups alkyl-S—.

The term "alkylthioalkyl-" refers to the group alkyl-S-alk- wherein "alk" is an alkylene group. In "lower alkylthioalkyl-" each alkyl and alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The terms "amido" or "carboxamido" refer to NR$_2$—C(O)— and RC(O)—NR$^1$—, where R and R$^1$ include H, alkyl, aryl, aralkyl, and alicyclic. The term does not include urea, —NR—C(O)—NR—.

The term "carboxamidoalkylaryl" and "carboxamidoaryl" refers to an aryl-alk-NR$^1$—C(O), and ar-NR$^1$—C(O)-alk-, respectively where "ar" is aryl, "alk" is alkylene, R$^1$ and R include H, alkyl, aryl, aralkyl, and alicyclic.

The term "hydroxyalkyl" refers to an alkyl group substituted with one —OH.

The term "haloalkyl" refers to an alkyl group substituted with one halo.

The term "cyano" refers to —C≡N.

The term "nitro" refers to —NO$_2$.

The term "acylalkyl" refers to an alkyl-C(O)-alk-, where "alk" is alkylene.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "guanidino" refers to both —NR—C(NR)—NR$_2$ as well as —N=C(NR$_2$)$_2$ where each R group is independently selected from the group of —H, alkyl, alkenyl, alkynyl, aryl, and alicyclic, all except —H are optionally substituted.

The tern "amidino" refers to —C(NR)—NR$_2$ where each R group is independently selected from the group of —H, alkyl, alkenyl, alkynyl, aryl, and alicyclic, all except —H are optionally substituted.

The term "pharmaceutically acceptable salt" includes salts of compounds of formula I and its prodrugs derived from the combination of a compound of this invention and an organic or inorganic acid or base. Suitable acids include HCl.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, R$_2$N—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of formula I, fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, for example, anticancer agents, antiviral agents, and antibiotic agents.

The term "bidentate" refers to an alkyl group that is attached by its terminal ends to the same atom to form a cyclic group. For example, propyleneamine contains a bidentate propylene group.

The structure

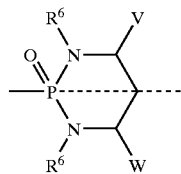

has a plane of symmetry running through the phosphorus-oxygen double bond when $R^6$=$R^6$, V=W, W'=H, and V and W are either both pointing up or both pointing down. The same is true of structures where each —$NR^6$— is replaced with —O—.

The term "cyclic 1',3'-propane ester", "cyclic 1,3-propane ester", "cyclic 1',3'-propanyl ester", and "cyclic 1,3-propanyl ester" refers to the following:

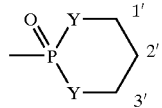

The phrase "together V and Z are connected via an additional 3–5 atoms to form a cyclic group containing 5–7 atoms, optionally containing 1 heteroatom, substituted with hydroxy, acyloxy, alkoxycarbonyloxy, or aryloxycarbonyloxy attached to a carbon atom that is three atoms from both Y groups attached to the phosphorus" includes the following:

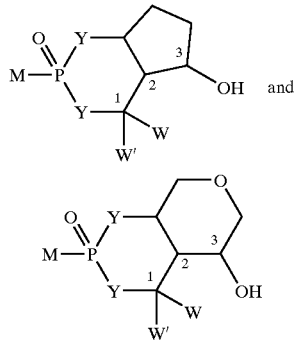

The structure shown above (left) has an additional 3 carbon atoms that forms a five member cyclic group. Such cyclic groups must possess the listed substitution to be oxidized.

The phrase "together V and Z are connected via an additional 3–5 atoms to form a cyclic group, optionally containing one heteroatom, said acyclic group is fused to an aryl group attached at the beta and gamma position to the Y adjacent to the phosphorus" includes the following:

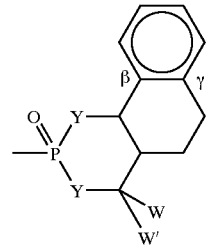

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

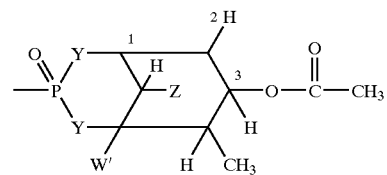

The structure above has an acyloxy substituent that is three carbon atoms from a Y, and an optional substituent, —$CH_3$, on the new 6-membered ring. There has to be at least one hydrogen at each of the following positions: the carbon attached to Z; both carbons alpha to the carbon labeled "3"; and the carbon attached to "OC(O)$CH_3$" above.

The phrase "together W and W' are connected via an additional 2–5 atoms to form a cyclic group, optionally containing 0–2 heteroatoms, and V must be aryl, substituted aryl, heteroaryl, or substituted heteroaryl" includes the following:

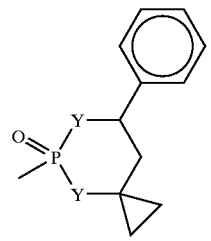

The structure above has V=aryl, and a spiro-fused cyclopropyl group for W and W'.

The term "phosph(oramid)ite" refers to phosphites, thiophosphites, and phosphoramidites which are compounds attached via O, S, or N, respectively, to the phosphorus in —P(YR)(YR) including cyclic forms, where Y is independently —O— or —$NR^6$—.

The term "phosph(oramid)ate" refers to phosphates, thiophosphates, and phosphoramidates which are compounds attached via O, S, or N, respectively, to the phosphorus in —P(O)(YR)(YR), including cyclic forms, where Y is independently —O— or —$NR^6$—.

The term "cyclic phosph(oramid)ate" refers to

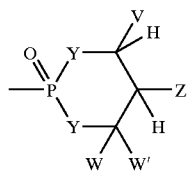

The carbon attached to V must have a C—H bond. The carbon attached to Z must also have a C—H bond.

The term "liver" refers to liver and to like tissues and cells that contain the CYP3A4 isozyme or any other P450 isozyme found to oxidize the phosph(oramid)ate esters of the invention. Based on Example F, we have found that prodrugs of formula VI and VIII are selectively oxidized by the cytochrome P450 isoenzyme CYP3A4. According to DeWaziers et al. (*J. Pharm. Exp. Ther.*, 253, 387–394 (1990)), CYP3A4 is located in humans in the following tissues (determined by immunoblotting and enzyme measurements):

| Tissues | % of liver activity |
| --- | --- |
| Liver | 100 |
| Duodenum | 50 |
| jejunum | 30 |
| ileum | 10 |
| colon | <5 (only P450 isoenzyme found) |
| stomach | <5 |
| esophagus | <5 |
| kidney | not detectable |

Thus, "liver" more preferably refers to the liver, duodenum, jejunum, ileum, colon, stomach, and esophagus. Most preferably, liver refers to the liver organ.

The term "enhancing" refers to increasing or improving a specific property.

The term "liver specificity" refers to the ratio:

$$\frac{[\text{drug or a drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC based on values measured at three or more time points.

The term "increased or enhanced liver specificity" refers to an increase in the liver specificity ratio in animals treated with the prodrug relative to animals treated with the parent drug.

The term "enhanced oral bioavailability" refers to an increase of at least 50% of the absorption of the dose of the parent drug or prodrug(not of this invention) from the gastrointestinal tract. More preferably it is at least 100%. Measurement of oral bioavailability usually refers to measurements of the prodrug, drug, or drug metabolite in blood, tissues, or urine following oral administration compared to measurements following systemic administration.

The term "parent drug" refers to any compound which delivers the same biologically active compound. The parent drug form is MH and standard prodrugs of MH, such as esters.

The term "drug metabolite" refers to any compound produced in vivo or in vitro from the parent drug, which can include the biologically active drug.

The term "pharmacodynamic half-life" refers to the time after administration of the drug or prodrug to observe a diminution of one half of the measured pharmacological response. Pharmacodynamic half-life is enhanced when the half-life is increased by preferably at least 50%.

The term "pharmacokinetic half-life" refers to the time after administration of the drug or prodrug to observe a diminution of one half of the drug concentration in plasma or tissues.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The term "bypassing drug resistance" refers to the loss or partial loss of therapeutic effectiveness of a drug (drug resistance) due to changes in the biochemical pathways and cellular activities important for producing and maintaining the biologically active form of the drug at the desired site in the body and to the ability of an agent to bypass this resistance through the use of alternative pathways and cellular activities.

The term "biologically active drug or agent" refers to the chemical entity that produces a biological effect. Thus, active drugs or agents include compounds which as MH are biologically active.

The term "therapeutically effective amount" refers to an amount that has any beneficial effect in treating a disease or condition.

DETAILED DESCRIPTION OF THE INVENTION

The invention is directed to the use of new cyclic 1,3-propanyl phosph(oramid)ate esters which are converted to phosphate, phosphoramidate, or thiophosphate containing compounds by P450 enzymes found in large amounts in the liver and other tissues containing these specific enzymes. The phosphates, phosphoramidates and thiophosphates are then hydrolized (by alkaline phosphatase, for example) to produce the free hydroxy, amine, or thiol, respectively. This methodology can be applied to various drugs and to diagnostic imaging agents which contain —OH, —NHR$^2$, or —SH functionality. In effect, this methodology provides a prodrug (cyclic 1,3-propanyl phosph(oramid)ate esters) of a prodrug (phosphate, phosphoramidate, or thiophosphate) of a drug (contains —OH, —NHR$^2$ or —SH).

In another aspect of the invention, this prodrug methodology can also be used to prolong the pharmacodynamic half-life because the cyclic phosph(oramid)ates of the invention can prevent the action of enzymes which degrade the parent drug.

In another aspect of the invention, this prodrug methodology can be used to achieve sustained delivery of the parent drug because oxidation of the prodrugs depends on the substituents V, Z, W, and W'. Prodrugs found to oxidize slowly but provide therapeutic drug levels, therefore result in sustained drug delivery.

The novel cyclic 1,3-propanylester methodology of the present invention may also be used to increase the distribution of a particular drug or imaging agent to the liver which contains abundant amounts of the P450 isozymes capable of oxidizing the cylic 1,3-propanylester of the present invention so that the free phosph(oramid)ate is produced. The phosph(oramid)ate is then dephosphorylated by alkaline phosphatase, for example, in the target tissue to produce the active drug. Accordingly, this prodrug technology should prove useful in the treatment of liver diseases or diseases where the liver is responsible for the overproduction of the biochemical end product such as glucose, cholesterol, fatty acids and triglycerides. Such diseases include viral and parasitic infections, liver cancer, liver fibrosis, diabetes, hyperlipidemia, and obesity. Such anti-diabetic agents do not include FBPase inhibitors.

In addition; the liver specificity of the prodrugs should also prove useful in the delivery of diagnostic agents to the liver. The prodrugs of the present invention may be used to help identify diseases of the liver. For example, a person with a normal liver receiving a prodrug of an imaging agent would show the parent compound in the whole liver. A patient with a non-P450 expressing metastasis would show an area that does not contain the imaging agent.

These specific P450 enzymes are also found in other specific tissues and cells, and thus this methodology may also be used to increase the delivery of these agents to those tissues. In particular, certain cancers express P450. For instance, many cancers of the colon, soft tissue carcinoma, and metastases of hepatomas express P450 enzymes including CYP3A4. Such cancers even when outside the liver can be treated using the present invention.

In another aspect of the invention, the characteristic that most of the cyclic phosph(oramid)ates of the present invention are metabolized in the liver to produce the drug containing hydroxy, amine, or thiol, can enable the use of the prodrug methodology of the present invention to increase the therapeutic index of various drugs which tend to have side effects related to the amount of the drug or its metabolites which are distributed in extrahepatic tissues.

In another aspect of the invention, the cyclic phosph (oramid)ate prodrugs can increase the oral bioavailability of the drugs.

These aspects are described in greater detail below.

Prodrug Cleavage Mechanism

The prodrugs of the current invention are simple, low molecular weight modifications of the drug which enable liver-selective drug delivery on the basis of the their sensitivity to liver-abundant enzymes. The prodrug cleavage mechanism is supported through studies such as that shown in Examples A, E, F, and H. Prodrugs of the invention exhibit good stability in aqueous solutions across a broad pH range and therefore do not undergo a chemical cleavage process to produce the parent drug or free phosph(oramid) ate of the parent drug. (Example O). In addition the prodrugs exhibit good stability in plasma and in the presence of alkaline phosphatase. (Example P). In contrast to the parent drug, the prodrugs are rapidly cleaved in the presence of liver microsomes from rats (Example F) and humans (Example E). The drug is also produced in freshly isolated rat hepatocytes where it is detected as the parent drug (Example A). The by-product of the cleavage reaction was identified to further confirm the cleavage mechanism. (Example H).

Possible specific enzymes involved in the cleavage process were evaluated through the use of known cytochrome P450 inhibitors (Example F). The studies indicate that the isoenzyme cytochrome CYP3A4 is responsible for the oxidation based on ketoconazole inhibition of drug formation. Inhibitors of cytochrome P450 family 1 and/or family 2 do not inhibit prodrug cleavage.

Parent drug M, is also detected in the liver following administration of drugs of formulae VI–VIII, shown below:

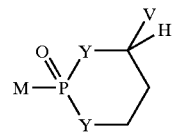

VI

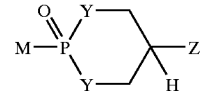

VII

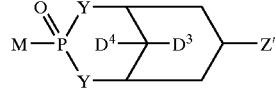

VIII

Prodrugs of formulae VI, VII, and VIII are particularly preferred.

Analysis of the by-products indicates that prodrugs of formula VI generate arylvinyl ketones (Example H), whereas prodrugs of formula VIII generate phenol. The mechanism of cleavage could proceed by the following mechanisms.

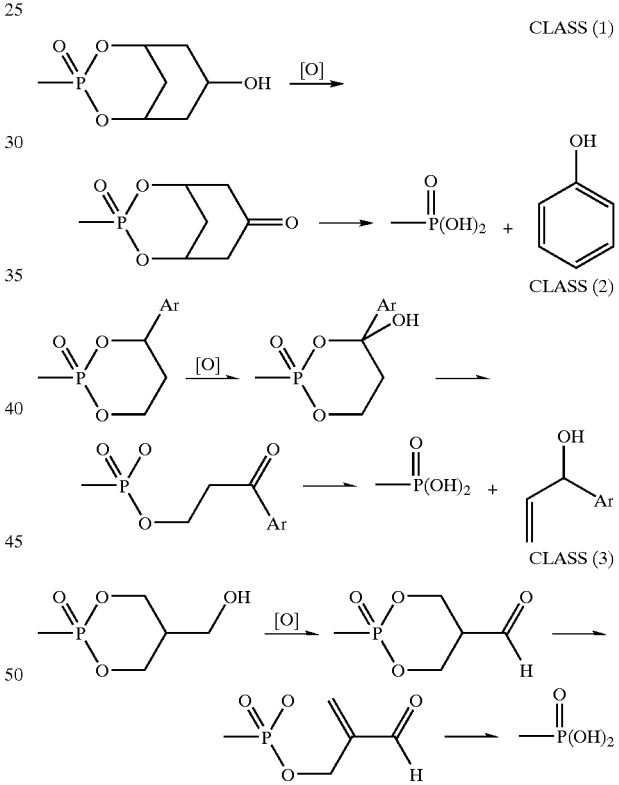

Although the esters in the invention are not limited by the above mechanisms, in general, each ester contains a group or atom susceptible to microsomal oxidation (e.g. alcohol, benzylic methine proton), which in turn generates an intermediate that breaks down to the parent compound in aqueous solution via β-elimination of the phosph(oramid)ate.

Furthermore, although these specific prodrugs are cleaved by CYP3A4, other pro drugs in the class may be substrates for other P450s. Small changes in structure are known to influence substrate activity and P450 preference.

In one aspect, the invention is directed to compounds that are prodrugs of formula I

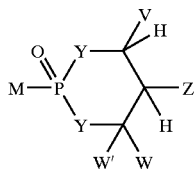

wherein

V is selected from the group consisting of aryl, substituted aryl, heteroaryl, and substituted heteroaryl. This class of prodrugs, shown above as class (2), readily undergo P450 oxidation at the benzylic methine proton (the proton on the carbon to which V is attached). In fact, there must be a hydrogen geminal to V to undergo this oxidation mechanism. Because Z, W, and W' are not at the oxidation site in this class of prodrugs, a broad range of substituents are possible. In one aspect, it is preferred if Z is an electron donating group which will reduce the mutagenicity or toxicity of the arylvinyl ketone that is the by-product of the oxidation of this class of prodrug. Thus, in this aspect Z is —$OR^2$, —$SR^2$, or —$NR^2{}_2$.

In another aspect of prodrugs where V is aromatic, it is more preferred when Z is —$R^2$, —$OR^2$, —$SR^2$, or —$NR^2{}_2$, —$OCOR^3$, —$OCO_2R^3$, —$SCOR^3$, $SCO_2R^3$, —$NHCOR^2$, —$NHCO_2R^3$, —$(CH_2)_p$—$OR^{12}$, and —$(CH_2)_p$—$SR^{12}$. Particularly preferred are such compounds where Z is not —$OR^2$, —$SR^2$, or —$NR^2{}_2$. Especially preferred is when Z is H.

In this class of prodrug, it is more preferred when W' and W are independently selected from the group consisting of —H, alkyl, aryl, substituted aryl, heteroaryl, and substituted heteroaryl. In one aspect, it is preferred when W' is H, and W and V are the same, and V and W are cis to one another. In another aspect, it is preferred when W' is H and W and V are the same, and V and W are trans to one another. More preferred, is when V, W, and W' are H, as this provides the similiest type of prodrug.

In another aspect, the invention is directed to compounds that are prodrugs of formula I

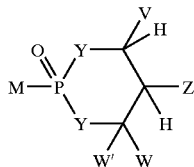

wherein together V and Z are connected via an additional 3–5 atoms to form a cyclic group, optionally containing 1 heteroatom, said cyclic group is fused to an aryl group at the beta and gamma position to the Y adjacent to V. This class of prodrugs is susceptible to P450 oxidation and oxidizes by a mechanism analogous to those of class (2) shown above where V is aromatic. The same W and W' groups as described above for class (2) prodrugs are suitable.

In another aspect, the invention is directed to compounds that are prodrugs of formula I

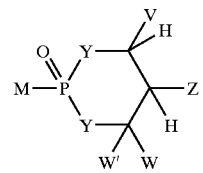

wherein Z is selected from the group consisting of of —$HR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$SR^2$, —$CHR^2N_3$, —$CH_2aryl$, —$CH(aryl)OH$, —$CH(CH=CR^2{}_2)OH$, —$CH(C\equiv CR^2)OH$, and —$CH_2NHaryl$. This class of prodrugs; shown above as class (3), readily undergo P450 oxidation because they have a hydroxyl or hydroxyl equivalent (e.g., —$CHR^2OC(O)R^3$, —$CHR^2N_3$) with an adjacent (geminal) acidic proton. Z groups may also readily undergo P450 oxidation because they have a benzylic methine proton or equivalent (e.g., —$CH_2aryl$, —$CH(CH=CR^2{}_2)OH$). Where Z is —$SR^2$, it is believed that this is oxidized to the sulfoxide or sulfone which will enhance the beta-elimination step. Where Z is —$CH_2NHaryl$, the carbon next to nitrogen is oxidized to produce a hemiaminal, which hydrolizes to the aldehyde (—C(O)H), as shown above for class (3).

Because V, W, and W' are not at the oxidation site in this class of prodrugs, a broad range of V, W, and W' substituents is possible. One preferred aspect has V, W', and W substituted such that there is a line of symmetry though the phosphorus-oxygen double bond. More preferred is when V, W', and W are H.

In another aspect, the invention is directed to compounds that are prodrugs of formula I

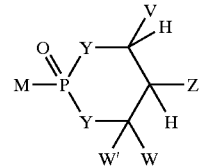

wherein together V and Z are connected via an additional 3–5 atoms to form a cylic group containing 5–7 atoms, optionally 1 heteroatom, substituted with hydroxy, acyloxy, alkoxycarbonyloxy, or aryloxycarbonyloxy attached to a carbon that is three atoms from both Y groups attached to the phosphorus. This class of prodrugs undergoes P450 oxidation and oxidizes by a mechanism analogous to those of class (3) described above. The broad range of W' and W groups are suitable. Most preferred is H.

In another aspect, the invention is directed to compounds that are prodrugs of formula VIII

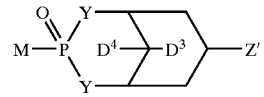

wherein Z' is —OH, —$OC(O)R^3$, —$OCO_2R^3$, or $OC(O)SR^3$. This class of prodrugs, shown above as class (1), readily undergoes P450 oxidation because they have a hydroxyl or hydroxyl equivalent group with an adjacent (geminal) acidic proton.

Because $D^3$ and $D^4$ are not at the oxidation site, a broad range of $D^3$ and $D^4$ substituents are possible, as long as one of $D^3$ and $D^4$ is H. This enables the ultimate elimination that produces phenol.

Alternatively, cyclic phosphoramidates can serve as a prodrug since intermediate phosphoramidates can generate the intermediate phosph(oramid)ate by a similar mechanism. The phosph(oramid)ate $(MP(O)(NH_2)O^-)$ is then converted to the drug MH either directly or via the phosph(oramid)ate $(M-PO_3^{2-})$.

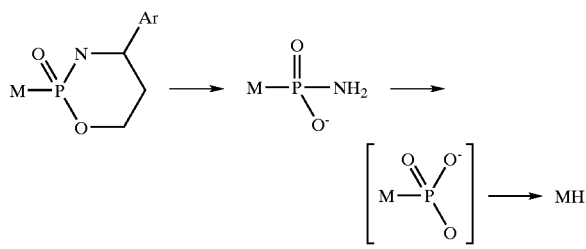

Enhanced Selective Delivery of Agents to the Liver and Like Tissues

Delivery of a drug to the liver with high selectivity is desirable in order to treat liver diseases or diseases associated with the abnormal liver properties (e.g. diabetes, hyperlipidemia) with minimal side effects.

Analysis of the tissue distribution of CYP3A4 indicates that it is largely expressed in the liver (DeWaziers et al., *J. Pharm. Exp. Ther.* 253: 387 (1990)). Moreover, analysis of tissue homogenates in the presence of prodrugs indicates that only the liver homogenate cleaves the prodrug. Kidney, brain, heart, stomach, spleen, muscle, lung, and testes showed no appreciable cleavage of the prodrug (Example D).

Evidence of the liver specificity can also be shown in vivo after both oral and i.v. administration of the prodrugs as described in Example E. Administration of the etoposide prodrug, Compound 1.1, is expected to result in enhanced liver specificity relative to free etoposide.

The prodrugs described in this invention can be tailored such that the elimination step is fast and therefore the product is produced near the site of oxidation, which for these prodrugs is in the liver or other P450-expressing tissue/cells.

In some cases liver specificity will be achieved most optimally using prodrugs of highly reactive drugs, which after production, act locally at a fast rate relative to diffusion out of the liver.

Increased Therapeutic Index

The prodrugs of this invention can significantly increase the therapeutic index ("TI") of certain drugs. In many cases, the increased TI is a result of the high liver specificity.

The prodrugs described in this invention can be tailored such that the elimination step is fast and therefore confines production of the phosph(oramid)ate to the liver. Prodrugs of formula VI–VII do not readily recyclize, since the carbonyl product is a ketone except when $Z=CH_2OH$ in formula VII. Ketones do not hydrate to a great extent (<2%), nor do they necessarily undergo the same metabolism associated with the aldehyde.

Severe toxicities are associated with nearly all anticancer agents. Most of these toxicities are associated with extrahepatic drug exposure. In an effort to decrease these toxicities during treatment of primary or secondary liver cancers, drugs are sometimes administered directly into the hepatic artery (e.g. floxuridine, mitomycin, etoposide). The high liver specificity of the prodrugs in the current invention suggest that systemic side effects will be minimized by the novel prodrug approach.

Moreover, primary and secondary liver cancers are particularly resistant to both chemotherapy and radiotherapy. Although the mechanism for the resistance is not completely understood, it may arise from increased liver gene products that lead to rapid metabolism and/or export of chemotherapeutic agents. In addition, the liver, which is generally associated with xenobiotic metabolism and generation of cytotoxic intermediates, is equipped by nature with multiple protective mechanism so that damage from these intermediates are minimized. For example, the intracellular concentration of glutathione is very high in the liver relative to other tissues presumably so that intermediates capable of alkylating proteins and DNA are detoxified through a rapid intracellular reaction. Consequently, the liver may be resistant to chemotherapeutic agents because of these mechanisms and therefore require higher than normal concentrations of the oncolytic agent to achieve success. Higher liver concentrations require higher doses of the drug which commonly result in extrahepatic toxicities.

To circumvent these limitations, drugs are sometimes administered directly into the hepatic artery (e.g. floxuridine, mitomycin, etoposide). Increased response rates are observed with this route of administration presumably because higher liver drug levels are achieved without an increase in the severity of the drug associated toxicities.

Prodrugs of the current invention achieve similar improvement in the response rate relative to extra-hepatic toxicities. This improvement in the therapeutic index provides an alternative strategy for the treatment of liver diseases, e.g. primary and secondary liver cancers.

The high liver specificity of prodrug cleavage implies that the by-product of prodrug cleavage is also primarily produced in the liver. Accordingly, toxicities associated with the by-product are minimized since the by-product frequently undergoes rapid detoxification reactions that either eliminate or minimize by-product toxicity. For example, reactions between the by-product and compounds and/or proteins present in the hepatocytes (e.g. glutathione and the α,β-unsaturated olefin generated by prodrugs of formulae VI and VII). Moreover, enzymes present in the liver may also further transform the by-product into a non-toxic compound (e.g. oxidation and/or sulfation of phenol, or reduction of the α,β-unsaturated ketone, etc.). In addition, intramolecular reactions that involve cyclization reactions between a reactive group and the α,β-unsaturated carbonyl-containing compound generated by prodrugs of formulae VI and VII can minimize by-product toxicity.

The cytotoxicity of the prodrugs are readily evaluated using cell lines that lack P450 activity (e.g. CYP3A4 activity). (Example C).

Non-Mutagenic Prodrugs

Prodrugs of the invention are generated by a postulated mechanism involving an initial oxidation followed by a β-elimination reaction. In some cases, e.g. certain prodrugs of formula VI and formula VII, the by-product of the reaction is an α,β-unsaturated carbonyl compound, e.g. vinyl phenyl ketone for prodrugs where V=Ph, Z, W and W'=H. Compounds that react with nucleophiles via a Michael addition can lead to certain toxicities, (e.g. acrolein produces bladder toxicities) and mutagenic activity. The degree to which these activities limit the use of compounds of Formula VI is dependent on the severity of the toxicity and the indicated disease.

Improved analogs of formula I are readily discoverable using known assays that can test for the mutagenicity of the prodrugs and its by-product.

Prodrugs that produce non-toxic and non-mutagenic by-products are especially preferred for the treatment of chronic diseases (e.g. diabetes). Frequently, it is difficult to predict the mutagenic properties of a compound. For example, a number of acrylates have been shown to produce positive mutagenic responses as indicated by increased chromosome aberrations and micronucleus frequencies in cultured L5179Y mouse lymphoma cells (Dearfield et al., *Mutagenesis* 4, 381–393 (1989)). Other acrylates, however, are negative in this test (*J. Tox. Envir. Health*, 34, 279–296 (1991)) as well as in the Ames test and the CHO assay which measures newly induced mutations at the hypoxanthine-guanine phosphoribosyltransferase (hgprt) locus (*Mutagenesis* 6, 77–85 (1991)). Phenyl vinyl ketone lacks teratogenic activity in rat embryos in culture suggesting that it may not be mutagenic nor highly toxic (*Teratology* 39, 31–37 (1989)).

Since mutagenicity and toxicity are not highly predictable properties, non-mutagenic prodrugs of formula I and their associated by-products can be readily identified by conducting well known in vitro and in vivo assays. For example, compounds can be tested in non-mammalian cell assays such as the Ames test, a fluctuation test in *Kl. pneumoniae*, a forward mutation assay with *S. typhimurium*, a chromosome loss assay in *Saccharomyces cerevisiae*, or a D3 recombinogenicity assay in *Saccharomyces cerevisiae*. Compounds can also be tested in mammalian cell assays such as the mouse lymphoma cells assay (TK+/– heterozygotes of L5178Y mouse lymphoma cells), assays in Chinese hamster ovary cells (e.g. CHO/HGPRT assay), and an assay in rat liver cell lines (e.g. RL1 or RL4). Each of these assays can be conducted in the presence of activators (e.g. liver microsomes) which may be of particular importance to these prodrugs. By conducting these assays in the presence of the liver microsomes, for example, the prodrug produces products, such as phenol or vinyl ketone. The mutagenicity of the by-product is measured either directly or as a prodrug where the results are compared to the parent drug alone. In addition, the assays can be carried out in the absence of activators and with cell lines that lack P450 activity and thereby enable measurement of the cytotoxicity and mutagenicity of the prodrug. Assays in liver cell lines are a preferred aspect of the invention since these cells have higher glutathione levels, which can protect the cell from damage caused by a Michael acceptor, as well as greater levels of intracellular enzymes used to detoxify compounds. For example, the liver contains reductases that with some by-products might result in reduction of the carbonyl.

A variety of end points are monitored including cell growth, colony size, gene mutations, micronuclei formation, mitotic chromosome loss, unscheduled DNA synthesis, DNA elongation, DNA breaks, morphological transformations, and relative mitotic activity.

In vivo assays are also known that assess the mutagenicity and carcinogenicity of compounds. For example, a non-mammalian in vivo assay is the Drosophila sex-linked recessive lethal assay. Examples of mammalian in vivo assays include the rat bone marrow cytogenetic assay, a rat embryo assay, as well as animal teratology and carcinogenicity assays.

In some cases the prodrug substituents are selected such that the by-product produced is poor Michael acceptor. For example, for class (2) prodrugs (V is aromatic or the like) when Z in formula I is an electron donator, the corresponding arylvinylketone produced are less likely to act as a Michael acceptor. Similarly, when W, W' or both W and W' are not hydrogen (e.g. methyl or phenyl) Michael addition to the beta-carbon is greatly diminished.

Enhancing Oral Bioavailability

The invention pertains to certain cyclic 1',3'-propanyl esters of phosph(oramid)ates and the use of these esters to deliver, most preferably via oral administration, a therapeutically effective amount of the corresponding drug containing a free —OH, —NHR$^2$, or —SH, preferably to an animal in need thereof. Prodrugs of the invention enhance oral bioavailability of certain drugs by changing the physical properties of the drug as a consequence of the prodrug moiety and its substituents V, Z, W, and W'. The active drug is referred to as MH.

Drugs containing amines are often protonated at physiological pH and are therefore poorly absorbed from the gastrointestinal tract. Prodrugs of the present invention attached to amines eliminate the charge and increase the overall hydrophobicity thereby enhancing absorption via passive diffusion processes. For example, many hydrophobic drugs are poorly absorbed because of very low water solubility. Prodrugs of these drugs, especially prodrugs that contain a weakly basic nitrogen (e.g. V=4-pyridine) greatly enhance water solubility. Water solubility is a particular problem with oncolytic drugs (e.g. taxol and taxol derivatives). Last, oral absorption can be limited by drug metabolism within the gastrointestinal tract, blood, or other extrahepatic organs, which can be prevented by a suitably positioned prodrug moiety.

The prodrugs of the invention exhibit improved properties that lead to enhanced oral bioavailability relative to the parent drug. Several characteristics of the present cyclic phosph(oramid)ate prodrugs may contribute to their ability to enhance oral bioavailability. First, the prodrugs exhibit good stability in aqueous solutions across a wide range of pHs. This pH stability prevents immediate hydrolysis in the mouth and GI tract prior to absorption. The pH stability can also be beneficial during formulation of the product.

Second, the prodrugs are resistant to esterases, phosphatases, and other non-oxidative enzymes (e.g. deaminases) that are abundant in the gastrointestinal tract. Because much of the administered dose remains intact in the G.I. tract, more of the drug can be absorbed by passive diffusion and enter the blood stream.

Last, the prodrug can limit metabolism at other sites on the molecule. For example, the prodrugs of the invention may eliminate metabolism by non-hepatic enzymes and thereby enable more of the drug to circulate in the blood stream for longer duration. Although not all of these properties will be applicable to every prodrug of every drug, each of these properties can enable more drug to survive the GI tract and be available for absorption.

Oral bioavailability can be calculated by comparing the area under the curve of prodrug, drug, and/or metabolite concentration over time in plasma, liver, or other tissue or fluid of interest following oral and i.v. administration. Oral bioavailability can often be measured by comparing the amount of the parent compound excreted in the urine, for example, after oral and i.v. administration of the prodrug. A lower limit of oral bioavailability can be estimated by comparison with the amount of parent drug excreted in the urine after administration of the prodrug (p.o.) and the prodrug or parent drug (i.v.). Prodrugs of the invention show improved oral bioavailability across a wide spectrum of prodrugs, with many preferably showing at least a 0.5–25-fold increase in oral bioavailability.

More preferably, oral bioavailability is enhanced by at least 2-fold compared to the parent drug.

Sustained Delivery

Drugs that undergo rapid elimination in vivo often require multiple administrations of the drug to achieve therapeutically-effective blood levels over a significant period of time. Alternative methods are available for this purpose including sustained release formulations and devices. Co-administration of compounds that block either the metabolism or elimination of the drug is another strategy. Prodrugs that breakdown over time can also provide a method for achieving sustained drug levels. In general, this property has not been possible with the known phosph(on)ate prodrugs since either they undergo rapid hydrolysis in vivo (e.g. acyloxyalkyl esters) or very slow conversion (e.g. di-aryl prodrugs).

The cyclic phosph(oramid)ates of the invention are capable of providing sustained drug release by providing a steady release of the drug over time. Suitably positioned prodrug moieties on the parent drug MH can prevent or slow systemic metabolism associated with the parent drug.

Sustained delivery of the drugs is achievable by selecting the prodrugs of formula I that are hydrolyzed in vivo at a rate capable of achieving therapeutically effective drug levels over a period of time. The cleavage rate of the drug may depend on a variety of factors, including the rate of the P450 oxidation, which is dependent on both the substituents on the prodrug moiety, the stereochemistry of these substituents and the parent drug. Moreover, sustained drug production will depend on the rate of elimination of the intermediate generated after oxidation and the availability of the prodrug to the liver, which is the major site of oxidation. Identification of the prodrug with the desired properties is readily achieved by screening the prodrugs in an assay that monitors the rate of drug production in the presence of the major P450 enzyme involved in the metabolism, in the presence of liver microsomes or in the presence of hepatocytes. These assays are illustrated in Examples B, and F, and A, respectively.

It is contemplated that prodrugs of the present invention could be combined to include, for example, one prodrug which produces the active agent rapidly to achieve a therapeutic level quickly, and another prodrug which would release the active agent more slowly over time.

Improved Pharmacodynamic Half-Life

The pharmacodynamic half-life of a drug can be extended by the novel prodrug methodology as a result of both its ability to produce drug over a sustained period and in some cases the longer pharmacokinetic half-life of the prodrug. Both properties can individually enable therapeutic drug levels to be maintained over an extended period resulting in an improvement in the pharmacodynamic half-life. The pharmacodynamic half-life can be extended by impeding the metabolism or elimination pathways followed by the parent drug. For some drugs, the prodrugs of the present invention are able to avoid the rapid metabolism or elimination pathways associated with the parent drug and thereby exist as the prodrug for extended periods in an animal. High levels of the prodrug for an extended period result in sustained production of the parent drug which can result in an improvement in the drug pharmacodynamic half-life.

Types of Parent Drugs

Various kinds of parent drugs can benefit from the prodrug methodology of the present invention. It is preferred that the prodrug phosph(oramid)ate moiety be attached to a hydroxy, amine, or thiol on the parent drug. In many cases the parent drug will have many such functional groups. The preferred group selected for attachment of the prodrug is the group that is most important for biological activity and is chemically suitable for attachment of the prodrug moiety. Thus, the phosph(oramid)ate moiety will prevent the prodrug from having biological activity. An inactive prodrug should limit systemic side effects because higher drug concentrations will be in the target organ (liver) relative to non-hepatic tissues. The amine should have at least one N—H bond, and preferably two.

Treatment of Cancer

The prodrug strategy in the current invention encompasses several features that are advantageously used in cancer therapies. The prodrug strategy can be effective in the treatment of liver cancer because the drug is cleaved by liver-abundant enzymes which suggests that a greater therapeutic index will result since much less parent drug is present in the blood and therefore available to produce side effects arising from effects on cells in the blood or via distribution to other tissues.

Cancer cells that express P450s, especially CYP3A4, are sensitive to prodrugs of the invention since the prodrugs are cleaved inside these cells to produce high local concentrations of the drug relative to drug concentrations in other tissues/cells that lack CYP3A4 activity. Studies reported in the literature suggest that certain carcinomas and sarcomas express CYP3A4. For example, hepatocellular carcinomas exhibit approximately 50–100% of normal CYP3A4 activity. Cancers outside the liver may also exhibit CYP3A4 activity whereas normal tissue surrounding the tumor is devoid of activity. Tumors that metastasize to the liver from non-P450-expressing organs (e.g. breast) often do not have P450 activity. Prodrugs of the invention, however, are still suitable for treatment of these tumors since the drug is produced in normal hepatocytes and depending on the drug, can diffuse out of the hepatocyte and into the tumor. The highest concentrations of the drug are in the liver and therefore the exposure of the liver tumor to the drug is high relative to extra-hepatic organs. Examples of preferred drug candidates that are specifically amenable to the strategy include, e.g. etoposide, teniposide, and other epipodophyllotoxins (such as NK-611, Azatoxin, and GL-331); camptothecin, topotecan, irinotecan, lurtotecan, 9-aninocamptothecin, and other camptothecins (such as DX-8951F, GG-211, SKF 107874, SKF 108025); neocarzinostatin, calicheamicin, esperamicin, and other enediyne antibiotics; paclitaxel, docetaxel, and other taxanes (such as FCE-28161); coformycin, 2'-deoxycoformycin; doxorubicin; daunorubicin; idarubicin, pirarubicin, epirubicin, and other anthracycline glycosides; mytomycin; eflornithine, and other polyamine biosynthesis inhibitors; combrestatin, combretastatin, and other analogs; vinblastine, vincristine, vindesine, vinorelbine, and other Vinca alkaloids; mycophenolic acid and other IMPDH inhibitors; mitoxantrone, piroxantrone, losoxantrone, and other anthrapyrazoles.

Treatment of Viral Infections

Drugs useful for treating viruses that infect the liver and cause liver damage, e.g. hepatitis virus strains, exhibit similar properties to the anticancer drugs in terms of efficacy, side effects and resistance. Such drugs are not nucleosides that are active in the phosphorylated form. In some cases, the drugs are already targeted for hepatitis. The prodrugs of these compounds could enhance the efficacy, increase the therapeutic index, improve the pharmacodynamic half-life and/or bypass drug resistance. Prodrugs of other agents used to treat viral infections other than hepatitis may also be made useful by administration of the prodrugs of this invention since the resistance will be avoided by delivery to the liver.

Treatment of Liver Fibrosis

It is contemplated that the prodrug methodology of the present invention could be used for the delivery of drugs useful for the treatment of liver fibrosis. Liver fibrosis is characterized by the excessive accumulation of extracellular matrix proteins, primarily collagen, in the liver. Liver fibrosis results from liver injury and is associated with the accumulation and activation of a variety of inflammatory cells, including neutrophils, monocytes/macrophages and platelets. Release of cytokines and growth factors from these cells leads to the recruitment and proliferation of fibroblasts and other related cells that excrete ECM proteins. In the case of the liver, the hepatic stellate cell (Ito cell), is the principal effector. Once activated, these cells are transformed from cells that in the normal liver are responsible for storing fats to cells that have many features of smooth muscle cells and actively secrete proteins. The proteins produced by the stellate cell include five types of collagen, heparin sulfate, dermatan, chondroitin sulfate proteoglycans, laminin, cellular fibronectin, tenascin, decorin and biglycan. Production of the ECMs leads to a high-density matrix in the subendothelial space which leads to loss of hepatocytic microvilli and sinusoidal fenestrations. Activated stellate cells are known to express CYP3A4 and therefore may be sensitive to drugs delivered as prodrugs of this invention.

Many potential drugs for treating liver fibrosis are limited by side effects due to inhibition of fibrotic processes at extrahepatic sites (wounds, tendons, etc). Potential drugs that could benefit from the prodrug approach include endothelin receptor antagonists, prostaglandin E1/E2, retinoids analogs, corticosteroids, D-penicillanine, prolyl hydroxylase inhibitors, lysyl oxidase inhibitors, NF-kappaB transcription factor antagonists, cytokine production inhibitors, metalloproteinase inhibitors, and cytotoxic agents (mentioned above for cancer treatments).

Agents Used to Modulate CYP Activity

A variety of methods may be used to enhance the in vivo activity of compounds of formula I. For example, various drugs are known that enhance cytochrome P450 (CYP) activity. Enhancement frequently entails increased gene transcription. Four families of CYPs are particularly susceptible to induction, namely CYP1-4. Induction is purportedly via receptors that are activated by various xenobiotics. For example, CYP1 gene activation frequently involves activation of the Ah receptor by polycyclic aromatic hydrocarbons. CYP2-4 are activated via orphan nuclear receptors. Data suggests that the nuclear receptor CAR (constitutively Active Receptor) is responsible for phenobarbital CYP activation, especially CYP2 genes. The pregnane nuclear receptors (PXR or PAR or SXR) are thought to activate CYP3A genes whereas the PPAR (peroxisome proliferator activate receptor) is linked to CYP4 gene activation. All three xenobiotic receptors are highly expressed in the liver which accounts for the liver specificity of the P450 gene induction.

Xenobiotics known to induce CYP3 genes include phenobarbital, a variety of steroids, e.g. dexamethasone, antibiotics, e.g. rifampicin, and compounds such as pregnenolone-16a carbonitrile, phenytoin, carbamazepine, phenylbutazone, etc. A variety of methods are known that enable identification of xenobiotics that induce P450s, including a reporter gene assay in HepG2 cells (Ogg et al., *Xenobiotica* 29, 269–279 (1999). Other inducers of the CYP3A subfamily are known that act at the post-transcriptional level either by mRNA or protein stabilization, e.g. clotrimazole, TA and erythromycin. Compounds known to induce CYPs or identified in in vitro assays are then used to enhance CYP activity in vivo. For example, CYP activity is monitored in rats pre-treated with CYP modulators by e.g. evaluating liver microsomes over a period of time to determine the optimal pre-treatment period, dose and dosing frequency. Rats with enhanced CYP activity, especially the CYP activity responsible for activation of the prodrugs (e.g. CYP3A4), are then treated with compounds of formula 1. Enhanced CYP activity can then lead to enhanced prodrug conversion and liver specificity. For example, enhanced metabolism of cyclophosphamide was found with pre-treatment with phenobarbital (Yu et al., *J. Pharm. Exp. Ther.* 288, 928–937 (1999).

In some cases, enhanced CYP activity may lead to unwanted drug metabolism. For example, enhanced activity of CYPs not involved in prodrug activation can result in increased drug metabolism and therefore decreased efficacy. In addition, increased CYP activity in other tissues, e.g. CYP3A4 in the gastrointestinal tract, could result in decreased prodrug absorption and liver drug levels. Inhibitors of CYP activity are known that might be useful in minimizing unwanted drug metabolism. For example, grapefruit juice is known to inactivate gastrointestinal CYP3A4 and to result in enhanced absorption of numerous drugs metabolized by CYP3A4. CYP inhibitors are also known for many of the CYP subfamilies that can be useful for attenuating unwanted drug metabolism while maintaining CYP activity important for prodrug cleavage. For example, the CYP3A inhibitor TAO was used to modulate cyclophosphamide metabolism in vivo in a manner that decreased the formation of toxic metabolites that do not contribute to its antitumor activity.

Use for Treating Hepatocellular Carcinomas (HCC)

Oncolytic drugs such as etoposide, topotecan, taxol, etc. that contain a biologically important hydroxyl or oncolytic drugs such as mitomycin, anthracyclin antibiotics (e.g. doxorubicin) that contain a biologically important amino group or oncolytic drugs that contain a sulfhydryl moiety are suitable drugs for conversion to compounds of formula 1. These compounds are especially useful for the treatment of HCC since transformed cells contain abundant CYP3A4 activity. Furthermore it is known that delivery of 5-FU, taxol and other oncolytic agents to the liver via portal vein or intra-arterial infusion has shown significant success with response rates as high as 50% (normal rate is less than 20%). However, the complexity, expense and high incidence of secondary complications associated with long-term percutaneous catheterization or infusion devices diminishes the likelihood that local drug administration will become the standard therapy for liver cancer.(Venook, A. P. *J. Clin. Oncol.* 12, 1323–1334 (1994); b) Atiq, O. T.; Kemeny, N.; Niedzwiecki, D.; et al. *Cancer,* 69, 920–924 (1992).)

Use for Treating Secondary Liver Tumors

Oncolytic drugs such as etoposide, topotecan, taxol, etc. that contain a biologically important hydroxyl or oncolytic drugs such as mitomycin, methotrexate, anthracyclin antibiotics (e.g. doxorubicin) that contain a biologically important amino group or oncolytic drugs that contain a sulfhydryl moiety are suitable drugs for conversion to compounds of formula 1. Although these tumors often exhibit substantially lower CYP activity than normal tissues, antitumor effects are gained via selection of oncolytic agents that once produced in liver hepatocytes, diffuse out of the hepatocyte and enter the bloodstream as well as nearby cells. Since drug generation is in the liver, a greater concentration of the drug is found in nearby tissue than in extrahepatic tissue thereby leading to enhanced efficacy and an increased therapeutic index.

Use for Treating Extra-Hepatic Carcinomas

Oncolytic drugs such as etoposide, topotecan, taxol, etc. that contain a biologically important hydroxyl or oncolytic drugs such as mitomycin, methotrexate, anthracyclin antibiotics (e.g. doxorubicin) that contain a biologically important amino group or oncolytic drugs that contain a sulfhydryl moiety are suitable drugs for conversion to compounds of formula 1. In general, the CYP3 family of genes is expressed in normal tissues predominantly in the liver and gastrointestinal tract. CYP activity, however, is also known to be expressed in various soft tissue sarcomas and other cancers, possibly as part of a drug resistance mechanism. To date, CYP3 activity has been found in renal cancer, lung cancer, stomach cancer, breast cancer. Little tumor heterogeneity is observed (Murray et al., *J. Pathology,* 171, 49–52 (1993); Murray et al., *British J. Cancer,* 79, 1836–1842 (1999)). Accordingly, the prodrugs of formula 1 are useful for treating cancers in which CYP activity, particularly CYP3A, is present.

Methods for Monitoring Patient P450 Activity

CYP activity is known to exhibit significant differences across individuals. The range for CYP3A4 is 5- to 20-fold although most individuals are within a 3-fold range. Modest decreases are noted for individuals with liver disease (30–50%) or advanced age (25–50%). Differences for gender are even more modest(<25%). Methods for phenotyping an individual's CYP activity are known and could be useful in predicting who should receive drugs that modulate CYP activity. Evasive procedures include liver biopsy. Non evasive procedures have been reported, including an "erythromycin breath test" which is based on the exhalation of 14CO2 generated from the CYP3A-mediated N-demethylation of radiolabeled erythromycin (iv). (Watkins, *Pharmacogenetics* 4, 171–184 (1994)).

Gene Therapy

Introduction into tumor cells genes that encode for enzymes not normally expressed represents a new therapeutic strategy for increasing the therapeutic effectiveness of anticancer chemotherapies. The general strategy entails expression of an enzyme that catalyzes the breakdown of a prodrug of an anticancer drug thereby localizing the drug in or near the tumor mass and limiting exposure elsewhere. The strategy has been demonstrated using the HSV-TK gene wherein the thymidylate kinase specifically expressed in the transfected cells activates ganciclovir to the monophosphate which is then converted by other kinases to the tumor cell killing triphosphate. A similar strategy uses the bacterial cytosine deaminase gene for conversion of 5-fluorouracil to 5-fluorocytosine. Other genes have been considered including carboxypeptidase G2, nitro reductase, purine nucleoside phosphorylation, etc. In addition, CYP gene transfer has been explored as a way to enhance the chemotherapeutic effect of cyclophosphamide and ifosfamide, two drugs known to be activated by CYPs. For example, human breast cancer cells were sensitized by transfection with the CYP2B1 gene (Chen et al., *Cancer Research,* 56, 1331 1340 (1996)). The advantage of this strategy relative to the HSV-TK gene strategy is that the product of the CYP catalyzed oxidation readily diffuses outside of the tumor cell and into nearby cells. In contrast to monophosphate products of the HSV-TK strategy, the product can enter cells that are not in cell-cell contact and therefore produce a more widespread tumor killing effect (Chen and Waxman, *Cancer Research,* 55, 581–589 (1995)).

Compounds of formula 1 can be made more effective by using gene therapy to introduce the gene that encodes the CYP specifically involved in prodrug cleavage. The specific CYP that breaks down the prodrug is readily determined using some or all of the following steps: 1) demonstrate prodrug cleavage using human microsomes; 2) classify the subfamily by comparing activity with microsomes induced with various subfamily specific inducers (e.g. CYP3 enzymes are induced with a variety of steroids, e.g. dexamethasone, antibiotics, e.g. rifampicin, and compounds such as pregnenolone-16alpha carbonitrile, phenytoin, carbamazepine, phenylbutazone, etc.; 3) identify the CYP or CYPs responsible for prodrug activation by using known CYP subfamily specific inhibitors (e.g. troleandomycin, erythromycin, ketoconazole and gestodene) and/or by using neutralizing antibodies; 4) confirm CYP subfamily by demonstrating turnover via the recombinant enzyme.

Genes are introduced to the tumor using a suitable vector (e.g. retroviral vectors, adenoviral vectors) or via direct DNA injection. In theory genes could be introduced into cells which are transplanted into the tumor mass. The compounds of formula 1 are then introduced following significant enhancement of the CYP activity in the tumor.

Potential Non-Cancer Uses

A variety of liver diseases are suitable targets for compounds of formula I. For example, hepatitis is treated with a variety of drugs wherein prodrugs of the type shown in formula 1 will exhibit significant advantages either in regards to efficacy, safety, and/or pharmacokinetics. Other diseases include liver fibrosis wherein disease progression may be slowed or stopped with treatment of proline hydroxylase inhibitors, lysine hydroxylase inhibitors, steroids, non-steroids anti-inflammatory agents, Methotrexate, Ursodeoxycholic acid, and Penicillamine (also for Wilson's disease). Other possible areas that the prodrugs are useful include the delivery of antimalarial agents, various hepatoprotectants, diagnostic agents etc. Other drugs include azathioprine, chlorambucil.

Preferred Compounds

The compounds of the invention are substituted 6-membered cyclic 1,3-propane diester prodrugs of certain phosph(oramid)ates as represented by Formula I:

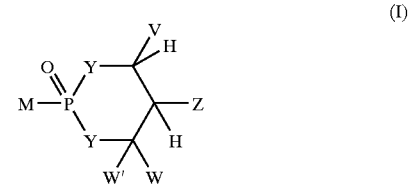

(I)

wherein:
V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2_2)OH$, —$CH(C\equiv CR^2)OH$, —$R^2$, —$NR^2_2$, —$OCOR^3$, —$OCO_2R^3$, —$SCOR^3$, —$SCO_2R^3$, —$NHCOR^2$, —$NHCO_2R^3$, —$CH_2NHaryl$, —$(CH_2)_p$—$OR^{12}$, and —$(CH_2)_p$—$SR^{12}$;

p is an integer 2 or 3;

with the provisos that:
a) V, Z, W, W' are not all —H; and
b) when Z is —$R^2$, then at least one of V, W, and W' is not —H, alkyl aralkyl, or alicyclic;
c) when Z is $CHR^2OH$, then M is not —NH(lower alkyl), —N(lower alkyl)$_2$, —NH(lower alkylhalide), —N(lower alkylhalide)$_2$ or —N(lower alkyl)(lower alkylhalide); and
d) when V is aryl or substituted aryl, then M is not —O(D) where D is hydrogen, a metal ion or an ammonium ion;

$R^2$ is selected from the group consisting of $R^3$ and —H;
$R^3$ is selected from the group consisting of alkyl, aryl, alicyclic, and aralkyl;
$R^6$ is selected from the group consisting of —H, lower alkyl, acyloxyalkyl, alkoxycarbonyloxyalkyl, and lower acyl;
$R^{12}$ is selected from the group consisting of —H, and lower acyl;

each Y is independently selected from the group consisting of —O—, and —$NR^6$—;

M is selected from the group consisting of drugs MH containing an —OH, —$NHR^2$, or —SH group, and that is attached to the phosphorus in formula I via O, N, or S of said OH, —$NHR^2$, or SH group;

and pharmaceutically acceptable prodrugs and salts thereof.

In general, preferred substituents, V, Z, W, and W' of formula I are chosen such that they exhibit one or more of the following properties:

(1) enhance the oxidation reaction since this reaction is likely to be the rate determining step and therefore must compete with drug elimination processes.
(2) enhance stability in aqueous solution and in the presence of other non-P450 enzymes;
(3) enhance cell penetration, e.g. substituents are not charged or of high molecular weight since both properties can limit oral bioavailability as well as cell penetration;
(4) promote the β-elimination reaction following the initial oxidation by producing ring-opened products that have one or more of the following properties:
  a) fail to recyclize;
  b) undergo limited covalent hydration;
  c) promote β-elimination by assisting in the proton abstraction;
  d) impede addition reactions that form stable adducts, e.g. thiols to the initial hydroxylated product or nucleophilic addition to the carbonyl generated after ring opening; and
  e) limit metabolism of reaction intermediates (e.g. ring-opened ketone);
(5) lead to a non-toxic and non-mutagenic by-product with one or more of the following characteristics. Both properties can be minimized by using substituents that limit Michael additions, e.g.:
  a) electron donating Z groups that decrease double bond polarization;
  b) W groups that sterically block nucleophilic addition to the β-carbon;
  c) Z groups that eliminate the double bond after the elimination reaction either through retautomerization (enol->keto) or hydrolysis (e.g. enamine);
  d) V groups that contain groups that add to the α,β-unsaturated ketone to form a ring;
  e) Z groups that form a stable ring via Michael addition to double bond; and
  f) groups that enhance detoxification of the by-product by one or more of the following characteristics:
    (i) confine to liver; and
    (ii) make susceptible to detoxification reactions (e.g. ketone reduction); and
(6) capable of generating a pharmacologically active product.

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 4 heteroatoms, preferably independently selected from nitrogen, oxygen, and sulfur. Suitable heteroalicyclic groups include groups having from 2 to about twenty carbon atoms and from 1 to 5 heteroatoms, preferably independently selected from nitrogen, oxygen, phosphorous, and sulfur.

Preferably, M is attached via an —OH, or —$NHR^2$ group. In one preferred aspect, M is attached to the phosphorus in formula I via an oxygen atom. In another aspect, it is preferred when M is attached via a nitrogen.

In another preferred aspect, MH is useful for the treatment of diseases of the liver or metabolic diseases where the liver is responsible for the overproduction of a biochemical end product. Preferably, such disease of the liver is selected from the group consisting of hepatitis, cancer, fibrosis, malaria, urate production, and chronic cholecystalithiasis. It is more preferred when treating such diseases that MH is an antiviral or anticancer agent.

Preferably, the metabolic disease that MH is useful for hyperlipidemia, diabetes, atherosclerosis, and obesity.

In another aspect, it is preferred when the biochemical end product is selected from the group consisting of glucose, cholesterol, fatty acids, and triglycerides.

In compounds of formula I, preferably both Y groups are —O—; or one Y is —O— and one Y is —$NR^6$—. When only one Y is $NR^6$—, preferably the Y closest to W and W' is —O—. Most preferred are prodrugs where both Y groups are —O—.

More preferred is when V is selected from the group consisting of aryl, substituted aryl, heteroaryl, and substituted heteroaryl.

More preferred V groups of formula VI are aryl, substituted aryl, heteroaryl, and substituted heteoaryl. Preferably Y is —O—. Preferred compounds of formula VI include those in which Z, W, and W' are H, and Z is selected from the group of aryl, substituted aryl, heteroaryl, and substituted heteroaryl. Particularly preferred aryl and substituted aryl groups include phenyl, and phenyl substituted with 1–3 halogens. Especially preferred are phenyl, 3,5-dichlorophenyl, 3-bromo-4-fluorophenyl, 3-chlorophenyl, 2-bromophenyl, and 3-bromophenyl.

It is also especially preferred when V is selected from the group consisting of monocyclic heteroaryl and monocyclic substituted heteroaryl containing at least one nitrogen atom. Most preferred is when such heteroaryl and substituted heteroaryl is 4-pyridyl, and 3-bromopyridyl, respectively.

It is also especially preferred when V is selected from the group consisting of heteroaryl and substituted heteroaryl.

Most preferred is when such heteroaryl is 4-pyridyl.

In another aspect, it is preferred when together V and W are connected via an additional 3 carbon atoms to form an optionally substituted cyclic group containing 6 carbon atoms and monosubstituted with one substituent selected from the group consisting of hydroxy, acyloxy, alkoxycarbonyloxy, alkylthiocarbonyloxy, and aryloxycarbonyloxy attached to one of said additional carbon atoms that is three atoms from a Y attached to the phosphorus. In such compounds, it is more preferred when together V and W form a cyclic group selected from the group consisting of —CH$_2$—CH(OH)—CH$_2$—, CH$_2$CH(OCOR$^3$)—CH$_2$—, and —CH$_2$CH(OCO$_2$)R$^3$)—CH$_2$—.

Another preferred V group is 1-alkene. Oxidation by P450 enzymes is known to occur at benzylic and allylic carbons.

In one aspect, preferred V groups include —H, when Z is —CHR$^2$OH, —CH$_2$OCOR$^3$, or —CH$_2$OCO$_2$R$^3$.

In another aspect, when V is aryl, substituted aryl, heteroaryl, or substituted heteroaryl, preferred Z groups include —OR$^2$, —SR$^2$, —CHR$^2$N$_3$, —R$^2$, NR$^2_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$OR$^{12}$, and —(CH$_2$)$_p$—SR$^{12}$. More preferred Z groups include —OR$^2$, —R$^2$, —OCOR$^3$, —OCO$_2$R$^3$, —CH$_3$, —NHCOR$^2$, —NHCO$_2$R$^3$, —(CH$_2$)$_p$—OR$^{12}$, and —(CH$_2$)$_p$—SR$^{12}$. Most preferred Z groups include —OR$^2$, —H, —OCOR$^3$, —OCO$_2$R$^3$, and —NHCOR$^2$. In one preferred aspect, Z is not —OR$^2$, —SR$^2$, or NR$^2_2$.

Preferred W and W' groups include H, R$^3$, aryl, substituted aryl, heteroaryl, and substituted aryl. Preferably, W and W' are the same group. More preferred is when W and W' are H.

In one aspect, prodrugs of formula VI are preferred:

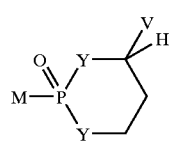

VI wherein

V is selected from the group consisting of aryl, substituted aryl, heteroaryl, and substituted heteroaryl, 1-alkenyl, and 1-alkynyl. More preferred V groups of formula VI are aryl, substituted aryl, heteroaryl, and substituted hetoaryl. Preferably Y is —O—. Particularly preferred aryl and substituted aryl groups include phenyl and substituted phenyl. Especially preferred are phenyl, 3,5-dichlorophenyl, 3-bromo-4-fluorophenyl, 3-chlorophenyl, 2-bromophenyl, and 3-bromophenyl. Particularly preferred heteroaryl groups include monocyclic substituted and unsubstituted heteroaryl groups. Especially preferred are phenyl, 3,5-dichlorophenyl, 3-bromo-4-fluorophenyl, 3-chlorophenyl, 2-romophenyl, and 3-bromophenyl, 4-pyridyl, and 3-bromopyridyl. Preferably, Z, W, and W' are H. Preferred compounds of formula VI include those in which Z is selected from the group of —OR$^2$, —SR$^2$, —R$^2$, —NR$^2_2$, —OCOR$^3$, —OCO$_2$R$^3$, —SCOR$^3$, —SCO$_2$R$^3$, —NHCOR$^2$, —NHCO$_2$R$^3$, —(CH$_2$)p—OR12, and —(CH$_2$)$_p$—SR$^{12}$.

In one aspect, the compounds of formula VI preferably have a group Z which is H, alkyl, alicyclic, hydroxy, alkoxy, OC(O)R$^3$, OC(O)OR$^3$, or NHC(O)R$^2$. Preferred are such groups in which Z decreases the propensity of the by-product, vinylaryl ketone to undergo Michael additions. Preferred Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analog is highly mutagenic. Other groups could serve a similar function, e.g. Z=OR$^6$, NHAc, etc. Other groups may also prevent the Michael addition especially groups that result in removal of the double bond altogether such as Z=—OH, —OC(O)R$^3$, —OCO$_2$R$^3$, and NH$_2$, which will rapidly undergo retautomerization after the elimination reaction. Certain W and W' groups are also advantageous in this role since the group(s) impede the addition reaction to the β-carbon or destabilize the product. Another preferred Z group is one that contains a nucleophilic group capable of adding to the α,β-unsaturated double bond after the elimination reaction ie. (CH$_2$)$_p$SH or (CH$_2$)$_p$OH where p is 2 or 3. Yet another preferred group is a group attached to V which is capable of adding to the α,β-unsaturated double bond after the elimination reaction. V groups are preferred that are substituted aryl and substituted heteroaryl wherein the aryl or heteroaryl group has a suitably positioned nucleophile e.g. 2-OH or SH which can add by an intramolecular reaction to the α,β-unsaturated carbonyl.

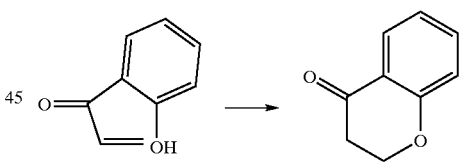

In another aspect, prodrugs of formula VII are preferred:

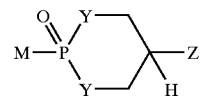

VII wherein

Z is selected from the group consisting of: —CHR$^2$OH, —CHR$^2$OCOR$^3$, —CHR$^2$OC(S)R$^3$, —CHR$^2$OCO$_2$R$^3$, —CHR$^2$OC(O)SR$^3$, and —CHR$^2$OC(S)OR$^3$. Preferably Y is —O—. More preferred Z groups include —CHR$^2$OH, —CHR$^2$OC(O)R$^3$, and —CHR$^2$OCO$_2$R$^3$. Preferably, when Z is—CHR$^2$OH, and W and W' are H, then M does not include within its structure adenine, cytosine, guanine, thymine, uracil, 2,6-diamino purine, hypoxanthine, or a compound of the formula:

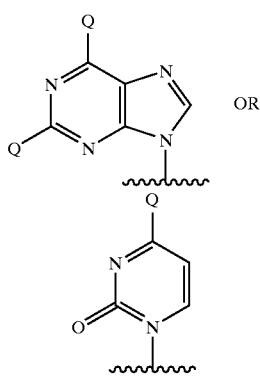

wherein Q is independently H, Cl, $NHR^Q$, $NR^Q_2$, $NHC(O)R^Q$, $N(C(O)R^Q)_2$, OH or $NCHN(R^Q)_2$; and $R^Q$ is $C_1$–$C_{20}$ alkyl, aryl or aralkyl all optionally substituted with hydroxy or halogen. Also preferred are compounds of formula VII in which when Z, W, and W' are H and V is aryl, substituted aryl, heteroaryl or substituted heteroaryl, then M does not include within its structure a group of the following formula:

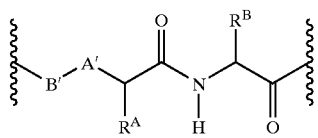

wherein:

$R^A$ and $R^B$ are independently hydrogen, optionally substituted alkyl having from 1 to about 14 carbons, or optionally substituted cycloalkyl having from 3 to about 10 carbons;

A' is NH or $(CH_2)_k$ where k is an integer from 0 to 3; and

B' is carbonyl or $SO_2$. Also preferred are compounds of formula VII were V, W, and W' are H.

In another aspect, prodrugs of formula VIII are preferred:

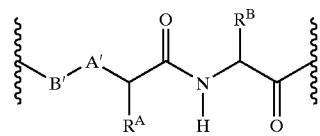

VIII wherein

Z' is selected from the group consisting of —OH, —OC(O)$R^3$, —OCO$_2$ $R^3$, and —OC(O)S$R^3$;

$D^4$ and $D^3$ are independently selected from the group consisting of —H, alkyl, $OR^2$, —OH, and —OC(O)$R^3$; with the proviso that at least one of $D^4$ and $D^3$ are —H. Preferably Y is —O—. An especially preferred Z group is OH.

In one preferred embodiment, W' and Z are —H, W and V are both the same aryl, substituted aryl, heteroaryl, or substituted heteroaryl, and W and V are cis to each other. In another preferred embodiment, W' and Z are —H, W and V are both the same aryl, substituted aryl, heteroaryl, substituted heteroaryl, and W and V are trans to each other. Preferably Y is —O.

In another preferred embodiment, W and W' are H, V is selected from the group consisting of aryl, substituted aryl, heteroaryl, substituted heteroaryl, and Z is selected from the group consisting of —H, $OR^2$, and —$NHCOR^2$. More preferred are such compounds where Z is —H. Preferably, when Z, W, and W' are H and V is aryl, substituted aryl, heteroaryl or substituted heteroaryl, then M does not include within its structure a group of the following formula:

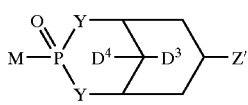

wherein:

$R^A$ and $R^B$ are independently hydrogen, optionally substituted alkyl having from 1 to about 14 carbons, or optionally substituted cycloalkyl having from 3 to about 10 carbons;

A' is NH or $(CH_2)_k$ where k is an integer from 0 to 3; and

B' is carbonyl or $SO_2$.

Preferably, such compound have M attached via oxygen. Most preferred are such compounds where oxygen is in a primary hydroxyl or a phenolic hydroxyl group. Also more preferred, are those compounds where V is phenyl or substituted phenyl.

In one embodiment of class (2) prodrugs, preferred are those where the oxygen double bonded to the phosphorus is cis to the H that is geminal to V.

Also more preferred, are those compounds where V is an optionally substituted monocyclic heteroaryl containing at least one nitrogen atom. Preferably such compounds have M attached via oxygen. Most preferred are such compounds where said oxygen is in a primary hydroxyl group or a phenolic hydroxyl. Especially preferred are such compounds where V is 4-pyridyl.

In these compounds it is also preferred when MH is selected from the group consisting of the classes Epipodophyllotoxins, Camptothecins, Anthracyclines, Anthrapyrazoles, Combretastatin Analogs, Enediyine antibiotics, and Taxanes.

Preferred Epipodophyllotoxins include Etoposide, Teniposide, NK-611, GL-331, and azatoxin. More preferred are Etoposide and Teniposide. Preferably, the epipodophyllotoxins are attached to the phosphorus via the phenolic hydroxy group.

Preferred Camptothecins include Camptothecin, Topotecan, Irinotecan (CPT-11), Lurtotecan (GI 147211), 9-aminocamptothecin, GG-211, DX-8951F, SKF 107874, and SKF 108025. Preferably, the Camptothecins are attached to the phosphorus via the C-20 hydroxyl which is tertiary hydroxy group on the lactone ring. More preferred Camptothecins include Camptothecin, Topotecan, Irinotecan, Lurtotecan, and 9-aminocamptothecin. Preferably, these compounds are attached via the C-20 hydroxyl group. For Topotecan, it is also preferable to attach to the phosphorus via the phenolic hydroxyl group. Most preferred Camptothecins include Topotecan and Irinotecan.

Preferred Taxanes include paclitaxel, docetaxel, and FCE-28161. Preferably, the taxanes are attached to the phosphorus via a hydroxy group on the side chain or the secondary hydroxy group on the cyclohexyl ring. More preferred Taxanes include paclitaxel.

Preferred combretastatins include combretastain A-4 and the reported (S,S) dioxolane analog (*Bioorg. Med. Chem. Lett.* 88: 1997–2000 (1998). Preferably, combretastatins are attached to phosphorus via the phenolic hydroxyl.

Preferred anthrapyrazoles include mitoxantrone, piroxantrone, and Losoxantrone. Preferably, the anthrapyrazoles are attached to phosphorus via a primary alcohol, phenolic hydroxy, or amine depending on the structure. In one aspect, it is preferred to attach the anthrapyrazole via a phenolic hydroxyl. In another aspect it is preferred to attach the anthrapyrazole via a primary alcohol. Especially preferred is mitoxantrone attached to phosphorus via a phenolic hydroxyl.

Preferred Anthracyclines include Doxorubicin, Daunorubicin, Idarubicin, Pirarubicin, and Epirubicin. Preferably, the anthracyclines are attached to the phosphorus via an amine on the sugar moiety. In another preferred aspect, the Anthracyclines are attached to the phosphorus via an alcohol or phenolic hydroxy group. More preferred is attaching via the secondary glycosidic hydroxyl or, when present, a primary alcohol (e.g., Doxorubicin). More preferred Anthracyclines are Doxorubicin, Pirarubicin, Epirubicin, and Idarubicin. Especially preferred Anthracyclines include Pirarubicin and Doxorubicin. In another preferred aspect, the Anthracyclines are attached to the phosphorus via an alcohol or phenolic hydroxy group. More preferred is attaching via the secondary glycosidic hydroxyl or, when present, a primary alcohol (e.g., Doxorubicin).

Preferred Enediyne Antibiotics include neocarzinostatin, calicheamicin, and esperamicin. Preferably, the enediyne antibiotics are attached to the phosphorus via a secondary amine on the sugar moiety. In another aspect, the Enediyne Antibiotics are attached to the phosphorus via a glycosidic hydroxyl. More preferred Enediyne Antibiotics include Neocarzinostatin and Calicheamicin, Dynemicin.

Particularly preferred are such compounds where V is selected from the group consisting of phenyl and 4-pyridyl and MH is selected from the group consisting of etoposide.

Also preferred is when MH is selected from the group consisting of etoposide and doxorubicin.

Preferably, oral bioavailability is at least 5%. More preferably, oral bioavailability is at least 10%.

P450 oxidation can be sensitive to stereochemistry which might either be at phosphorus or at the carbon bearing the aromatic group. The prodrugs of the present invention have two isomeric forms around the phosphorus. Preferred is the stereochemistry that enables both oxidation and the elimination reaction. Preferred is the cis-stereochemistry. In contrast, the reaction is relatively insensitive to the group M since cleavage occurred with a variety of phosphate and phosphoramidates. Accordingly, the group M represents a group that as part of a compound of formula I enables generation of a biologically active compound in vivo by conversion to MH via the corresponding M—$PO_3^{2-}$, M—P(O)($NHR^6$)$_2$, or M—P(O)($O^-$)($NHR^6$). The atom in M attached to phosphorus may be O, S or N. The active drug may be MH or a metabolite of M—H, but not M—$PO_3^{2-}$ or higher order phosphates, useful for treatment of diseases in which the liver is a target organ, including diabetes, hepatitis, liver cancer, liver fibrosis, malaria and metabolic diseases where the liver is responsible for the overproduction of a biochemical end products such as glucose (diabetes), cholesterol, fatty acids and triglycerides (atherosclerosis). Moreover, M—H may be useful in treating diseases where the target is outside the liver in tissues or cells that can oxidize the prodrug.

Other preferred M groups include drugs useful in treating diabetes, viral infections, liver fibrosis, parasitic infections, and hyperlipidemia. Such anti-diabetic agents do not include FBPase inhibitors. Generally FBPase inhibitors contain a phosphonate or phosph(oramid)ate group to be active. Specifically, M does not include within its structure optionaly substituted 2-aminocarbonylamino-benzimidazoles, optionally substituted 8-aminocarbonylaminopurines, otionally substituted 2-aminocarbonylamino-indoles, or optionally substituted 2-aminocarbonylamino-azaindole as described in WO 98/39343, WO 98/39344, and WO 98/39342, which are incorporated by reference in their entirety.

The preferred compounds of formula VIII utilize a Z' group that is capable of undergoing an oxidative reaction that yields an unstable intermediate which via elimination reactions breaks down to the corresponding M—$PO_3^{2-}$, M—P(O)($NHR^6$)$_2$, or M—P(O)($O^-$)($NHR^6$). An especially preferred Z' group is OH. Groups $D^4$ and $D^3$ are preferably hydrogen, alkyl, —$OR^2$, —$OCOR^3$, but at least one of $D^4$ or $D^3$ must be H.

The following compounds and their analogs can be used in the prodrug methodology of the present invention.

Preferred classes of anticancer drugs include:
Epipodophyllotoxins, camptothecins, endiyne antibiotics, taxanes, coformycins, anthracycline glycosides, mytomycin, combretastatin, anthrapyrazoles, and polyamine biosynthesis inhibitors.

Preferred Epipodophyllotoxins include Etoposide, Teniposide, NK-611, GL-331, and azatoxin. More preferred are Etoposide and Teniposide. Preferably, the epipodophyllotoxins are attached to the phosphorus via the phenolic hydroxy group.

Preferred Camptothecins include Camptothecin, Topotecan, Irinotecan (CPT-11), Lurtotecan (GI 147211), 9-aminocamptothecin, GG-211, DX-8951F, SKF 107874, and SKF 108025. Preferably, the Camptothecins are attached to the phosphorus via the C-20 hydroxyl which is tertiary hydroxy group on the lactone ring. More preferred Camptothecins include Camptothecin, Topotecan, Irinotecan, Lurtotecan, and 9-aminocamptothecin. Preferably, these compounds are attached via the C-20 hydroxyl group. For Topotecan, it is also preferable to attach to the phosphorus via the phenolic hydroxyl group. Most preferred Camptothecins include Topotecan and Irinotecan.

Preferred Taxanes include paclitaxel, docetaxel, and FCE-28161. Preferably, the taxanes are attached to the phosphorus via a hydroxy group on the side chain or the secondary hydroxy group on the cyclohexyl ring. More preferred Taxanes include paclitaxel.

Preferred combretastatins include combretastatin A-4 and the reported (S,S) dioxolane analog (*Bioorg. Med. Chem. Lett.* 88: 1997–2000 (1998). Preferably, combretastatins are attached to phosphorus via the phenolic hydroxyl.

Preferred anthrapyrazoles include mitoxantrone, piroxantrone, and Losoxantrone. Preferably, the anthrapyrazoles are attached to phosphorus via a primary alcohol, phenolic hydroxy, or amine depending on the structure. In one aspect, it is preferred to attach the anthrapyrazole via a phenolic hydroxyl. In another aspect it is preferred to attach the anthrapyrazole via a primary alcohol. Especially preferred is mitoxantrone attached to phosphorus via a phenolic hydroxyl.

Preferably, the epipodophyllotoxins, camptothecins, combretastatins, anthrapyrazoles, and taxanes are linked to M via an oxygen.

In another aspect, other preferred antineoplastic drugs attached via oxygen include coformycin and deoxycoformycin. Preferably, the coformycins are attached to the phosphorus via the 5'-hydroxy on the sugar moiety.

Preferred Anthracyclines include Doxorubicin, Daunorubicin, Idarubicin, Pirarubicin, and Epirubicin.

Preferably, the anthracyclines are attached to the phosphorus via an amine on the sugar moiety. In another preferred aspect, the Anthracyclines are attached to the phosphorus via the secondary glycosidic hydroxyl or when present a primary alcohol (e.g., doxorubicin). More preferred Anthracyclines are Doxorubicin, Pirarubicin, Epirubicin, and Idarubicin. Especially preferred Anthracyclines include Pirarubicin and Doxorubicin. In another preferred aspect, the Anthracyclines are attached to the phosphorus via an alcohol or phenolic hydroxy group. More preferred is attaching via the secondary glycosidic hydroxyl or, when present, a primary alcohol (e.g., Doxorubicin).

In another aspect, Elsamitrocin is preferred. Preferably, elsamitrocin is attached to the phosphorus via the glycosidic amino group or the phenol, more preferably the phenol.

Preferred Enediyne Antibiotics include neocarzinostatin, calicheamicin, and esperamicin. Preferably, the enediyne antibiotics are attached to the phosphorus via a secondary amine on the sugar moiety. In another aspect, the Enediyne Antibiotics are attached to the phosphorus via a glycosidic hydroxyl. More preferred Enediyne Antibiotics include Neocarzinostatin and Calicheamicin.

In another aspect, Mitomycin is also preferred. Preferably, the Mitomycins are attached via the aziridine nitrogen.

Preferred Polyamine Biosynthesis Inhibitors include eflornithine. Preferably, the eflornithine is attached to the phosphorus via a primary amine.

Preferably, the anthracyclines, endiyne antibiotics, mitomycin, and polyamine biosynthesis inhibitors are attached via a nitrogen to the phosphorus.

Where drugs (MH) have more than one hydroxy (phenol, alcohol), thiol, and/or amine group, then in one aspect, it is preferred to attach to the group which is a) important for biological activity; and/or b) important for metabolic destruction of the drugs.

In another aspect, it is preferred to attach the phosphorus to an alcohol or an amine on MH. More preferred is attaching to an alcohol.

Preferred alcohol, amine, and thiol containing compounds encompassed by the invention are compounds with alcohols, amines, or thiols that are readily converted to compounds of formula 1. A preferred process for the conversion of an alcohol, amine or thiol to prodrugs of this invention entails reaction of the alcohol, amine, or thiol on the compound or suitably protected compound with a phosphorylating agent X—P(O)[—YCH(V)CH(Z)CWW'Y—] wherein X is a suitable leaving group (e.g. halogen, dialkyamine, cyclic secondary amine, and aryloxy). Another preferred process entails reaction of the alcohol, amine, or thiol with a X—P[—YCH(V)CH(Z)CWW'Y—] wherein X is a suitable leaving group (e.g. halogen, dialkyamine, and cyclic secondary amine) followed by oxidation of the resulting phosph(oramid)ite to the phosph(oramid)ate prodrug using a suitable oxidizing agent (e.g. t-butylhydroperoxide, peroxy acids).

Another process entails conversion of the corresponding M—$PO_3^{2-}$, M—$P(O)(NHR^6)_2$, or $MP(O)(NHR^6)(O^-)$ to compounds of formula 1. A preferred process for this conversion entails conversion to M—P(O)LL' wherein L and L' are independently leaving groups (e.g. halogen, dialkyamine, cyclic secondary amine, and aryloxy). Another process entails initial conversion of the alcohol into a leaving group followed by reaction with HO—P(O)[—YCH(V)CH(Z)CWW'Y—] in the presence of a suitable base. In each case, individual diastereomers are prepared either by isolation from a mixture of diasteromers or by using chiral precursors which are preferably generated using a chiral diol HOCH(V)CH(Z)C(W)(W')OH or corresponding chiral amino alcohol.

Most preferred are alcohols, amines, or thiols of the parent drug (MH) selected from the group wherein conversion of the alcohol, amine, or thiol to prodrugs of formula 1 results in substantial loss of biological activity prior to prodrug cleavage. Preferred —OH, amine, and —SH positions on drugs, M—H, are identified through either knowledge of known structure-activity relationships which indicate the importance of the alcohol, amine, or thiol for biological activity or by studies suitable for characterizing the biological activity of the prodrug without conversion to M—H. (e.g. cells devoid of P450 activity, Example C).

Most preferred are prodrugs that generate in vivo an unstable intermediate M—$PO_3^{2-}$, $MP(O)(NHR^6)(O^-)$, or $MP(O)(NHR^6)_2$ intermediate which is dephosphorylated by chemical hydrolysis or preferably by an enzyme (e.g. alkaline phosphatase) and more preferably by a phosphatase or amidase or both in the liver. Prodrugs that are converted to M—H are readily identified by known methods, including by incubation of the prodrug in the presence of enzymes that catalyze the oxidative cleavage (e.g. cytochrome P450s such as CYP3A4) and that catalyze the dephosphorylation (e.g. phosphatases) either together or as a stepwise process. (Example B) Alternatively, M—H generation can be monitored by incubating the prodrugs in the presence of hepatocytes (Example A.) Many alcohol-containing drugs are known that as the phosphate convert rapidly to the corresponding alcohol.

Preferred alcohols, amines, or thiols (M—H) are also alcohols, amines, or thiols wherein selective delivery of the drug to the liver provides a significant therapeutic benefit. The benefit is often observed as improved efficacy since greater liver selectivity can result in higher drug levels in the liver at a given dose or relative to drug levels in plasma. Greater efficacy is possible in cases where maximal efficacy is not achieved due to inadequate peak drug levels or due to inadequate exposure to the drug over a period of time. Inadequate exposure may result from side effects which limit the maximal dose. The benefit may also be exhibited as an improved therapeutic index since in many cases administration of drugs either systemically or orally results in high exposure of the drug to organs throughout the body. This exposure can result in certain toxicities and production of certain pharmacological side effects. For example, oncolytic agents often result in destruction of actively proliferating hematopoietic precursor cells which leads to decreased white blood cells and decreased platelet counts which in turn can result in life-threatening infections and hemorrhage. Other common toxicities include cardiac, pulmonary, reproductive function and nervous system toxicities as well as those observed in the gastrointestinal tract, urinary tract, and at the drug injection sites.

Selective breakdown of the drug by the liver, since the liver is the site which has the highest levels of the P450 isoenzymes that catalyze the oxidative cleavage of the prodrugs of formula 1, is envisioned to result in high liver drug concentrations. In some cases, the drug will remain predominantly in the liver due to high protein binding or due to metabolic processes (e.g. glucoronidation reactions) that convert the drug to metabolites that are retained by the liver. In other cases, the drug will diffuse out of the liver and enter the blood stream and subsequently other tissues. Even for drugs that diffuse out of the liver, however, the drug concentration in the liver will be higher than at extrahepatic sites since the drug is rapidly diluted by body fluids after it leaves the liver (e.g. blood and tissues). The liver drug concentrations should therefore be the highest except for drugs that are actively sequestered by other tissues in the body.

More preferred are compounds useful for treating diseases wherein the liver is the site of the disease (e.g. liver cancer, hepatic viral, bacterial and parasitic infections, liver fibrosis) or is an organ that significantly contributes to the disease (e.g. diabetes, atherosclerosis and obesity). In the latter case, elevated glucose levels in diabetic patients in the postabsorptive state are attributed to the overproduction of glucose by the liver. Elevated lipids and lipid precursors, e.g. cholesterol, fatty acids, triglycerides, and lipid particles are thought to contribute significantly to certain disease conditions such as atherosclerosis and associated heart and other organ diseases as well as obesity. Prodrugs of the invention can be of significant benefit in treating these diseases since the drug levels in the liver are higher than the levels attained after treatment with the drug itself. In other cases, the drug levels in the liver relative to other tissues or blood are higher than after treating with the drug itself. Either profile provides benefit either in the form of enhanced efficacy or improved therapeutic window.

Drugs containing a suitable alcohol include drugs in the epipodophyllotoxin, camptothecin, enediyne, taxane, Elsamitrucin, combretastatin, anthrapyrazole, anthracyclines, and coformycin, classes of anticancer drugs and analogs described in the literature.

Drugs containing a suitable amine include but are not limited to doxorubicin, pirarubicin, mitomycin, methotrexate, enediyne, ornithine analogs useful as polyamine biosynthesis inhibitors, and analogs described in the literature.

Drugs containing suitable thiol include but are not limited to penicillamine.

The following prodrugs are preferred compounds of the invention. The compounds are shown without depiction of stereochemistry since the compounds are biologically active as the diastereomeric mixture or as a single stereoisomer. Compounds named in Table 1 are designated by numbers assigned to the variables of formula VIa using the following convention: $M^1.V.L1.L2$ where Y is oxygen and Y' is oxygen. $M^1$ is a variable that represents compounds of the formula M—H which have a specific hydroxyl group that is phosphorylated with a group P(O)(Y—CH(V)CH2CH2-Y') to make compounds of formula VIa. V is an aryl or heteroaryl group that has 2 substituents, L1 and L2, at the designated positions.

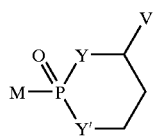

VIa

Variable $M^1$ is divided into four groups with the structures assigned to each group listed below:

Variable $M^1$: Group $M^1 1$:

1) Etoposide where —P(O)(Y—CH(V)CH2CH2-Y') is attached to the 4' phenolic hydroxyl.
2) Teniposide where —P(O)(Y—CH(V)CH2CH2-Y') is attached to the 4' phenolic hydroxyl.
3) NK-611 where —P(O)(Y—CH(V)CH2CH2-Y') is attached to the 4' phenolic hydroxyl.
4) Camptothecin where —P(O)(Y—CH(V)CH2CH2-Y') is attached to the C20 hydroxyl.
5) Irinotecan where —P(O)(Y—CH(V)CH2CH2-Y') is attached to the C20 hydroxyl.
6) 9-Aminocamptothecin where —P(O)(Y—CH(V) CH2CH2-Y') is attached to the C20 hydroxyl.
7) GG-211 where —P(O)(Y—CH(V)CH2CH2-Y') is attached to the C20 hydroxyl
8) Topotecan where —P(O)(Y—CH(V)CH2CH2-Y') is attached to the C20 hydroxyl
9) Topotecan where —P(O)(Y—CH(V)CH2CH2-Y') is attached to the phenolic hydroxyl.

Variable $M^1$: Group $M^1 2$:

1) Paclitaxel where —P(O)(Y—CH(V)CH2CH2-Y') is attached to the C2' hydroxyl.
2) Mitoxantrone where —P(O)(Y—CH(V)CH2CH2-Y') is attached to the primary hydroxyl.
3) Combretastatin A-4 where —P(O)(Y—CH(V)CH2CH2-Y') is attached to the phenolic hydroxyl
4) Azatoxin where —P(O)(Y—CH(V)CH2CH2-Y') is attached to the phenolic hydroxyl.
5) Mycophenolic acid where —P(O)Y—CH(V)CH2CH2-Y') is attached to the phenolic hydroxyl.
6) Coformycin where —P(O)(Y—CH(V)CH2CH2-Y') is attached to the ribofuranosyl 5' hydroxyl
7) Mitoxantrone where —P(O)Y—CH(V)CH2CH2-Y') is attached to the phenolic hydroxyl.
8) Paclitaxel where —P(O)(Y—CH(V)CH2CH2-Y') is attached to the phenolic hydroxyl in the phenyl propronate prodrugs of BMS180661
9) (S,S) dioxolane derivative of Combretastatin A4 where —P(O)(Y—CH(V)CH2CH2-Y') is attached to the phenolic hydroxyl.

Variable $M^1$: Group $M^1 3$:

1) Doxorubicin where —P(O)(Y—CH(V)CH2CH2-Y') is attached to the glycosidic primary amino group.
2) Daunorubicin where —P(O)(Y—CH(V)CH2CH2-Y') is attached to the glycosidic primary amino group.
3) Idarubicin where —P(O)(Y—CH(V)CH2CH2-Y') is attached to the glycosidic primary amino group.
4) Epirubicin where —P(O)(Y—CH(V)CH2CH2-Y') is attached to the glycosidic primary amino group.
5) Mitomycin where —P(O)(Y—CH(V)CH2CH2-Y') is attached to aziridine amino group.
6) Eflornithine where —P(O)(Y—CH(V)CH2CH2-Y') is attached to the sidechain amino group.
7) 9-Aminocamptothecin where —P(O)(Y—CH(V) CH2CH2-Y') is attached to the phenyl primary amino group.
8) Piroxantrone where —P(O)(Y—CH(V)CH2CH2-Y') is attached to the primary amino group.
9) Calicheamicin theta(I)1 where —P(O)(Y—CH(V) CH2CH2-Y') is attached to the glycosidic primary amino group.

Variable $M^1$: Group $M^1 4$:

1) Doxorubicin where —P(O)(Y—CH(V)CH2CH2-Y') is attached to the glycosidic hydroxyl group.
2) Pirarubicin where —P(O)(Y—CH(V)CH2CH2-Y') is attached to the glycosidic amino group.
3) Pirarubicin where —P(O)(Y—CH(V)CH2CH2-Y') is attached to the primary C14 hydroxyl group.
4) Pirarubicin where —P(O)(Y—CH(V)CH2CH2-Y') is attached to the phenolic hydroxyl furthest from the glycosidic residue.
5) Pirarubicin where —P(O)(Y—CH(V)CH2CH2-Y') is attached to the phenolic hydroxyl of N-(4-(hydroxy) phenylacetyl)pirarubicin.

6) Doxorubicin where —P(O)(Y—CH(V)CH2CH2-Y') is attached to the primary hydroxyl group.
7) Doxorubicin where —P(O)(Y—CH(V)CH2CH2-Y') is attached to the phenolic hydroxyl of N-(4-(hydroxy)phenylacetyl)pirarubicin
8) Losoxantrone where —P(O)(Y—CH(V)CH2CH2-Y') is attached to the phenolic hydroxyl.
9) Irinotecan where —P(O)(Y—CH(V)CH2CH2-Y') is attached to the phenolic hydroxyl of (4-(hydroxy)phenylacetyl) which is attached to the C20 hydroxyl.

I. VARIABLE V: GROUP V1

1) 2-(L1)-3(L2)phenyl
2) 2-(L1)-4(L2)phenyl
3) 2-(L1)-5(L2)phenyl
4) 2-(L1)-6(L2)phenyl
5) 3-(L1)-4(L2)phenyl
6) 3-(L1)-5(L2)phenyl
7) 3-(L1)-6(L2)phenyl
8) 2-(L1)-6(L2)-4-chlorophenyl
9) 3-(L1)-5(L2) 4-chlorophenyl

II. VARIABLE V: GROUP V2

1) 2-(L1)-3(L2) 4-pyridyl
2) 2-(L1)-5(L2) 4-pyridyl
3) 2-(L1)-6(L2) 4-pyridyl
4) 3-(L1)-5(L2) 4-pyridyl
5) 3-(L1)-6(L2) 4-pyridyl
6) 2-(L1)-4(L2) 3-pyridyl
7) 2-(L1)-5(L2) 3-pyridyl
8) 2-(L1)-6(L2) 3-pyridyl
9) 4-(L1)-5(L2) 3-pyridyl

III. VARIABLE V: GROUP V3

1) 4-(L1)-6(L2) 3-pyridyl
2) 5-(L1)-6(L2) 3-pyridyl
3) 3-(L1)-4(L2) 2-pyridyl
4) 3-(L1)-5(L2) 2-pyridyl
5) 3-(L1)-6(L2) 2-pyridyl
6) 4-(L1)-5(L2) 2-pyridyl
7) 4-(L1)-6(L2) 2-pyridyl
8) 3-(L1)-4(L2)-2-thienyl
9) 2-(L1)-5(L2) 3-furnayl

IV. VARIABLE L1

1) hydrogen
2) chloro
3) bromo
4) fluoro
5) methyl
6) isopropyl
7) methoxy
8) dimethylamino
9) acetoxy

V. VARIABLE L2

1) hydrogen
2) chloro
3) bromo
4) fluoro
5) methyl
6) isopropyl
7) methoxy
8) dimethylamino
9) acetoxy Preferred compounds are compounds listed in Table 1 using groups $M^1 1$ and V1. For example, compound 1.3.6.7 represents structure 1 of group $M^1 1$, i.e. etoposide; structure 3 of group V1, i.e. 2-(L1)-5-(L2)phenyl; structure 6 of variable L1, i.e. isopropyl; and structure 7 of variable L2, i.e. methoxy. The compound 1.3.6.7. therefore is etoposide with the P(O)[Y—CH(V)CH2CH2Y'] attached to the 4'phenolic hydroxyl group being {[1-(2-i-propyl-5-methoxyphenyl)-1,3-propyl]phosphoryl.

Preferred compounds are also compounds listed in Table 1 using groups $M^1 1$ and V2.

Preferred compounds are also compounds listed in Table 1 using groups $M^1 1$ and V3.

Preferred compounds are also compounds listed in Table 1 using groups $M^1 2$ and V1.

Preferred compounds are also compounds listed in Table 1 using groups $M^1 2$ and V2.

Preferred compounds are also compounds listed in Table 1 using groups $M^1 2$ and V3.

Preferred compounds are also compounds listed in Table 1 using groups $M^1 3$ and V1.

Preferred compounds are also compounds listed in Table 1 using groups $M^1 3$ and V2.

Preferred compounds are also compounds listed in Table 1 using groups $M^1 3$ and V3.

Preferred compounds are also compounds listed in Table 1 using groups $M^1 4$ and V1.

Preferred compounds are also compounds listed in Table 1 using groups $M^1 4$ and V2.

Preferred compounds are also compounds listed in Table 1 using groups $M^1 4$ and V3.

Preferred compounds are represented by all of the above named compounds with the exception that Y is NH and Y' is oxygen.

Preferred compounds are represented by all of the above named compounds with the exception that Y is oxygen and Y' is NH.

Preferred compounds are represented by all of the above named compounds with the exception that Y and Y' are NH.

Preferred compounds are represented by all of the above named compounds with the exception that Y is NCH3 and Y' is oxygen.

Preferred compounds are represented by all of the above named compounds with the exception that Y is oxygen and Y' is NCH3.

TABLE 1

| | | | | | | | | | |
|---|---|---|---|---|---|---|---|---|---|
| 1.1.1.1 | 1.1.1.2 | 1.1.1.3 | 1.1.1.4 | 1.1.1.5 | 1.1.1.6 | 1.1.1.7 | 1.1.1.8 | 1.1.1.9 | 1.1.2.1 |
| 1.1.2.2 | 1.1.2.3 | 1.1.2.4 | 1.1.2.5 | 1.1.2.6 | 1.1.2.7 | 1.1.2.8 | 1.1.2.9 | 1.1.3.1 | 1.1.3.2 |
| 1.1.3.3 | 1.1.3.4 | 1.1.3.5 | 1.1.3.6 | 1.1.3.7 | 1.1.3.8 | 1.1.3.9 | 1.1.4.1 | 1.1.4.2 | 1.1.4.3 |
| 1.1.4.4 | 1.1.4.5 | 1.1.4.6 | 1.1.4.7 | 1.1.4.8 | 1.1.4.9 | 1.1.5.1 | 1.1.5.2 | 1.1.5.3 | 1.1.5.4 |
| 1.1.5.5 | 1.1.5.6 | 1.1.5.7 | 1.1.5.8 | 1.1.5.9 | 1.1.6.1 | 1.1.6.2 | 1.1.6.3 | 1.1.6.4 | 1.1.6.5 |
| 1.1.6.6 | 1.1.6.7 | 1.1.6.8 | 1.1.6.9 | 1.1.7.1 | 1.1.7.2 | 1.1.7.3 | 1.1.7.4 | 1.1.7.5 | 1.1.7.6 |
| 1.1.7.7 | 1.1.7.8 | 1.1.7.9 | 1.1.8.1 | 1.1.8.2 | 1.1.8.3 | 1.1.8.4 | 1.1.8.5 | 1.1.8.6 | 1.1.8.7 |
| 1.1.8.8 | 1.1.8.9 | 1.1.9.1 | 1.1.9.2 | 1.1.9.3 | 1.1.9.4 | 1.1.9.5 | 1.1.9.6 | 1.1.9.7 | 1.1.9.8 |
| 1.1.9.9 | 1.2.1.1 | 1.2.1.2 | 1.2.1.3 | 1.2.1.4 | 1.2.1.5 | 1.2.1.6 | 1.2.1.7 | 1.2.1.8 | 1.2.1.9 |
| 1.2.2.1 | 1.2.2.2 | 1.2.2.3 | 1.2.2.4 | 1.2.2.5 | 1.2.2.6 | 1.2.2.7 | 1.2.2.8 | 1.2.2.9 | 1.2.3.1 |
| 1.2.3.2 | 1.2.3.3 | 1.2.3.4 | 1.2.3.5 | 1.2.3.6 | 1.2.3.7 | 1.2.3.8 | 1.2.3.9 | 1.2.4.1 | 1.2.4.2 |
| 1.2.4.3 | 1.2.4.4 | 1.2.4.5 | 1.2.4.6 | 1.2.4.7 | 1.2.4.8 | 1.2.4.9 | 1.2.5.1 | 1.2.5.2 | 1.2.5.3 |
| 1.2.5.4 | 1.2.5.5 | 1.2.5.6 | 1.2.5.7 | 1.2.5.8 | 1.2.5.9 | 1.2.6.1 | 1.2.6.2 | 1.2.6.3 | 1.2.6.4 |
| 1.2.6.5 | 1.2.6.6 | 1.2.6.7 | 1.2.6.8 | 1.2.6.9 | 1.2.7.1 | 1.2.7.2 | 1.2.7.3 | 1.2.7.4 | 1.2.7.5 |
| 1.2.7.6 | 1.2.7.7 | 1.2.7.8 | 1.2.7.9 | 1.2.8.1 | 1.2.8.2 | 1.2.8.3 | 1.2.8.4 | 1.2.8.5 | 1.2.8.6 |
| 1.2.8.7 | 1.2.8.8 | 1.2.8.9 | 1.2.9.1 | 1.2.9.2 | 1.2.9.3 | 1.2.9.4 | 1.2.9.5 | 1.2.9.6 | 1.2.9.7 |
| 1.2.9.8 | 1.2.9.9 | 1.3.1.1 | 1.3.1.2 | 1.3.1.3 | 1.3.1.4 | 1.3.1.5 | 1.3.1.6 | 1.3.1.7 | 1.3.1.8 |
| 1.3.1.9 | 1.3.2.1 | 1.3.2.2 | 1.3.2.3 | 1.3.2.4 | 1.3.2.5 | 1.3.2.6 | 1.3.2.7 | 1.3.2.8 | 1.3.2.9 |
| 1.3.3.1 | 1.3.3.2 | 1.3.3.3 | 1.3.3.4 | 1.3.3.5 | 1.3.3.6 | 1.3.3.7 | 1.3.3.8 | 1.3.3.9 | 1.3.4.1 |
| 1.3.4.2 | 1.3.4.3 | 1.3.4.4 | 1.3.4.5 | 1.3.4.6 | 1.3.4.7 | 1.3.4.8 | 1.3.4.9 | 1.3.5.1 | 1.3.5.2 |
| 1.3.5.3 | 1.3.5.4 | 1.3.5.5 | 1.3.5.6 | 1.3.5.7 | 1.3.5.8 | 1.3.5.9 | 1.3.6.1 | 1.3.6.2 | 1.3.6.3 |
| 1.3.6.4 | 1.3.6.5 | 1.3.6.6 | 1.3.6.7 | 1.3.6.8 | 1.3.6.9 | 1.3.7.1 | 1.3.7.2 | 1.3.7.3 | 1.3.7.4 |
| 1.3.7.5 | 1.3.7.6 | 1.3.7.7 | 1.3.7.8 | 1.3.7.9 | 1.3.8.1 | 1.3.8.2 | 1.3.8.3 | 1.3.8.4 | 1.3.8.5 |
| 1.3.8.6 | 1.3.8.7 | 1.3.8.8 | 1.3.8.9 | 1.3.9.1 | 1.3.9.2 | 1.3.9.3 | 1.3.9.4 | 1.3.9.5 | 1.3.9.6 |
| 1.3.9.7 | 1.3.9.8 | 1.3.9.9 | 1.4.1.1 | 1.4.1.2 | 1.4.1.3 | 1.4.1.4 | 1.4.1.5 | 1.4.1.6 | 1.4.1.7 |
| 1.4.1.8 | 1.4.1.9 | 1.4.2.1 | 1.4.2.2 | 1.4.2.3 | 1.4.2.4 | 1.4.2.5 | 1.4.2.6 | 1.4.2.7 | 1.4.2.8 |
| 1.4.2.9 | 1.4.3.1 | 1.4.3.2 | 1.4.3.3 | 1.4.3.4 | 1.4.3.5 | 1.4.3.6 | 1.4.3.7 | 1.4.3.8 | 1.4.3.9 |
| 1.4.4.1 | 1.4.4.2 | 1.4.4.3 | 1.4.4.4 | 1.4.4.5 | 1.4.4.6 | 1.4.4.7 | 1.4.4.8 | 1.4.4.9 | 1.4.5.1 |
| 1.4.5.2 | 1.4.5.3 | 1.4.5.4 | 1.4.5.5 | 1.4.5.6 | 1.4.5.7 | 1.4.5.8 | 1.4.5.9 | 1.4.6.1 | 1.4.6.2 |
| 1.4.6.3 | 1.4.6.4 | 1.4.6.5 | 1.4.6.6 | 1.4.6.7 | 1.4.6.8 | 1.4.6.9 | 1.4.7.1 | 1.4.7.2 | 1.4.7.3 |
| 1.4.7.4 | 1.4.7.5 | 1.4.7.6 | 1.4.7.7 | 1.4.7.8 | 1.4.7.9 | 1.4.8.1 | 1.4.8.2 | 1.4.8.3 | 1.4.8.4 |
| 1.4.8.5 | 1.4.8.6 | 1.4.8.7 | 1.4.8.8 | 1.4.8.9 | 1.4.9.1 | 1.4.9.2 | 1.4.9.3 | 1.4.9.4 | 1.4.9.5 |
| 1.4.9.6 | 1.4.9.7 | 1.4.9.8 | 1.4.9.9 | 1.5.1.1 | 1.5.1.2 | 1.5.1.3 | 1.5.1.4 | 1.5.1.5 | 1.5.1.6 |
| 1.5.1.7 | 1.5.1.8 | 1.5.1.9 | 1.5.2.1 | 1.5.2.2 | 1.5.2.3 | 1.5.2.4 | 1.5.2.5 | 1.5.2.6 | 1.5.2.7 |
| 1.5.2.8 | 1.5.2.9 | 1.5.3.1 | 1.5.3.2 | 1.5.3.3 | 1.5.3.4 | 1.5.3.5 | 1.5.3.6 | 1.5.3.7 | 1.5.3.8 |
| 1.5.3.9 | 1.5.4.1 | 1.5.4.2 | 1.5.4.3 | 1.5.4.4 | 1.5.4.5 | 1.5.4.6 | 1.5.4.7 | 1.5.4.8 | 1.5.4.9 |
| 1.5.5.1 | 1.5.5.2 | 1.5.5.3 | 1.5.5.4 | 1.5.5.5 | 1.5.5.6 | 1.5.5.7 | 1.5.5.8 | 1.5.5.9 | 1.5.6.1 |
| 1.5.6.2 | 1.5.6.3 | 1.5.6.4 | 1.5.6.5 | 1.5.6.6 | 1.5.6.7 | 1.5.6.8 | 1.5.6.9 | 1.5.7.1 | 1.5.7.2 |
| 1.5.7.3 | 1.5.7.4 | 1.5.7.5 | 1.5.7.6 | 1.5.7.7 | 1.5.7.8 | 1.5.7.9 | 1.5.8.1 | 1.5.8.2 | 1.5.8.3 |
| 1.5.8.4 | 1.5.8.5 | 1.5.8.6 | 1.5.8.7 | 1.5.8.8 | 1.5.8.9 | 1.5.9.1 | 1.5.9.2 | 1.5.9.3 | 1.5.9.4 |
| 1.5.9.5 | 1.5.9.6 | 1.5.9.7 | 1.5.9.8 | 1.5.9.9 | 1.6.1.1 | 1.6.1.2 | 1.6.1.3 | 1.6.1.4 | 1.6.1.5 |
| 1.6.1.6 | 1.6.1.7 | 1.6.1.8 | 1.6.1.9 | 1.6.2.1 | 1.6.2.2 | 1.6.2.3 | 1.6.2.4 | 1.6.2.5 | 1.6.2.6 |
| 1.6.2.7 | 1.6.2.8 | 1.6.2.9 | 1.6.3.1 | 1.6.3.2 | 1.6.3.3 | 1.6.3.4 | 1.6.3.5 | 1.6.3.6 | 1.6.3.7 |
| 1.6.3.8 | 1.6.3.9 | 1.6.4.1 | 1.6.4.2 | 1.6.4.3 | 1.6.4.4 | 1.6.4.5 | 1.6.4.6 | 1.6.4.7 | 1.6.4.8 |
| 1.6.4.9 | 1.6.5.1 | 1.6.5.2 | 1.6.5.3 | 1.6.5.4 | 1.6.5.5 | 1.6.5.6 | 1.6.5.7 | 1.6.5.8 | 1.6.5.9 |
| 1.6.6.1 | 1.6.6.2 | 1.6.6.3 | 1.6.6.4 | 1.6.6.5 | 1.6.6.6 | 1.6.6.7 | 1.6.6.8 | 1.6.6.9 | 1.6.7.1 |
| 1.6.7.2 | 1.6.7.3 | 1.6.7.4 | 1.6.7.5 | 1.6.7.6 | 1.6.7.7 | 1.6.7.8 | 1.6.7.9 | 1.6.8.1 | 1.6.8.2 |
| 1.6.8.3 | 1.6.8.4 | 1.6.8.5 | 1.6.8.6 | 1.6.8.7 | 1.6.8.8 | 1.6.8.9 | 1.6.9.1 | 1.6.9.2 | 1.6.9.3 |
| 1.6.9.4 | 1.6.9.5 | 1.6.9.6 | 1.6.9.7 | 1.6.9.8 | 1.6.9.9 | 1.7.1.1 | 1.7.1.2 | 1.7.1.3 | 1.7.1.4 |
| 1.7.1.5 | 1.7.1.6 | 1.7.1.7 | 1.7.1.8 | 1.7.1.9 | 1.7.2.1 | 1.7.2.2 | 1.7.2.3 | 1.7.2.4 | 1.7.2.5 |
| 1.7.2.6 | 1.7.2.7 | 1.7.2.8 | 1.7.2.9 | 1.7.3.1 | 1.7.3.2 | 1.7.3.3 | 1.7.3.4 | 1.7.3.5 | 1.7.3.6 |
| 1.7.3.7 | 1.7.3.8 | 1.7.3.9 | 1.7.4.1 | 1.7.4.2 | 1.7.4.3 | 1.7.4.4 | 1.7.4.5 | 1.7.4.6 | 1.7.4.7 |
| 1.7.4.8 | 1.7.4.9 | 1.7.5.1 | 1.7.5.2 | 1.7.5.3 | 1.7.5.4 | 1.7.5.5 | 1.7.5.6 | 1.7.5.7 | 1.7.5.8 |
| 1.7.5.9 | 1.7.6.1 | 1.7.6.2 | 1.7.6.3 | 1.7.6.4 | 1.7.6.5 | 1.7.6.6 | 1.7.6.7 | 1.7.6.8 | 1.7.6.9 |
| 1.7.7.1 | 1.7.7.2 | 1.7.7.3 | 1.7.7.4 | 1.7.7.5 | 1.7.7.6 | 1.7.7.7 | 1.7.7.8 | 1.7.7.9 | 1.7.8.1 |
| 1.7.8.2 | 1.7.8.3 | 1.7.8.4 | 1.7.8.5 | 1.7.8.6 | 1.7.8.7 | 1.7.8.8 | 1.7.8.9 | 1.7.9.1 | 1.7.9.2 |
| 1.7.9.3 | 1.7.9.4 | 1.7.9.5 | 1.7.9.6 | 1.7.9.7 | 1.7.9.8 | 1.7.9.9 | 1.8.1.1 | 1.8.1.2 | 1.8.1.3 |
| 1.8.1.4 | 1.8.1.5 | 1.8.1.6 | 1.8.1.7 | 1.8.1.8 | 1.8.1.9 | 1.8.2.1 | 1.8.2.2 | 1.8.2.3 | 1.8.2.4 |
| 1.8.2.5 | 1.8.2.6 | 1.8.2.7 | 1.8.2.8 | 1.8.2.9 | 1.8.3.1 | 1.8.3.2 | 1.8.3.3 | 1.8.3.4 | 1.8.3.5 |
| 1.8.3.6 | 1.8.3.7 | 1.8.3.8 | 1.8.3.9 | 1.8.4.1 | 1.8.4.2 | 1.8.4.3 | 1.8.4.4 | 1.8.4.5 | 1.8.4.6 |
| 1.8.4.7 | 1.8.4.8 | 1.8.4.9 | 1.8.5.1 | 1.8.5.2 | 1.8.5.3 | 1.8.5.4 | 1.8.5.5 | 1.8.5.6 | 1.8.5.7 |
| 1.8.5.8 | 1.8.5.9 | 1.8.6.1 | 1.8.6.2 | 1.8.6.3 | 1.8.6.4 | 1.8.6.5 | 1.8.6.6 | 1.8.6.7 | 1.8.6.8 |
| 1.8.6.9 | 1.8.7.1 | 1.8.7.2 | 1.8.7.3 | 1.8.7.4 | 1.8.7.5 | 1.8.7.6 | 1.8.7.7 | 1.8.7.8 | 1.8.7.9 |
| 1.8.8.1 | 1.8.8.2 | 1.8.8.3 | 1.8.8.4 | 1.8.8.5 | 1.8.8.6 | 1.8.8.7 | 1.8.8.8 | 1.8.8.9 | 1.8.9.1 |
| 1.8.9.2 | 1.8.9.3 | 1.8.9.4 | 1.8.9.5 | 1.8.9.6 | 1.8.9.7 | 1.8.9.8 | 1.8.9.9 | 1.9.1.1 | 1.9.1.2 |
| 1.9.1.3 | 1.9.1.4 | 1.9.1.5 | 1.9.1.6 | 1.9.1.7 | 1.9.1.8 | 1.9.1.9 | 1.9.2.1 | 1.9.2.2 | 1.9.2.3 |
| 1.9.2.4 | 1.9.2.5 | 1.9.2.6 | 1.9.2.7 | 1.9.2.8 | 1.9.2.9 | 1.9.3.1 | 1.9.3.2 | 1.9.3.3 | 1.9.3.4 |
| 1.9.3.5 | 1.9.3.6 | 1.9.3.7 | 1.9.3.8 | 1.9.3.9 | 1.9.4.1 | 1.9.4.2 | 1.9.4.3 | 1.9.4.4 | 1.9.4.5 |
| 1.9.4.6 | 1.9.4.7 | 1.9.4.8 | 1.9.4.9 | 1.9.5.1 | 1.9.5.2 | 1.9.5.3 | 1.9.5.4 | 1.9.5.5 | 1.9.5.6 |
| 1.9.5.7 | 1.9.5.8 | 1.9.5.9 | 1.9.6.1 | 1.9.6.2 | 1.9.6.3 | 1.9.6.4 | 1.9.6.5 | 1.9.6.6 | 1.9.6.7 |
| 1.9.6.8 | 1.9.6.9 | 1.9.7.1 | 1.9.7.2 | 1.9.7.3 | 1.9.7.4 | 1.9.7.5 | 1.9.7.6 | 1.9.7.7 | 1.9.7.8 |
| 1.9.7.9 | 1.9.8.1 | 1.9.8.2 | 1.9.8.3 | 1.9.8.4 | 1.9.8.5 | 1.9.8.6 | 1.9.8.7 | 1.9.8.8 | 1.9.8.9 |
| 1.9.9.1 | 1.9.9.2 | 1.9.9.3 | 1.9.9.4 | 1.9.9.5 | 1.9.9.6 | 1.9.9.7 | 1.9.9.8 | 1.9.9.9 | 2.1.1.1 |
| 2.1.1.2 | 2.1.1.3 | 2.1.1.4 | 2.1.1.5 | 2.1.1.6 | 2.1.1.7 | 2.1.1.8 | 2.1.1.9 | 2.1.2.1 | 2.1.2.2 |
| 2.1.2.3 | 2.1.2.4 | 2.1.2.5 | 2.1.2.6 | 2.1.2.7 | 2.1.2.8 | 2.1.2.9 | 2.1.3.1 | 2.1.3.2 | 2.1.3.3 |
| 2.1.3.4 | 2.1.3.5 | 2.1.3.6 | 2.1.3.7 | 2.1.3.8 | 2.1.3.9 | 2.1.4.1 | 2.1.4.2 | 2.1.4.3 | 2.1.4.4 |
| 2.1.4.5 | 2.1.4.6 | 2.1.4.7 | 2.1.4.8 | 2.1.4.9 | 2.1.5.1 | 2.1.5.2 | 2.1.5.3 | 2.1.5.4 | 2.1.5.5 |
| 2.1.5.6 | 2.1.5.7 | 2.1.5.8 | 2.1.5.9 | 2.1.6.1 | 2.1.6.2 | 2.1.6.3 | 2.1.6.4 | 2.1.6.5 | 2.1.6.6 |
| 2.1.6.7 | 2.1.6.8 | 2.1.6.9 | 2.1.7.1 | 2.1.7.2 | 2.1.7.3 | 2.1.7.4 | 2.1.7.5 | 2.1.7.6 | 2.1.7.7 |

TABLE 1-continued

| | | | | | | | | | |
|---|---|---|---|---|---|---|---|---|---|
| 2.1.7.8 | 2.1.7.9 | 2.1.8.1 | 2.1.8.2 | 2.1.8.3 | 2.1.8.4 | 2.1.8.5 | 2.1.8.6 | 2.1.8.7 | 2.1.8.8 |
| 2.1.8.9 | 2.1.9.1 | 2.1.9.2 | 2.1.9.3 | 2.1.9.4 | 2.1.9.5 | 2.1.9.6 | 2.1.9.7 | 2.1.9.8 | 2.1.9.9 |
| 2.2.1.1 | 2.2.1.2 | 2.2.1.3 | 2.2.1.4 | 2.2.1.5 | 2.2.1.6 | 2.2.1.7 | 2.2.1.8 | 2.2.1.9 | 2.2.2.1 |
| 2.2.2.2 | 2.2.2.3 | 2.2.2.4 | 2.2.2.5 | 2.2.2.6 | 2.2.2.7 | 2.2.2.8 | 2.2.2.9 | 2.2.3.1 | 2.2.3.2 |
| 2.2.3.3 | 2.2.3.4 | 2.2.3.5 | 2.2.3.6 | 2.2.3.7 | 2.2.3.8 | 2.2.3.9 | 2.2.4.1 | 2.2.4.2 | 2.2.4.3 |
| 2.2.4.4 | 2.2.4.5 | 2.2.4.6 | 2.2.4.7 | 2.2.4.8 | 2.2.4.9 | 2.2.5.1 | 2.2.5.2 | 2.2.5.3 | 2.2.5.4 |
| 2.2.5.5 | 2.2.5.6 | 2.2.5.7 | 2.2.5.8 | 2.2.5.9 | 2.2.6.1 | 2.2.6.2 | 2.2.6.3 | 2.2.6.4 | 2.2.6.5 |
| 2.2.6.6 | 2.2.6.7 | 2.2.6.8 | 2.2.6.9 | 2.2.7.1 | 2.2.7.2 | 2.2.7.3 | 2.2.7.4 | 2.2.7.5 | 2.2.7.6 |
| 2.2.7.7 | 2.2.7.8 | 2.2.7.9 | 2.2.8.1 | 2.2.8.2 | 2.2.8.3 | 2.2.8.4 | 2.2.8.5 | 2.2.8.6 | 2.2.8.7 |
| 2.2.8.8 | 2.2.8.9 | 2.2.9.1 | 2.2.9.2 | 2.2.9.3 | 2.2.9.4 | 2.2.9.5 | 2.2.9.6 | 2.2.9.7 | 2.2.9.8 |
| 2.2.9.9 | 2.3.1.1 | 2.3.1.2 | 2.3.1.3 | 2.3.1.4 | 2.3.1.5 | 2.3.1.6 | 2.3.1.7 | 2.3.1.8 | 2.3.1.9 |
| 2.3.2.1 | 2.3.2.2 | 2.3.2.3 | 2.3.2.4 | 2.3.2.5 | 2.3.2.6 | 2.3.2.7 | 2.3.2.8 | 2.3.2.9 | 2.3.3.1 |
| 2.3.3.2 | 2.3.3.3 | 2.3.3.4 | 2.3.3.5 | 2.3.3.6 | 2.3.3.7 | 2.3.3.8 | 2.3.3.9 | 2.3.4.1 | 2.3.4.2 |
| 2.3.4.3 | 2.3.4.4 | 2.3.4.5 | 2.3.4.6 | 2.3.4.7 | 2.3.4.8 | 2.3.4.9 | 2.3.5.1 | 2.3.5.2 | 2.3.5.3 |
| 2.3.5.4 | 2.3.5.5 | 2.3.5.6 | 2.3.5.7 | 2.3.5.8 | 2.3.5.9 | 2.3.6.1 | 2.3.6.2 | 2.3.6.3 | 2.3.6.4 |
| 2.3.6.5 | 2.3.6.6 | 2.3.6.7 | 2.3.6.8 | 2.3.6.9 | 2.3.7.1 | 2.3.7.2 | 2.3.7.3 | 2.3.7.4 | 2.3.7.5 |
| 2.3.7.6 | 2.3.7.7 | 2.3.7.8 | 2.3.7.9 | 2.3.8.1 | 2.3.8.2 | 2.3.8.3 | 2.3.8.4 | 2.3.8.5 | 2.3.8.6 |
| 2.3.8.7 | 2.3.8.8 | 2.3.8.9 | 2.3.9.1 | 2.3.9.2 | 2.3.9.3 | 2.3.9.4 | 2.3.9.5 | 2.3.9.6 | 2.3.9.7 |
| 2.3.9.8 | 2.3.9.9 | 2.4.1.1 | 2.4.1.2 | 2.4.1.3 | 2.4.1.4 | 2.4.1.5 | 2.4.1.6 | 2.4.1.7 | 2.4.1.8 |
| 2.4.1.9 | 2.4.2.1 | 2.4.2.2 | 2.4.2.3 | 2.4.2.4 | 2.4.2.5 | 2.4.2.6 | 2.4.2.7 | 2.4.2.8 | 2.4.2.9 |
| 2.4.3.1 | 2.4.3.2 | 2.4.3.3 | 2.4.3.4 | 2.4.3.5 | 2.4.3.6 | 2.4.3.7 | 2.4.3.8 | 2.4.3.9 | 2.4.4.1 |
| 2.4.4.2 | 2.4.4.3 | 2.4.4.4 | 2.4.4.5 | 2.4.4.6 | 2.4.4.7 | 2.4.4.8 | 2.4.4.9 | 2.4.5.1 | 2.4.5.2 |
| 2.4.5.3 | 2.4.5.4 | 2.4.5.5 | 2.4.5.6 | 2.4.5.7 | 2.4.5.8 | 2.4.5.9 | 2.4.6.1 | 2.4.6.2 | 2.4.6.3 |
| 2.4.6.4 | 2.4.6.5 | 2.4.6.6 | 2.4.6.7 | 2.4.6.8 | 2.4.6.9 | 2.4.7.1 | 2.4.7.2 | 2.4.7.3 | 2.4.7.4 |
| 2.4.7.5 | 2.4.7.6 | 2.4.7.7 | 2.4.7.8 | 2.4.7.9 | 2.4.8.1 | 2.4.8.2 | 2.4.8.3 | 2.4.8.4 | 2.4.8.5 |
| 2.4.8.6 | 2.4.8.7 | 2.4.8.8 | 2.4.8.9 | 2.4.9.1 | 2.4.9.2 | 2.4.9.3 | 2.4.9.4 | 2.4.9.5 | 2.4.9.6 |
| 2.4.9.7 | 2.4.9.8 | 2.4.9.9 | 2.5.1.1 | 2.5.1.2 | 2.5.1.3 | 2.5.1.4 | 2.5.1.5 | 2.5.1.6 | 2.5.1.7 |
| 2.5.1.8 | 2.5.1.9 | 2.5.2.1 | 2.5.2.2 | 2.5.2.3 | 2.5.2.4 | 2.5.2.5 | 2.5.2.6 | 2.5.2.7 | 2.5.2.8 |
| 2.5.2.9 | 2.5.3.1 | 2.5.3.2 | 2.5.3.3 | 2.5.3.4 | 2.5.3.5 | 2.5.3.6 | 2.5.3.7 | 2.5.3.8 | 2.5.3.9 |
| 2.5.4.1 | 2.5.4.2 | 2.5.4.3 | 2.5.4.4 | 2.5.4.5 | 2.5.4.6 | 2.5.4.7 | 2.5.4.8 | 2.5.4.9 | 2.5.5.1 |
| 2.5.5.2 | 2.5.5.3 | 2.5.5.4 | 2.5.5.5 | 2.5.5.6 | 2.5.5.7 | 2.5.5.8 | 2.5.5.9 | 2.5.6.1 | 2.5.6.2 |
| 2.5.6.3 | 2.5.6.4 | 2.5.6.5 | 2.5.6.6 | 2.5.6.7 | 2.5.6.8 | 2.5.6.9 | 2.5.7.1 | 2.5.7.2 | 2.5.7.3 |
| 2.5.7.4 | 2.5.7.5 | 2.5.7.6 | 2.5.7.7 | 2.5.7.8 | 2.5.7.9 | 2.5.8.1 | 2.5.8.2 | 2.5.8.3 | 2.5.8.4 |
| 2.5.8.5 | 2.5.8.6 | 2.5.8.7 | 2.5.8.8 | 2.5.8.9 | 2.5.9.1 | 2.5.9.2 | 2.5.9.3 | 2.5.9.4 | 2.5.9.5 |
| 2.5.9.6 | 2.5.9.7 | 2.5.9.8 | 2.5.9.9 | 2.6.1.1 | 2.6.1.2 | 2.6.1.3 | 2.6.1.4 | 2.6.1.5 | 2.6.1.6 |
| 2.6.1.7 | 2.6.1.8 | 2.6.1.9 | 2.6.2.1 | 2.6.2.2 | 2.6.2.3 | 2.6.2.4 | 2.6.2.5 | 2.6.2.6 | 2.6.2.7 |
| 2.6.2.8 | 2.6.2.9 | 2.6.3.1 | 2.6.3.2 | 2.6.3.3 | 2.6.3.4 | 2.6.3.5 | 2.6.3.6 | 2.6.3.7 | 2.6.3.8 |
| 2.6.3.9 | 2.6.4.1 | 2.6.4.2 | 2.6.4.3 | 2.6.4.4 | 2.6.4.5 | 2.6.4.6 | 2.6.4.7 | 2.6.4.8 | 2.6.4.9 |
| 2.6.5.1 | 2.6.5.2 | 2.6.5.3 | 2.6.5.4 | 2.6.5.5 | 2.6.5.6 | 2.6.5.7 | 2.6.5.8 | 2.6.5.9 | 2.6.6.1 |
| 2.6.6.2 | 2.6.6.3 | 2.6.6.4 | 2.6.6.5 | 2.6.6.6 | 2.6.6.7 | 2.6.6.8 | 2.6.6.9 | 2.6.7.1 | 2.6.7.2 |
| 2.6.7.3 | 2.6.7.4 | 2.6.7.5 | 2.6.7.6 | 2.6.7.7 | 2.6.7.8 | 2.6.7.9 | 2.6.8.1 | 2.6.8.2 | 2.6.8.3 |
| 2.6.8.4 | 2.6.8.5 | 2.6.8.6 | 2.6.8.7 | 2.6.8.8 | 2.6.8.9 | 2.6.9.1 | 2.6.9.2 | 2.6.9.3 | 2.6.9.4 |
| 2.6.9.5 | 2.6.9.6 | 2.6.9.7 | 2.6.9.8 | 2.6.9.9 | 2.7.1.1 | 2.7.1.2 | 2.7.1.3 | 2.7.1.4 | 2.7.1.5 |
| 2.7.1.6 | 2.7.1.7 | 2.7.1.8 | 2.7.1.9 | 2.7.2.1 | 2.7.2.2 | 2.7.2.3 | 2.7.2.4 | 2.7.2.5 | 2.7.2.6 |
| 2.7.2.7 | 2.7.2.8 | 2.7.2.9 | 2.7.3.1 | 2.7.3.2 | 2.7.3.3 | 2.7.3.4 | 2.7.3.5 | 2.7.3.6 | 2.7.3.7 |
| 2.7.3.8 | 2.7.3.9 | 2.7.4.1 | 2.7.4.2 | 2.7.4.3 | 2.7.4.4 | 2.7.4.5 | 2.7.4.6 | 2.7.4.7 | 2.7.4.8 |
| 2.7.4.9 | 2.7.5.1 | 2.7.5.2 | 2.7.5.3 | 2.7.5.4 | 2.7.5.5 | 2.7.5.6 | 2.7.5.7 | 2.7.5.8 | 2.7.5.9 |
| 2.7.6.1 | 2.7.6.2 | 2.7.6.3 | 2.7.6.4 | 2.7.6.5 | 2.7.6.6 | 2.7.6.7 | 2.7.6.8 | 2.7.6.9 | 2.7.7.1 |
| 2.7.7.2 | 2.7.7.3 | 2.7.7.4 | 2.7.7.5 | 2.7.7.6 | 2.7.7.7 | 2.7.7.8 | 2.7.7.9 | 2.7.8.1 | 2.7.8.2 |
| 2.7.8.3 | 2.7.8.4 | 2.7.8.5 | 2.7.8.6 | 2.7.8.7 | 2.7.8.8 | 2.7.8.9 | 2.7.9.1 | 2.7.9.2 | 2.7.9.3 |
| 2.7.9.4 | 2.7.9.5 | 2.7.9.6 | 2.7.9.7 | 2.7.9.8 | 2.7.9.9 | 2.8.1.1 | 2.8.1.2 | 2.8.1.3 | 2.8.1.4 |
| 2.8.1.5 | 2.8.1.6 | 2.8.1.7 | 2.8.1.8 | 2.8.1.9 | 2.8.2.1 | 2.8.2.2 | 2.8.2.3 | 2.8.2.4 | 2.8.2.5 |
| 2.8.2.6 | 2.8.2.7 | 2.8.2.8 | 2.8.2.9 | 2.8.3.1 | 2.8.3.2 | 2.8.3.3 | 2.8.3.4 | 2.8.3.5 | 2.8.3.6 |
| 2.8.3.7 | 2.8.3.8 | 2.8.3.9 | 2.8.4.1 | 2.8.4.2 | 2.8.4.3 | 2.8.4.4 | 2.8.4.5 | 2.8.4.6 | 2.8.4.7 |
| 2.8.4.8 | 2.8.4.9 | 2.8.5.1 | 2.8.5.2 | 2.8.5.3 | 2.8.5.4 | 2.8.5.5 | 2.8.5.6 | 2.8.5.7 | 2.8.5.8 |
| 2.8.5.9 | 2.8.6.1 | 2.8.6.2 | 2.8.6.3 | 2.8.6.4 | 2.8.6.5 | 2.8.6.6 | 2.8.6.7 | 2.8.6.8 | 2.8.6.9 |
| 2.8.7.1 | 2.8.7.2 | 2.8.7.3 | 2.8.7.4 | 2.8.7.5 | 2.8.7.6 | 2.8.7.7 | 2.8.7.8 | 2.8.7.9 | 2.8.8.1 |
| 2.8.8.2 | 2.8.8.3 | 2.8.8.4 | 2.8.8.5 | 2.8.8.6 | 2.8.8.7 | 2.8.8.8 | 2.8.8.9 | 2.8.9.1 | 2.8.9.2 |
| 2.8.9.3 | 2.8.9.4 | 2.8.9.5 | 2.8.9.6 | 2.8.9.7 | 2.8.9.8 | 2.8.9.9 | 2.9.1.1 | 2.9.1.2 | 2.9.1.3 |
| 2.9.1.4 | 2.9.1.5 | 2.9.1.6 | 2.9.1.7 | 2.9.1.8 | 2.9.1.9 | 2.9.2.1 | 2.9.2.2 | 2.9.2.3 | 2.9.2.4 |
| 2.9.2.5 | 2.9.2.6 | 2.9.2.7 | 2.9.2.8 | 2.9.2.9 | 2.9.3.1 | 2.9.3.2 | 2.9.3.3 | 2.9.3.4 | 2.9.3.5 |
| 2.9.3.6 | 2.9.3.7 | 2.9.3.8 | 2.9.3.9 | 2.9.4.1 | 2.9.4.2 | 2.9.4.3 | 2.9.4.4 | 2.9.4.5 | 2.9.4.6 |
| 2.9.4.7 | 2.9.4.8 | 2.9.4.9 | 2.9.5.1 | 2.9.5.2 | 2.9.5.3 | 2.9.5.4 | 2.9.5.5 | 2.9.5.6 | 2.9.5.7 |
| 2.9.5.8 | 2.9.5.9 | 2.9.6.1 | 2.9.6.2 | 2.9.6.3 | 2.9.6.4 | 2.9.6.5 | 2.9.6.6 | 2.9.6.7 | 2.9.6.8 |
| 2.9.6.9 | 2.9.7.1 | 2.9.7.2 | 2.9.7.3 | 2.9.7.4 | 2.9.7.5 | 2.9.7.6 | 2.9.7.7 | 2.9.7.8 | 2.9.7.9 |
| 2.9.8.1 | 2.9.8.2 | 2.9.8.3 | 2.9.8.4 | 2.9.8.5 | 2.9.8.6 | 2.9.8.7 | 2.9.8.8 | 2.9.8.9 | 2.9.9.1 |
| 2.9.9.2 | 2.9.9.3 | 2.9.9.4 | 2.9.9.5 | 2.9.9.6 | 2.9.9.7 | 2.9.9.8 | 2.9.9.9 | 3.1.1.1 | 3.1.1.2 |
| 3.1.1.3 | 3.1.1.4 | 3.1.1.5 | 3.1.1.6 | 3.1.1.7 | 3.1.1.8 | 3.1.1.9 | 3.1.2.1 | 3.1.2.2 | 3.1.2.3 |
| 3.1.2.4 | 3.1.2.5 | 3.1.2.6 | 3.1.2.7 | 3.1.2.8 | 3.1.2.9 | 3.1.3.1 | 3.1.3.2 | 3.1.3.3 | 3.1.3.4 |
| 3.1.3.5 | 3.1.3.6 | 3.1.3.7 | 3.1.3.8 | 3.1.3.9 | 3.1.4.1 | 3.1.4.2 | 3.1.4.3 | 3.1.4.4 | 3.1.4.5 |
| 3.1.4.6 | 3.1.4.7 | 3.1.4.8 | 3.1.4.9 | 3.1.5.1 | 3.1.5.2 | 3.1.5.3 | 3.1.5.4 | 3.1.5.5 | 3.1.5.6 |
| 3.1.5.7 | 3.1.5.8 | 3.1.5.9 | 3.1.6.1 | 3.1.6.2 | 3.1.6.3 | 3.1.6.4 | 3.1.6.5 | 3.1.6.6 | 3.1.6.7 |
| 3.1.6.8 | 3.1.6.9 | 3.1.7.1 | 3.1.7.2 | 3.1.7.3 | 3.1.7.4 | 3.1.7.5 | 3.1.7.6 | 3.1.7.7 | 3.1.7.8 |
| 3.1.7.9 | 3.1.8.1 | 3.1.8.2 | 3.1.8.3 | 3.1.8.4 | 3.1.8.5 | 3.1.8.6 | 3.1.8.7 | 3.1.8.8 | 3.1.8.9 |
| 3.1.9.1 | 3.1.9.2 | 3.1.9.3 | 3.1.9.4 | 3.1.9.5 | 3.1.9.6 | 3.1.9.7 | 3.1.9.8 | 3.1.9.9 | 3.2.1.1 |
| 3.2.1.2 | 3.2.1.3 | 3.2.1.4 | 3.2.1.5 | 3.2.1.6 | 3.2.1.7 | 3.2.1.8 | 3.2.1.9 | 3.2.2.1 | 3.2.2.2 |
| 3.2.2.3 | 3.2.2.4 | 3.2.2.5 | 3.2.2.6 | 3.2.2.7 | 3.2.2.8 | 3.2.2.9 | 3.2.3.1 | 3.2.3.2 | 3.2.3.3 |
| 3.2.3.4 | 3.2.3.5 | 3.2.3.6 | 3.2.3.7 | 3.2.3.8 | 3.2.3.9 | 3.2.4.1 | 3.2.4.2 | 3.2.4.3 | 3.2.4.4 |
| 3.2.4.5 | 3.2.4.6 | 3.2.4.7 | 3.2.4.8 | 3.2.4.9 | 3.2.5.1 | 3.2.5.2 | 3.2.5.3 | 3.2.5.4 | 3.2.5.5 |

TABLE 1-continued

| | | | | | | | | | |
|---|---|---|---|---|---|---|---|---|---|
| 3.2.5.6 | 3.2.5.7 | 3.2.5.8 | 3.2.5.9 | 3.2.6.1 | 3.2.6.2 | 3.2.6.3 | 3.2.6.4 | 3.2.6.5 | 3.2.6.6 |
| 3.2.6.7 | 3.2.6.8 | 3.2.6.9 | 3.2.7.1 | 3.2.7.2 | 3.2.7.3 | 3.2.7.4 | 3.2.7.5 | 3.2.7.6 | 3.2.7.7 |
| 3.2.7.8 | 3.2.7.9 | 3.2.8.1 | 3.2.8.2 | 3.2.8.3 | 3.2.8.4 | 3.2.8.5 | 3.2.8.6 | 3.2.8.7 | 3.2.8.8 |
| 3.2.8.9 | 3.2.9.1 | 3.2.9.2 | 3.2.9.3 | 3.2.9.4 | 3.2.9.5 | 3.2.9.6 | 3.2.9.7 | 3.2.9.8 | 3.2.9.9 |
| 3.3.1.1 | 3.3.1.2 | 3.3.1.3 | 3.3.1.4 | 3.3.1.5 | 3.3.1.6 | 3.3.1.7 | 3.3.1.8 | 3.3.1.9 | 3.3.2.1 |
| 3.3.2.2 | 3.3.2.3 | 3.3.2.4 | 3.3.2.5 | 3.3.2.6 | 3.3.2.7 | 3.3.2.8 | 3.3.2.9 | 3.3.3.1 | 3.3.3.2 |
| 3.3.3.3 | 3.3.3.4 | 3.3.3.5 | 3.3.3.6 | 3.3.3.7 | 3.3.3.8 | 3.3.3.9 | 3.3.4.1 | 3.3.4.2 | 3.3.4.3 |
| 3.3.4.4 | 3.3.4.5 | 3.3.4.6 | 3.3.4.7 | 3.3.4.8 | 3.3.4.9 | 3.3.5.1 | 3.3.5.2 | 3.3.5.3 | 3.3.5.4 |
| 3.3.5.5 | 3.3.5.6 | 3.3.5.7 | 3.3.5.8 | 3.3.5.9 | 3.3.6.1 | 3.3.6.2 | 3.3.6.3 | 3.3.6.4 | 3.3.6.5 |
| 3.3.6.6 | 3.3.6.7 | 3.3.6.8 | 3.3.6.9 | 3.3.7.1 | 3.3.7.2 | 3.3.7.3 | 3.3.7.4 | 3.3.7.5 | 3.3.7.6 |
| 3.3.7.7 | 3.3.7.8 | 3.3.7.9 | 3.3.8.1 | 3.3.8.2 | 3.3.8.3 | 3.3.8.4 | 3.3.8.5 | 3.3.8.6 | 3.3.8.7 |
| 3.3.8.8 | 3.3.8.9 | 3.3.9.1 | 3.3.9.2 | 3.3.9.3 | 3.3.9.4 | 3.3.9.5 | 3.3.9.6 | 3.3.9.7 | 3.3.9.8 |
| 3.3.9.9 | 3.4.1.1 | 3.4.1.2 | 3.4.1.3 | 3.4.1.4 | 3.4.1.5 | 3.4.1.6 | 3.4.1.7 | 3.4.1.8 | 3.4.1.9 |
| 3.4.2.1 | 3.4.2.2 | 3.4.2.3 | 3.4.2.4 | 3.4.2.5 | 3.4.2.6 | 3.4.2.7 | 3.4.2.8 | 3.4.2.9 | 3.4.3.1 |
| 3.4.3.2 | 3.4.3.3 | 3.4.3.4 | 3.4.3.5 | 3.4.3.6 | 3.4.3.7 | 3.4.3.8 | 3.4.3.9 | 3.4.1.1 | 3.4.4.2 |
| 3.4.4.3 | 3.4.4.4 | 3.4.4.5 | 3.4.4.6 | 3.4.4.7 | 3.4.4.8 | 3.4.4.9 | 3.4.5.1 | 3.4.5.2 | 3.4.5.3 |
| 3.4.5.4 | 3.4.5.5 | 3.4.5.6 | 3.4.5.7 | 3.4.5.8 | 3.4.5.9 | 3.4.6.1 | 3.4.6.2 | 3.4.6.3 | 3.4.6.4 |
| 3.4.6.5 | 3.4.6.6 | 3.4.6.7 | 3.4.6.8 | 3.4.6.9 | 3.4.7.1 | 3.4.7.2 | 3.4.7.3 | 3.4.7.4 | 3.4.7.5 |
| 3.4.7.6 | 3.4.7.7 | 3.4.7.8 | 3.4.7.9 | 3.4.8.1 | 3.4.8.2 | 3.4.8.3 | 3.4.8.4 | 3.4.8.5 | 3.4.8.6 |
| 3.4.8.7 | 3.4.8.8 | 3.4.8.9 | 3.4.9.1 | 3.4.9.2 | 3.4.9.3 | 3.4.9.4 | 3.4.9.5 | 3.4.9.6 | 3.4.9.7 |
| 3.4.9.8 | 3.4.9.9 | 3.5.1.1 | 3.5.1.2 | 3.5.1.3 | 3.5.1.4 | 3.5.1.5 | 3.5.1.6 | 3.5.1.7 | 3.5.1.8 |
| 3.5.1.9 | 3.5.2.1 | 3.5.2.2 | 3.5.2.3 | 3.5.2.4 | 3.5.2.5 | 3.5.2.6 | 3.5.2.7 | 3.5.2.8 | 3.5.2.9 |
| 3.5.3.1 | 3.5.3.2 | 3.5.3.3 | 3.5.3.4 | 3.5.3.5 | 3.5.3.6 | 3.5.3.7 | 3.5.3.8 | 3.5.3.9 | 3.5.4.1 |
| 3.5.4.2 | 3.5.4.3 | 3.5.4.4 | 3.5.4.5 | 3.5.4.6 | 3.5.4.7 | 3.5.4.8 | 3.5.4.9 | 3.5.5.1 | 3.5.5.2 |
| 3.5.5.3 | 3.5.5.4 | 3.5.5.5 | 3.5.5.6 | 3.5.5.7 | 3.5.5.8 | 3.5.5.9 | 3.5.6.1 | 3.5.6.2 | 3.5.6.3 |
| 3.5.6.4 | 3.5.6.5 | 3.5.6.6 | 3.5.6.7 | 3.5.6.8 | 3.5.6.9 | 3.5.7.1 | 3.5.7.2 | 3.5.7.3 | 3.5.7.4 |
| 3.5.7.5 | 3.5.7.6 | 3.5.7.7 | 3.5.7.8 | 3.5.7.9 | 3.5.8.1 | 3.5.8.2 | 3.5.8.3 | 3.5.8.4 | 3.5.8.5 |
| 3.5.8.6 | 3.5.8.7 | 3.5.8.8 | 3.5.8.9 | 3.5.9.1 | 3.5.9.2 | 3.5.9.3 | 3.5.9.4 | 3.5.9.5 | 3.5.9.6 |
| 3.5.9.7 | 3.5.9.8 | 3.5.9.9 | 3.6.1.1 | 3.6.1.2 | 3.6.1.3 | 3.6.1.4 | 3.6.1.5 | 3.6.1.6 | 3.6.1.7 |
| 3.6.1.8 | 3.6.1.9 | 3.6.2.1 | 3.6.2.2 | 3.6.2.3 | 3.6.2.4 | 3.6.2.5 | 3.6.2.6 | 3.6.2.7 | 3.6.2.8 |
| 3.6.2.9 | 3.6.3.1 | 3.6.3.2 | 3.6.3.3 | 3.6.3.4 | 3.6.3.5 | 3.6.3.6 | 3.6.3.7 | 3.6.3.8 | 3.6.3.9 |
| 3.6.4.1 | 3.6.4.2 | 3.6.4.3 | 3.6.4.4 | 3.6.4.5 | 3.6.4.6 | 3.6.4.7 | 3.6.4.8 | 3.6.4.9 | 3.6.5.1 |
| 3.6.5.2 | 3.6.5.3 | 3.6.5.4 | 3.6.5.5 | 3.6.5.6 | 3.6.5.7 | 3.6.5.8 | 3.6.5.9 | 3.6.6.1 | 3.6.6.2 |
| 3.6.6.3 | 3.6.6.4 | 3.6.6.5 | 3.6.6.6 | 3.6.6.7 | 3.6.6.8 | 3.6.6.9 | 3.6.7.1 | 3.6.7.2 | 3.6.7.3 |
| 3.6.7.4 | 3.6.7.5 | 3.6.7.6 | 3.6.7.7 | 3.6.7.8 | 3.6.7.9 | 3.6.8.1 | 3.6.8.2 | 3.6.8.3 | 3.6.8.4 |
| 3.6.8.5 | 3.6.8.6 | 3.6.8.7 | 3.6.8.8 | 3.6.8.9 | 3.6.9.1 | 3.6.9.2 | 3.6.9.3 | 3.6.9.4 | 3.6.9.5 |
| 3.6.9.6 | 3.6.9.7 | 3.6.9.8 | 3.6.9.9 | 3.7.1.1 | 3.7.1.2 | 3.7.1.3 | 3.7.1.4 | 3.7.1.5 | 3.7.1.6 |
| 3.7.1.7 | 3.7.1.8 | 3.7.1.9 | 3.7.2.1 | 3.7.2.2 | 3.7.2.3 | 3.7.2.4 | 3.7.2.5 | 3.7.2.6 | 3.7.2.7 |
| 3.7.2.8 | 3.7.2.9 | 3.7.3.1 | 3.7.3.2 | 3.7.3.3 | 3.7.3.4 | 3.7.3.5 | 3.7.3.6 | 3.7.3.7 | 3.7.3.8 |
| 3.7.3.9 | 3.7.4.1 | 3.7.4.2 | 3.7.4.3 | 3.7.4.4 | 3.7.4.5 | 3.7.4.6 | 3.7.4.7 | 3.7.4.8 | 3.7.4.9 |
| 3.7.5.1 | 3.7.5.2 | 3.7.5.3 | 3.7.5.4 | 3.7.5.5 | 3.7.5.6 | 3.7.5.7 | 3.7.5.8 | 3.7.5.9 | 3.7.6.1 |
| 3.7.6.2 | 3.7.6.3 | 3.7.6.4 | 3.7.6.5 | 3.7.6.6 | 3.7.6.7 | 3.7.6.8 | 3.7.6.9 | 3.7.7.1 | 3.7.7.2 |
| 3.7.7.3 | 3.7.7.4 | 3.7.7.5 | 3.7.7.6 | 3.7.7.7 | 3.7.7.8 | 3.7.7.9 | 3.7.8.1 | 3.7.8.2 | 3.7.8.3 |
| 3.7.8.4 | 3.7.8.5 | 3.7.8.6 | 3.7.8.7 | 3.7.8.8 | 3.7.8.9 | 3.7.9.1 | 3.7.9.2 | 3.7.9.3 | 3.7.9.4 |
| 3.7.9.5 | 3.7.9.6 | 3.7.9.7 | 3.7.9.8 | 3.7.9.9 | 3.8.1.1 | 3.8.1.2 | 3.8.1.3 | 3.8.1.4 | 3.8.1.5 |
| 3.8.1.6 | 3.8.1.7 | 3.8.1.8 | 3.8.1.9 | 3.8.2.1 | 3.8.2.2 | 3.8.2.3 | 3.8.2.4 | 3.8.2.5 | 3.8.2.6 |
| 3.8.2.7 | 3.8.2.8 | 3.8.2.9 | 3.8.3.1 | 3.8.3.2 | 3.8.3.3 | 3.8.3.4 | 3.8.3.5 | 3.8.3.6 | 3.8.3.7 |
| 3.8.3.8 | 3.8.3.9 | 3.8.4.1 | 3.8.4.2 | 3.8.4.3 | 3.8.4.4 | 3.8.4.5 | 3.8.4.6 | 3.8.4.7 | 3.8.4.8 |
| 3.8.4.9 | 3.8.5.1 | 3.8.5.2 | 3.8.5.3 | 3.8.5.4 | 3.8.5.5 | 3.8.5.6 | 3.8.5.7 | 3.8.5.8 | 3.8.5.9 |
| 3.8.6.1 | 3.8.6.2 | 3.8.6.3 | 3.8.6.4 | 3.8.6.5 | 3.8.6.6 | 3.8.6.7 | 3.8.6.8 | 3.8.6.9 | 3.8.7.1 |
| 3.8.7.2 | 3.8.7.3 | 3.8.7.4 | 3.8.7.5 | 3.8.7.6 | 3.8.7.7 | 3.8.7.8 | 3.8.7.9 | 3.8.8.1 | 3.8.8.2 |
| 3.8.8.3 | 3.8.8.4 | 3.8.8.5 | 3.8.8.6 | 3.8.8.7 | 3.8.8.8 | 3.8.8.9 | 3.8.9.1 | 3.8.9.2 | 3.8.9.3 |
| 3.8.9.4 | 3.8.9.5 | 3.8.9.6 | 3.8.9.7 | 3.8.9.8 | 3.8.9.9 | 3.9.1.1 | 3.9.1.2 | 3.9.1.3 | 3.9.1.4 |
| 3.9.1.5 | 3.9.1.6 | 3.9.1.7 | 3.9.1.8 | 3.9.1.9 | 3.9.2.1 | 3.9.2.2 | 3.9.2.3 | 3.9.2.4 | 3.9.2.5 |
| 3.9.2.6 | 3.9.2.7 | 3.9.2.8 | 3.9.2.9 | 3.9.3.1 | 3.9.3.2 | 3.9.3.3 | 3.9.3.4 | 3.9.3.5 | 3.9.3.6 |
| 3.9.3.7 | 3.9.3.8 | 3.9.3.9 | 3.9.4.1 | 3.9.4.2 | 3.9.4.3 | 3.9.4.4 | 3.9.4.5 | 3.9.4.6 | 3.9.4.7 |
| 3.9.4.8 | 3.9.4.9 | 3.9.5.1 | 3.9.5.2 | 3.9.5.3 | 3.9.5.4 | 3.9.5.5 | 3.9.5.6 | 3.9.5.7 | 3.9.5.8 |
| 3.9.5.9 | 3.9.6.1 | 3.9.6.2 | 3.9.6.3 | 3.9.6.4 | 3.9.6.5 | 3.9.6.6 | 3.9.6.7 | 3.9.6.8 | 3.9.6.9 |
| 3.9.7.1 | 3.9.7.2 | 3.9.7.3 | 3.9.7.4 | 3.9.7.5 | 3.9.7.6 | 3.9.7.7 | 3.9.7.8 | 3.9.7.9 | 3.9.8.1 |
| 3.9.8.2 | 3.9.8.3 | 3.9.8.4 | 3.9.8.5 | 3.9.8.6 | 3.9.8.7 | 3.9.8.8 | 3.9.8.9 | 3.9.9.1 | 3.9.9.2 |
| 3.9.9.3 | 3.9.9.4 | 3.9.9.5 | 3.9.9.6 | 3.9.9.7 | 3.9.9.8 | 3.9.9.9 | 4.1.1.1 | 4.1.1.2 | 4.1.1.3 |
| 4.1.1.4 | 4.1.1.5 | 4.1.1.6 | 4.1.1.7 | 4.1.1.8 | 4.1.1.9 | 4.1.2.1 | 4.1.2.2 | 4.1.2.3 | 4.1.2.4 |
| 4.1.2.5 | 4.1.2.6 | 4.1.2.7 | 4.1.2.8 | 4.1.2.9 | 4.1.3.1 | 4.1.3.2 | 4.1.3.3 | 4.1.3.4 | 4.1.3.5 |
| 4.1.3.6 | 4.1.3.7 | 4.1.3.8 | 4.1.3.9 | 4.1.4.1 | 4.1.4.2 | 4.1.4.3 | 4.1.4.4 | 4.1.4.5 | 4.1.4.6 |
| 4.1.4.7 | 4.1.4.8 | 4.1.4.9 | 4.1.5.1 | 4.1.5.2 | 4.1.5.3 | 4.1.5.4 | 4.1.5.5 | 4.1.5.6 | 4.1.5.7 |
| 4.1.5.8 | 4.1.5.9 | 4.1.6.1 | 4.1.6.2 | 4.1.6.3 | 4.1.6.4 | 4.1.6.5 | 4.1.6.6 | 4.1.6.7 | 4.1.6.8 |
| 4.1.6.9 | 4.1.7.1 | 4.1.7.2 | 4.1.7.3 | 4.1.7.4 | 4.1.7.5 | 4.1.7.6 | 4.1.7.7 | 4.1.7.8 | 4.1.7.9 |
| 4.1.8.1 | 4.1.8.2 | 4.1.8.3 | 4.1.8.4 | 4.1.8.5 | 4.1.8.6 | 4.1.8.7 | 4.1.8.8 | 4.1.8.9 | 4.1.9.1 |
| 4.1.9.2 | 4.1.9.3 | 4.1.9.4 | 4.1.9.5 | 4.1.9.6 | 4.1.9.7 | 4.1.9.8 | 4.1.9.9 | 4.2.1.1 | 4.2.1.2 |
| 4.2.1.3 | 4.2.1.4 | 4.2.1.5 | 4.2.1.6 | 4.2.1.7 | 4.2.1.8 | 4.2.1.9 | 4.2.2.1 | 4.2.2.2 | 4.2.2.3 |
| 4.2.2.4 | 4.2.2.5 | 4.2.2.6 | 4.2.2.7 | 4.2.2.8 | 4.2.2.9 | 4.2.3.1 | 4.2.3.2 | 4.2.3.3 | 4.2.3.4 |
| 4.2.3.5 | 4.2.3.6 | 4.2.3.7 | 4.2.3.8 | 4.2.3.9 | 4.2.4.1 | 4.2.4.2 | 4.2.4.3 | 4.2.4.4 | 4.2.4.5 |
| 4.2.4.6 | 4.2.4.7 | 4.2.4.8 | 4.2.4.9 | 4.2.5.1 | 4.2.5.2 | 4.2.5.3 | 4.2.5.4 | 4.2.5.5 | 4.2.5.6 |
| 4.2.5.7 | 4.2.5.8 | 4.2.5.9 | 4.2.6.1 | 4.2.6.2 | 4.2.6.3 | 4.2.6.4 | 4.2.6.5 | 4.2.6.6 | 4.2.6.7 |
| 4.2.6.8 | 4.2.6.9 | 4.2.7.1 | 4.2.7.2 | 4.2.7.3 | 4.2.7.4 | 4.2.7.5 | 4.2.7.6 | 4.2.7.7 | 4.2.7.8 |
| 4.2.7.9 | 4.2.8.1 | 4.2.8.2 | 4.2.8.3 | 4.2.8.4 | 4.2.8.5 | 4.2.8.6 | 4.2.8.7 | 4.2.8.8 | 4.2.8.9 |
| 4.2.9.1 | 4.2.9.2 | 4.2.9.3 | 4.2.9.4 | 4.2.9.5 | 4.2.9.6 | 4.2.9.7 | 4.2.9.8 | 4.2.9.9 | 4.3.1.1 |
| 4.3.1.2 | 4.3.1.3 | 4.3.1.4 | 4.3.1.5 | 4.3.1.6 | 4.3.1.7 | 4.3.1.8 | 4.3.1.9 | 4.3.2.1 | 4.3.2.2 |
| 4.3.2.3 | 4.3.2.4 | 4.3.2.5 | 4.3.2.6 | 4.3.2.7 | 4.3.2.8 | 4.3.2.9 | 4.3.3.1 | 4.3.3.2 | 4.3.3.3 |

TABLE 1-continued

| | | | | | | | | | |
|---|---|---|---|---|---|---|---|---|---|
| 4.3.3.4 | 4.3.3.5 | 4.3.3.6 | 4.3.3.7 | 4.3.3.8 | 4.3.3.9 | 4.3.4.1 | 4.3.4.2 | 4.3.4.3 | 4.3.4.4 |
| 4.3.4.5 | 4.3.4.6 | 4.3.4.7 | 4.3.4.8 | 4.3.4.9 | 4.3.5.1 | 4.3.5.2 | 4.3.5.3 | 4.3.5.4 | 4.3.5.5 |
| 4.3.5.6 | 4.3.5.7 | 4.3.5.8 | 4.3.5.9 | 4.3.6.1 | 4.3.6.2 | 4.3.6.3 | 4.3.6.4 | 4.3.6.5 | 4.3.6.6 |
| 4.3.6.7 | 4.3.6.8 | 4.3.6.9 | 4.3.7.1 | 4.3.7.2 | 4.3.7.3 | 4.3.7.4 | 4.3.7.5 | 4.3.7.6 | 4.3.7.7 |
| 4.3.7.8 | 4.3.7.9 | 4.3.8.1 | 4.3.8.2 | 4.3.8.3 | 4.3.8.4 | 4.3.8.5 | 4.3.8.6 | 4.3.8.7 | 4.3.8.8 |
| 4.3.8.9 | 4.3.9.1 | 4.3.9.2 | 4.3.9.3 | 4.3.9.4 | 4.3.9.5 | 4.3.9.6 | 4.3.9.7 | 4.3.9.8 | 4.3.9.9 |
| 4.4.1.1 | 4.4.1.2 | 4.4.1.3 | 4.4.1.4 | 4.4.1.5 | 4.4.1.6 | 4.4.1.7 | 4.4.1.8 | 4.4.1.9 | 4.4.2.1 |
| 4.4.2.2 | 4.4.2.3 | 4.4.2.4 | 4.4.2.5 | 4.4.2.6 | 4.4.2.7 | 4.4.2.8 | 4.4.2.9 | 4.4.3.1 | 4.4.3.2 |
| 4.4.3.3 | 4.4.3.4 | 4.4.3.5 | 4.4.3.6 | 4.4.3.7 | 4.4.3.8 | 4.4.3.9 | 4.4.4.1 | 4.4.4.2 | 4.4.4.3 |
| 4.4.4.4 | 4.4.4.5 | 4.4.4.6 | 4.4.4.7 | 4.4.4.8 | 4.4.4.9 | 4.4.5.1 | 4.4.5.2 | 4.4.5.3 | 4.4.5.4 |
| 4.4.5.5 | 4.4.5.6 | 4.4.5.7 | 4.4.5.8 | 4.4.5.9 | 4.4.6.1 | 4.4.6.2 | 4.4.6.3 | 4.4.6.4 | 4.4.6.5 |
| 4.4.6.6 | 4.4.6.7 | 4.4.6.8 | 4.4.6.9 | 4.4.7.1 | 4.4.7.2 | 4.4.7.3 | 4.4.7.4 | 4.4.7.5 | 4.4.7.6 |
| 4.4.7.7 | 4.4.7.8 | 4.4.7.9 | 4.4.8.1 | 4.4.8.2 | 4.4.8.3 | 4.4.8.4 | 4.4.8.5 | 4.4.8.6 | 4.4.8.7 |
| 4.4.8.8 | 4.4.8.9 | 4.4.9.1 | 4.4.9.2 | 4.4.9.3 | 4.4.9.4 | 4.4.9.5 | 4.4.9.6 | 4.4.9.7 | 4.4.9.8 |
| 4.4.9.9 | 4.5.1.1 | 4.5.1.2 | 4.5.1.3 | 4.5.1.4 | 4.5.1.5 | 4.5.1.6 | 4.5.1.7 | 4.5.1.8 | 4.5.1.9 |
| 4.5.2.1 | 4.5.2.2 | 4.5.2.3 | 4.5.2.4 | 4.5.2.5 | 4.5.2.6 | 4.5.2.7 | 4.5.2.8 | 4.5.2.9 | 4.5.3.1 |
| 4.5.3.2 | 4.5.3.3 | 4.5.3.4 | 4.5.3.5 | 4.5.3.6 | 4.5.3.7 | 4.5.3.8 | 4.5.3.9 | 4.5.4.1 | 4.5.4.2 |
| 4.5.4.3 | 4.5.4.4 | 4.5.4.5 | 4.5.4.6 | 4.5.4.7 | 4.5.4.8 | 4.5.4.9 | 4.5.5.1 | 4.5.5.2 | 4.5.5.3 |
| 4.5.5.4 | 4.5.5.5 | 4.5.5.6 | 4.5.5.7 | 4.5.5.8 | 4.5.5.9 | 4.5.6.1 | 4.5.6.2 | 4.5.6.3 | 4.5.6.4 |
| 4.5.6.5 | 4.5.6.6 | 4.5.6.7 | 4.5.6.8 | 4.5.6.9 | 4.5.7.1 | 4.5.7.2 | 4.5.7.3 | 4.5.7.4 | 4.5.7.5 |
| 4.5.7.6 | 4.5.7.7 | 4.5.7.8 | 4.5.7.9 | 4.5.8.1 | 4.5.8.2 | 4.5.8.3 | 4.5.8.4 | 4.5.8.5 | 4.5.8.6 |
| 4.5.8.7 | 4.5.8.8 | 4.5.8.9 | 4.5.9.1 | 4.5.9.2 | 4.5.9.3 | 4.5.9.4 | 4.5.9.5 | 4.5.9.6 | 4.5.9.7 |
| 4.5.9.8 | 4.5.9.9 | 4.6.1.1 | 4.6.1.2 | 4.6.1.3 | 4.6.1.4 | 4.6.1.5 | 4.6.1.6 | 4.6.1.7 | 4.6.1.8 |
| 4.6.1.9 | 4.6.2.1 | 4.6.2.2 | 4.6.2.3 | 4.6.2.4 | 4.6.2.5 | 4.6.2.6 | 4.6.2.7 | 4.6.2.8 | 4.6.2.9 |
| 4.6.3.1 | 4.6.3.2 | 4.6.3.3 | 4.6.3.4 | 4.6.3.5 | 4.6.3.6 | 4.6.3.7 | 4.6.3.8 | 4.6.3.9 | 4.6.4.1 |
| 4.6.4.2 | 4.6.4.3 | 4.6.4.4 | 4.6.4.5 | 4.6.4.6 | 4.6.4.7 | 4.6.4.8 | 4.6.4.9 | 4.6.5.1 | 4.6.5.2 |
| 4.6.5.3 | 4.6.5.4 | 4.6.5.5 | 4.6.5.6 | 4.6.5.7 | 4.6.5.8 | 4.6.5.9 | 4.6.6.1 | 4.6.6.2 | 4.6.6.3 |
| 4.6.6.4 | 4.6.6.5 | 4.6.6.6 | 4.6.6.7 | 4.6.6.8 | 4.6.6.9 | 4.6.7.1 | 4.6.7.2 | 4.6.7.3 | 4.6.7.4 |
| 4.6.7.5 | 4.6.7.6 | 4.6.7.7 | 4.6.7.8 | 4.6.7.9 | 4.6.8.1 | 4.6.8.2 | 4.6.8.3 | 4.6.8.4 | 4.6.8.5 |
| 4.6.8.6 | 4.6.8.7 | 4.6.8.8 | 4.6.8.9 | 4.6.9.1 | 4.6.9.2 | 4.6.9.3 | 4.6.9.4 | 4.6.9.5 | 4.6.9.6 |
| 4.6.9.7 | 4.6.9.8 | 4.6.9.9 | 4.7.1.1 | 4.7.1.2 | 4.7.1.3 | 4.7.1.4 | 4.7.1.5 | 4.7.1.6 | 4.7.1.7 |
| 4.7.1.8 | 4.7.1.9 | 4.7.2.1 | 4.7.2.2 | 4.7.2.3 | 4.7.2.4 | 4.7.2.5 | 4.7.2.6 | 4.7.2.7 | 4.7.2.8 |
| 4.7.2.9 | 4.7.3.1 | 4.7.3.2 | 4.7.3.3 | 4.7.3.4 | 4.7.3.5 | 4.7.3.6 | 4.7.3.7 | 4.7.3.8 | 4.7.3.9 |
| 4.7.4.1 | 4.7.4.2 | 4.7.4.3 | 4.7.4.4 | 4.7.4.5 | 4.7.4.6 | 4.7.4.7 | 4.7.4.8 | 4.7.4.9 | 4.7.5.1 |
| 4.7.5.2 | 4.7.5.3 | 4.7.5.4 | 4.7.5.5 | 4.7.5.6 | 4.7.5.7 | 4.7.5.8 | 4.7.5.9 | 4.7.6.1 | 4.7.6.2 |
| 4.7.6.3 | 4.7.6.4 | 4.7.6.5 | 4.7.6.6 | 4.7.6.7 | 4.7.6.8 | 4.7.6.9 | 4.7.7.1 | 4.7.7.2 | 4.7.7.3 |
| 4.7.7.4 | 4.7.7.5 | 4.7.7.6 | 4.7.7.7 | 4.7.7.8 | 4.7.7.9 | 4.7.8.1 | 4.7.8.2 | 4.7.8.3 | 4.7.8.4 |
| 4.7.8.5 | 4.7.8.6 | 4.7.8.7 | 4.7.8.8 | 4.7.8.9 | 4.7.9.1 | 4.7.9.2 | 4.7.9.3 | 4.7.9.4 | 4.7.9.5 |
| 4.7.9.6 | 4.7.9.7 | 4.7.9.8 | 4.7.9.9 | 4.8.1.1 | 4.8.1.2 | 4.8.1.3 | 4.8.1.4 | 4.8.1.5 | 4.8.1.6 |
| 4.8.1.7 | 4.8.1.8 | 4.8.1.9 | 4.8.2.1 | 4.8.2.2 | 4.8.2.3 | 4.8.2.4 | 4.8.2.5 | 4.8.2.6 | 4.8.2.7 |
| 4.8.2.8 | 4.8.2.9 | 4.8.3.1 | 4.8.3.2 | 4.8.3.3 | 4.8.3.4 | 4.8.3.5 | 4.8.3.6 | 4.8.3.7 | 4.8.3.8 |
| 4.8.3.9 | 4.8.4.1 | 4.8.4.2 | 4.8.4.3 | 4.8.4.4 | 4.8.4.5 | 4.8.4.6 | 4.8.4.7 | 4.8.4.8 | 4.8.4.9 |
| 4.8.5.1 | 4.8.5.2 | 4.8.5.3 | 4.8.5.4 | 4.8.5.5 | 4.8.5.6 | 4.8.5.7 | 4.8.5.8 | 4.8.5.9 | 4.8.6.1 |
| 4.8.6.2 | 4.8.6.3 | 4.8.6.4 | 4.8.6.5 | 4.8.6.6 | 4.8.6.7 | 4.8.6.8 | 4.8.6.9 | 4.8.7.1 | 4.8.7.2 |
| 4.8.7.3 | 4.8.7.4 | 4.8.7.5 | 4.8.7.6 | 4.8.7.7 | 4.8.7.8 | 4.8.7.9 | 4.8.8.1 | 4.8.8.2 | 4.8.8.3 |
| 4.8.8.4 | 4.8.8.5 | 4.8.8.6 | 4.8.8.7 | 4.8.8.8 | 4.8.8.9 | 4.8.9.1 | 4.8.9.2 | 4.8.9.3 | 4.8.9.4 |
| 4.8.9.5 | 4.8.9.6 | 4.8.9.7 | 4.8.9.8 | 4.8.9.9 | 4.9.1.1 | 4.9.1.2 | 4.9.1.3 | 4.9.1.4 | 4.9.1.5 |
| 4.9.1.6 | 4.9.1.7 | 4.9.1.8 | 4.9.1.9 | 4.9.2.1 | 4.9.2.2 | 4.9.2.3 | 4.9.2.4 | 4.9.2.5 | 4.9.2.6 |
| 4.9.2.7 | 4.9.2.8 | 4.9.2.9 | 4.9.3.1 | 4.9.3.2 | 4.9.3.3 | 4.9.3.4 | 4.9.3.5 | 4.9.3.6 | 4.9.3.7 |
| 4.9.3.8 | 4.9.3.9 | 4.9.4.1 | 4.9.4.2 | 4.9.4.3 | 4.9.4.4 | 4.9.4.5 | 4.9.4.6 | 4.9.4.7 | 4.9.4.8 |
| 4.9.4.9 | 4.9.5.1 | 4.9.5.2 | 4.9.5.3 | 4.9.5.4 | 4.9.5.5 | 4.9.5.6 | 4.9.5.7 | 4.9.5.8 | 4.9.5.9 |
| 4.9.6.1 | 4.9.6.2 | 4.9.6.3 | 4.9.6.4 | 4.9.6.5 | 4.9.6.6 | 4.9.6.7 | 4.9.6.8 | 4.9.6.9 | 4.9.7.1 |
| 4.9.7.2 | 4.9.7.3 | 4.9.7.4 | 4.9.7.5 | 4.9.7.6 | 4.9.7.7 | 4.9.7.8 | 4.9.7.9 | 4.9.8.1 | 4.9.8.2 |
| 4.9.8.3 | 4.9.8.4 | 4.9.8.5 | 4.9.8.6 | 4.9.8.7 | 4.9.8.8 | 4.9.8.9 | 4.9.9.1 | 4.9.9.2 | 4.9.9.3 |
| 4.9.9.4 | 4.9.9.5 | 4.9.9.6 | 4.9.9.7 | 4.9.9.8 | 4.9.9.9 | 5.1.1.1 | 5.1.1.2 | 5.1.1.3 | 5.1.1.4 |
| 5.1.1.5 | 5.1.1.6 | 5.1.1.7 | 5.1.1.8 | 5.1.1.9 | 5.1.2.1 | 5.1.2.2 | 5.1.2.3 | 5.1.2.4 | 5.1.2.5 |
| 5.1.2.6 | 5.1.2.7 | 5.1.2.8 | 5.1.2.9 | 5.1.3.1 | 5.1.3.2 | 5.1.3.3 | 5.1.3.4 | 5.1.3.5 | 5.1.3.6 |
| 5.1.3.7 | 5.1.3.8 | 5.1.3.9 | 5.1.4.1 | 5.1.4.2 | 5.1.4.3 | 5.1.4.4 | 5.1.4.5 | 5.1.4.6 | 5.1.4.7 |
| 5.1.4.8 | 5.1.4.9 | 5.1.5.1 | 5.1.5.2 | 5.1.5.3 | 5.1.5.4 | 5.1.5.5 | 5.1.5.6 | 5.1.5.7 | 5.1.5.8 |
| 5.1.5.9 | 5.1.6.1 | 5.1.6.2 | 5.1.6.3 | 5.1.6.4 | 5.1.6.5 | 5.1.6.6 | 5.1.6.7 | 5.1.6.8 | 5.1.6.9 |
| 5.1.7.1 | 5.1.7.2 | 5.1.7.3 | 5.1.7.4 | 5.1.7.5 | 5.1.7.6 | 5.1.7.7 | 5.1.7.8 | 5.1.7.9 | 5.1.8.1 |
| 5.1.8.2 | 5.1.8.3 | 5.1.8.4 | 5.1.8.5 | 5.1.8.6 | 5.1.8.7 | 5.1.8.8 | 5.1.8.9 | 5.1.9.1 | 5.1.9.2 |
| 5.1.9.3 | 5.1.9.4 | 5.1.9.5 | 5.1.9.6 | 5.1.9.7 | 5.1.9.8 | 5.1.9.9 | 5.2.1.1 | 5.2.1.2 | 5.2.1.3 |
| 5.2.1.4 | 5.2.1.5 | 5.2.1.6 | 5.2.1.7 | 5.2.1.8 | 5.2.1.9 | 5.2.2.1 | 5.2.2.2 | 5.2.2.3 | 5.2.2.4 |
| 5.2.2.5 | 5.2.2.6 | 5.2.2.7 | 5.2.2.8 | 5.2.2.9 | 5.2.3.1 | 5.2.3.2 | 5.2.3.3 | 5.2.3.4 | 5.2.3.5 |
| 5.2.3.6 | 5.2.3.7 | 5.2.3.8 | 5.2.3.9 | 5.2.4.1 | 5.2.4.2 | 5.2.4.3 | 5.2.4.4 | 5.2.4.5 | 5.2.4.6 |
| 5.2.4.7 | 5.2.4.8 | 5.2.4.9 | 5.2.5.1 | 5.2.5.2 | 5.2.5.3 | 5.2.5.4 | 5.2.5.5 | 5.2.5.6 | 5.2.5.7 |
| 5.2.5.8 | 5.2.5.9 | 5.2.6.1 | 5.2.6.2 | 5.2.6.3 | 5.2.6.4 | 5.2.6.5 | 5.2.6.6 | 5.2.6.7 | 5.2.6.8 |
| 5.2.6.9 | 5.2.7.1 | 5.2.7.2 | 5.2.7.3 | 5.2.7.4 | 5.2.7.5 | 5.2.7.6 | 5.2.7.7 | 5.2.7.8 | 5.2.7.9 |
| 5.2.8.1 | 5.2.8.2 | 5.2.8.3 | 5.2.8.4 | 5.2.8.5 | 5.2.8.6 | 5.2.8.7 | 5.2.8.8 | 5.2.8.9 | 5.2.9.1 |
| 5.2.9.2 | 5.2.9.3 | 5.2.9.4 | 5.2.9.5 | 5.2.9.6 | 5.2.9.7 | 5.2.9.8 | 5.2.9.9 | 5.3.1.1 | 5.3.1.2 |
| 5.3.1.3 | 5.3.1.4 | 5.3.1.5 | 5.3.1.6 | 5.3.1.7 | 5.3.1.8 | 5.3.1.9 | 5.3.2.1 | 5.3.2.2 | 5.3.2.3 |
| 5.3.2.4 | 5.3.2.5 | 5.3.2.6 | 5.3.2.7 | 5.3.2.8 | 5.3.2.9 | 5.3.3.1 | 5.3.3.2 | 5.3.3.3 | 5.3.3.4 |
| 5.3.3.5 | 5.3.3.6 | 5.3.3.7 | 5.3.3.8 | 5.3.3.9 | 5.3.4.1 | 5.3.4.2 | 5.3.4.3 | 5.3.4.4 | 5.3.4.5 |
| 5.3.4.6 | 5.3.4.7 | 5.3.4.8 | 5.3.4.9 | 5.3.5.1 | 5.3.5.2 | 5.3.5.3 | 5.3.5.4 | 5.3.5.5 | 5.3.5.6 |
| 5.3.5.7 | 5.3.5.8 | 5.3.5.9 | 5.3.6.1 | 5.3.6.2 | 5.3.6.3 | 5.3.6.4 | 5.3.6.5 | 5.3.6.6 | 5.3.6.7 |
| 5.3.6.8 | 5.3.6.9 | 5.3.7.1 | 5.3.7.2 | 5.3.7.3 | 5.3.7.4 | 5.3.7.5 | 5.3.7.6 | 5.3.7.7 | 5.3.7.8 |
| 5.3.7.9 | 5.3.8.1 | 5.3.8.2 | 5.3.8.3 | 5.3.8.4 | 5.3.8.5 | 5.3.8.6 | 5.3.8.7 | 5.3.8.8 | 5.3.8.9 |
| 5.3.9.1 | 5.3.9.2 | 5.3.9.3 | 5.3.9.4 | 5.3.9.5 | 5.3.9.6 | 5.3.9.7 | 5.3.9.8 | 5.3.9.9 | 5.4.1.1 |

TABLE 1-continued

| | | | | | | | | | |
|---|---|---|---|---|---|---|---|---|---|
| 5.4.1.2 | 5.4.1.3 | 5.4.1.4 | 5.4.1.5 | 5.4.1.6 | 5.4.1.7 | 5.4.1.8 | 5.4.1.9 | 5.4.2.1 | 5.4.2.2 |
| 5.4.2.3 | 5.4.2.4 | 5.4.2.5 | 5.4.2.6 | 5.4.2.7 | 5.4.2.8 | 5.4.2.9 | 5.4.3.1 | 5.4.3.2 | 5.4.3.3 |
| 5.4.3.4 | 5.4.3.5 | 5.4.3.6 | 5.4.3.7 | 5.4.3.8 | 5.4.3.9 | 5.4.4.1 | 5.4.4.2 | 5.4.4.3 | 5.4.4.4 |
| 5.4.4.5 | 5.4.4.6 | 5.4.4.7 | 5.4.4.8 | 5.4.4.9 | 5.4.5.1 | 5.4.5.2 | 5.4.5.3 | 5.4.5.4 | 5.4.5.5 |
| 5.4.5.6 | 5.4.5.7 | 5.4.5.8 | 5.4.5.9 | 5.4.6.1 | 5.4.6.2 | 5.4.6.3 | 5.4.6.4 | 5.4.6.5 | 5.4.6.6 |
| 5.4.6.7 | 5.4.6.8 | 5.4.6.9 | 5.4.7.1 | 5.4.7.2 | 5.4.7.3 | 5.4.7.4 | 5.4.7.5 | 5.4.7.6 | 5.4.7.7 |
| 5.4.7.8 | 5.4.7.9 | 5.4.8.1 | 5.4.8.2 | 5.4.8.3 | 5.4.8.4 | 5.4.8.5 | 5.4.8.6 | 5.4.8.7 | 5.4.8.8 |
| 5.4.8.9 | 5.4.9.1 | 5.4.9.2 | 5.4.9.3 | 5.4.9.4 | 5.4.9.5 | 5.4.9.6 | 5.4.9.7 | 5.4.9.8 | 5.4.9.9 |
| 5.5.1.1 | 5.5.1.2 | 5.5.1.3 | 5.5.1.4 | 5.5.1.5 | 5.5.1.6 | 5.5.1.7 | 5.5.1.8 | 5.5.1.9 | 5.5.2.1 |
| 5.5.2.2 | 5.5.2.3 | 5.5.2.4 | 5.5.2.5 | 5.5.2.6 | 5.5.2.7 | 5.5.2.8 | 5.5.2.9 | 5.5.3.1 | 5.5.3.2 |
| 5.5.3.3 | 5.5.3.4 | 5.5.3.5 | 5.5.3.6 | 5.5.3.7 | 5.5.3.8 | 5.5.3.9 | 5.5.4.1 | 5.5.4.2 | 5.5.4.3 |
| 5.5.4.4 | 5.5.4.5 | 5.5.4.6 | 5.5.4.7 | 5.5.4.8 | 5.5.4.9 | 5.5.5.1 | 5.5.5.2 | 5.5.5.3 | 5.5.5.4 |
| 5.5.5.5 | 5.5.5.6 | 5.5.5.7 | 5.5.5.8 | 5.5.5.9 | 5.5.6.1 | 5.5.6.2 | 5.5.6.3 | 5.5.6.4 | 5.5.6.5 |
| 5.5.6.6 | 5.5.6.7 | 5.5.6.8 | 5.5.6.9 | 5.5.7.1 | 5.5.7.2 | 5.5.7.3 | 5.5.7.4 | 5.5.7.5 | 5.5.7.6 |
| 5.5.7.7 | 5.5.7.8 | 5.5.7.9 | 5.5.8.1 | 5.5.8.2 | 5.5.8.3 | 5.5.8.4 | 5.5.8.5 | 5.5.8.6 | 5.5.8.7 |
| 5.5.8.8 | 5.5.8.9 | 5.5.9.1 | 5.5.9.2 | 5.5.9.3 | 5.5.9.4 | 5.5.9.5 | 5.5.9.6 | 5.5.9.7 | 5.5.9.8 |
| 5.5.9.9 | 5.6.1.1 | 5.6.1.2 | 5.6.1.3 | 5.6.1.4 | 5.6.1.5 | 5.6.1.6 | 5.6.1.7 | 5.6.1.8 | 5.6.1.9 |
| 5.6.2.1 | 5.6.2.2 | 5.6.2.3 | 5.6.2.4 | 5.6.2.5 | 5.6.2.6 | 5.6.2.7 | 5.6.2.8 | 5.6.2.9 | 5.6.3.1 |
| 5.6.3.2 | 5.6.3.3 | 5.6.3.4 | 5.6.3.5 | 5.6.3.6 | 5.6.3.7 | 5.6.3.8 | 5.6.3.9 | 5.6.4.1 | 5.6.4.2 |
| 5.6.4.3 | 5.6.4.4 | 5.6.4.5 | 5.6.4.6 | 5.6.4.7 | 5.6.4.8 | 5.6.4.9 | 5.6.5.1 | 5.6.5.2 | 5.6.5.3 |
| 5.6.5.4 | 5.6.5.5 | 5.6.5.6 | 5.6.5.7 | 5.6.5.8 | 5.6.5.9 | 5.6.6.1 | 5.6.6.2 | 5.6.6.3 | 5.6.6.4 |
| 5.6.6.5 | 5.6.6.6 | 5.6.6.7 | 5.6.6.8 | 5.6.6.9 | 5.6.7.1 | 5.6.7.2 | 5.6.7.3 | 5.6.7.4 | 5.6.7.5 |
| 5.6.7.6 | 5.6.7.7 | 5.6.7.8 | 5.6.7.9 | 5.6.8.1 | 5.6.8.2 | 5.6.8.3 | 5.6.8.4 | 5.6.8.5 | 5.6.8.6 |
| 5.6.8.7 | 5.6.8.8 | 5.6.8.9 | 5.6.9.1 | 5.6.9.2 | 5.6.9.3 | 5.6.9.4 | 5.6.9.5 | 5.6.9.6 | 5.6.9.7 |
| 5.6.9.8 | 5.6.9.9 | 5.7.1.1 | 5.7.1.2 | 5.7.1.3 | 5.7.1.4 | 5.7.1.5 | 5.7.1.6 | 5.7.1.7 | 5.7.1.8 |
| 5.7.1.9 | 5.7.2.1 | 5.7.2.2 | 5.7.2.3 | 5.7.2.4 | 5.7.2.5 | 5.7.2.6 | 5.7.2.7 | 5.7.2.8 | 5.7.2.9 |
| 5.7.3.1 | 5.7.3.2 | 5.7.3.3 | 5.7.3.4 | 5.7.3.5 | 5.7.3.6 | 5.7.3.7 | 5.7.3.8 | 5.7.3.9 | 5.7.4.1 |
| 5.7.4.2 | 5.7.4.3 | 5.7.4.4 | 5.7.4.5 | 5.7.4.6 | 5.7.4.7 | 5.7.4.8 | 5.7.4.9 | 5.7.5.1 | 5.7.5.2 |
| 5.7.5.3 | 5.7.5.4 | 5.7.5.5 | 5.7.5.6 | 5.7.5.7 | 5.7.5.8 | 5.7.5.9 | 5.7.6.1 | 5.7.6.2 | 5.7.6.3 |
| 5.7.6.4 | 5.7.6.5 | 5.7.6.6 | 5.7.6.7 | 5.7.6.8 | 5.7.6.9 | 5.7.7.1 | 5.7.7.2 | 5.7.7.3 | 5.7.7.4 |
| 5.7.7.5 | 5.7.7.6 | 5.7.7.7 | 5.7.7.8 | 5.7.7.9 | 5.7.8.1 | 5.7.8.2 | 5.7.8.3 | 5.7.8.4 | 5.7.8.5 |
| 5.7.8.6 | 5.7.8.7 | 5.7.8.8 | 5.7.8.9 | 5.7.9.1 | 5.7.9.2 | 5.7.9.3 | 5.7.9.4 | 5.7.9.5 | 5.7.9.6 |
| 5.7.9.7 | 5.7.9.8 | 5.7.9.9 | 5.8.1.1 | 5.8.1.2 | 5.8.1.3 | 5.8.1.4 | 5.8.1.5 | 5.8.1.6 | 5.8.1.7 |
| 5.8.1.8 | 5.8.1.9 | 5.8.2.1 | 5.8.2.2 | 5.8.2.3 | 5.8.2.4 | 5.8.2.5 | 5.8.2.6 | 5.8.2.7 | 5.8.2.8 |
| 5.8.2.9 | 5.8.3.1 | 5.8.3.2 | 5.8.3.3 | 5.8.3.4 | 5.8.3.5 | 5.8.3.6 | 5.8.3.7 | 5.8.3.8 | 5.8.3.9 |
| 5.8.4.1 | 5.8.4.2 | 5.8.4.3 | 5.8.4.4 | 5.8.4.5 | 5.8.4.6 | 5.8.4.7 | 5.8.4.8 | 5.8.4.9 | 5.8.5.1 |
| 5.8.5.2 | 5.8.5.3 | 5.8.5.4 | 5.8.5.5 | 5.8.5.6 | 5.8.5.7 | 5.8.5.8 | 5.8.5.9 | 5.8.6.1 | 5.8.6.2 |
| 5.8.6.3 | 5.8.6.4 | 5.8.6.5 | 5.8.6.6 | 5.8.6.7 | 5.8.6.8 | 5.8.6.9 | 5.8.7.1 | 5.8.7.2 | 5.8.7.3 |
| 5.8.7.4 | 5.8.7.5 | 5.8.7.6 | 5.8.7.7 | 5.8.7.8 | 5.8.7.9 | 5.8.8.1 | 5.8.8.2 | 5.8.8.3 | 5.8.8.4 |
| 5.8.8.5 | 5.8.8.6 | 5.8.8.7 | 5.8.8.8 | 5.8.8.9 | 5.8.9.1 | 5.8.9.2 | 5.8.9.3 | 5.8.9.4 | 5.8.9.5 |
| 5.8.9.6 | 5.8.9.7 | 5.8.9.8 | 5.8.9.9 | 5.9.1.1 | 5.9.1.2 | 5.9.1.3 | 5.9.1.4 | 5.9.1.5 | 5.9.1.6 |
| 5.9.1.7 | 5.9.1.8 | 5.9.1.9 | 5.9.2.1 | 5.9.2.2 | 5.9.2.3 | 5.9.2.4 | 5.9.2.5 | 5.9.2.6 | 5.9.2.7 |
| 5.9.2.8 | 5.9.2.9 | 5.9.3.1 | 5.9.3.2 | 5.9.3.3 | 5.9.3.4 | 5.9.3.5 | 5.9.3.6 | 5.9.3.7 | 5.9.3.8 |
| 5.9.3.9 | 5.9.4.1 | 5.9.4.2 | 5.9.4.3 | 5.9.4.4 | 5.9.4.5 | 5.9.4.6 | 5.9.4.7 | 5.9.4.8 | 5.9.4.9 |
| 5.9.5.1 | 5.9.5.2 | 5.9.5.3 | 5.9.5.4 | 5.9.5.5 | 5.9.5.6 | 5.9.5.7 | 5.9.5.8 | 5.9.5.9 | 5.9.6.1 |
| 5.9.6.2 | 5.9.6.3 | 5.9.6.4 | 5.9.6.5 | 5.9.6.6 | 5.9.6.7 | 5.9.6.8 | 5.9.6.9 | 5.9.7.1 | 5.9.7.2 |
| 5.9.7.3 | 5.9.7.4 | 5.9.7.5 | 5.9.7.6 | 5.9.7.7 | 5.9.7.8 | 5.9.7.9 | 5.9.8.1 | 5.9.8.2 | 5.9.8.3 |
| 5.9.8.4 | 5.9.8.5 | 5.9.8.6 | 5.9.8.7 | 5.9.8.8 | 5.9.8.9 | 5.9.9.1 | 5.9.9.2 | 5.9.9.3 | 5.9.9.4 |
| 5.9.9.5 | 5.9.9.6 | 5.9.9.7 | 5.9.9.8 | 5.9.9.9 | 6.1.1.1 | 6.1.1.2 | 6.1.1.3 | 6.1.1.4 | 6.1.1.5 |
| 6.1.1.6 | 6.1.1.7 | 6.1.1.8 | 6.1.1.9 | 6.1.2.1 | 6.1.2.2 | 6.1.2.3 | 6.1.2.4 | 6.1.2.5 | 6.1.2.6 |
| 6.1.2.7 | 6.1.2.8 | 6.1.2.9 | 6.1.3.1 | 6.1.3.2 | 6.1.3.3 | 6.1.3.4 | 6.1.3.5 | 6.1.3.6 | 6.1.3.7 |
| 6.1.3.8 | 6.1.3.9 | 6.1.4.1 | 6.1.4.2 | 6.1.4.3 | 6.1.4.4 | 6.1.4.5 | 6.1.4.6 | 6.1.4.7 | 6.1.4.8 |
| 6.1.4.9 | 6.1.5.1 | 6.1.5.2 | 6.1.5.3 | 6.1.5.4 | 6.1.5.5 | 6.1.5.6 | 6.1.5.7 | 6.1.5.8 | 6.1.5.9 |
| 6.1.6.1 | 6.1.6.2 | 6.1.6.3 | 6.1.6.4 | 6.1.6.5 | 6.1.6.6 | 6.1.6.7 | 6.1.6.8 | 6.1.6.9 | 6.1.7.1 |
| 6.1.7.2 | 6.1.7.3 | 6.1.7.4 | 6.1.7.5 | 6.1.7.6 | 6.1.7.7 | 6.1.7.8 | 6.1.7.9 | 6.1.8.1 | 6.1.8.2 |
| 6.1.8.3 | 6.1.8.4 | 6.1.8.5 | 6.1.8.6 | 6.1.8.7 | 6.1.8.8 | 6.1.8.9 | 6.1.9.1 | 6.1.9.2 | 6.1.9.3 |
| 6.1.9.4 | 6.1.9.5 | 6.1.9.6 | 6.1.9.7 | 6.1.9.8 | 6.1.9.9 | 6.2.1.1 | 6.2.1.2 | 6.2.1.3 | 6.2.1.4 |
| 6.2.1.5 | 6.2.1.6 | 6.2.1.7 | 6.2.1.8 | 6.2.1.9 | 6.2.2.1 | 6.2.2.2 | 6.2.2.3 | 6.2.2.4 | 6.2.2.5 |
| 6.2.2.6 | 6.2.2.7 | 6.2.2.8 | 6.2.2.9 | 6.2.3.1 | 6.2.3.2 | 6.2.3.3 | 6.2.3.4 | 6.2.3.5 | 6.2.3.6 |
| 6.2.3.7 | 6.2.3.8 | 6.2.3.9 | 6.2.4.1 | 6.2.4.2 | 6.2.4.3 | 6.2.4.4 | 6.2.4.5 | 6.2.4.6 | 6.2.4.7 |
| 6.2.4.8 | 6.2.4.9 | 6.2.5.1 | 6.2.5.2 | 6.2.5.3 | 6.2.5.4 | 6.2.5.5 | 6.2.5.6 | 6.2.5.7 | 6.2.5.8 |
| 6.2.5.9 | 6.2.6.1 | 6.2.6.2 | 6.2.6.3 | 6.2.6.4 | 6.2.6.5 | 6.2.6.6 | 6.2.6.7 | 6.2.6.8 | 6.2.6.9 |
| 6.2.7.1 | 6.2.7.2 | 6.2.7.3 | 6.2.7.4 | 6.2.7.5 | 6.2.7.6 | 6.2.7.7 | 6.2.7.8 | 6.2.7.9 | 6.2.8.1 |
| 6.2.8.2 | 6.2.8.3 | 6.2.8.4 | 6.2.8.5 | 6.2.8.6 | 6.2.8.7 | 6.2.8.8 | 6.2.8.9 | 6.2.9.1 | 6.2.9.2 |
| 6.2.9.3 | 6.2.9.4 | 6.2.9.5 | 6.2.9.6 | 6.2.9.7 | 6.2.9.8 | 6.2.9.9 | 6.3.1.1 | 6.3.1.2 | 6.3.1.3 |
| 6.3.1.4 | 6.3.1.5 | 6.3.1.6 | 6.3.1.7 | 6.3.1.8 | 6.3.1.9 | 6.3.2.1 | 6.3.2.2 | 6.3.2.3 | 6.3.2.4 |
| 6.3.2.5 | 6.3.2.6 | 6.3.2.7 | 6.3.2.8 | 6.3.2.9 | 6.3.3.1 | 6.3.3.2 | 6.3.3.3 | 6.3.3.4 | 6.3.3.5 |
| 6.3.3.6 | 6.3.3.7 | 6.3.3.8 | 6.3.3.9 | 6.3.4.1 | 6.3.4.2 | 6.3.4.3 | 6.3.4.4 | 6.3.4.5 | 6.3.4.6 |
| 6.3.4.7 | 6.3.4.8 | 6.3.4.9 | 6.3.5.1 | 6.3.5.2 | 6.3.5.3 | 6.3.5.4 | 6.3.5.5 | 6.3.5.6 | 6.3.5.7 |
| 6.3.5.8 | 6.3.5.9 | 6.3.6.1 | 6.3.6.2 | 6.3.6.3 | 6.3.6.4 | 6.3.6.5 | 6.3.6.6 | 6.3.6.7 | 6.3.6.8 |
| 6.3.6.9 | 6.3.7.1 | 6.3.7.2 | 6.3.7.3 | 6.3.7.4 | 6.3.7.5 | 6.3.7.6 | 6.3.7.7 | 6.3.7.8 | 6.3.7.9 |
| 6.3.8.1 | 6.3.8.2 | 6.3.8.3 | 6.3.8.4 | 6.3.8.5 | 6.3.8.6 | 6.3.8.7 | 6.3.8.8 | 6.3.8.9 | 6.3.9.1 |
| 6.3.9.2 | 6.3.9.3 | 6.3.9.4 | 6.3.9.5 | 6.3.9.6 | 6.3.9.7 | 6.3.9.8 | 6.3.9.9 | 6.4.1.1 | 6.4.1.2 |
| 6.4.1.3 | 6.4.1.4 | 6.4.1.5 | 6.4.1.6 | 6.4.1.7 | 6.4.1.8 | 6.4.1.9 | 6.4.2.1 | 6.4.2.2 | 6.4.2.3 |
| 6.4.2.4 | 6.4.2.5 | 6.4.2.6 | 6.4.2.7 | 6.4.2.8 | 6.4.2.9 | 6.4.3.1 | 6.4.3.2 | 6.4.3.3 | 6.4.3.4 |
| 6.4.3.5 | 6.4.3.6 | 6.4.3.7 | 6.4.3.8 | 6.4.3.9 | 6.4.4.1 | 6.4.4.2 | 6.4.4.3 | 6.4.4.4 | 6.4.4.5 |
| 6.4.4.6 | 6.4.4.7 | 6.4.4.8 | 6.4.4.9 | 6.4.5.1 | 6.4.5.2 | 6.4.5.3 | 6.4.5.4 | 6.4.5.5 | 6.4.5.6 |
| 6.4.5.7 | 6.4.5.8 | 6.4.5.9 | 6.4.6.1 | 6.4.6.2 | 6.4.6.3 | 6.4.6.4 | 6.4.6.5 | 6.4.6.6 | 6.4.6.7 |
| 6.4.6.8 | 6.4.6.9 | 6.4.7.1 | 6.4.7.2 | 6.4.7.3 | 6.4.7.4 | 6.4.7.5 | 6.4.7.6 | 6.4.7.7 | 6.4.7.8 |

TABLE 1-continued

| | | | | | | | | |
|---|---|---|---|---|---|---|---|---|
| 6.4.7.9 | 6.4.8.1 | 6.4.8.2 | 6.4.8.3 | 6.4.8.4 | 6.4.8.5 | 6.4.8.6 | 6.4.8.7 | 6.4.8.8 | 6.4.8.9 |
| 6.4.9.1 | 6.4.9.2 | 6.4.9.3 | 6.4.9.4 | 6.4.9.5 | 6.4.9.6 | 6.4.9.7 | 6.4.9.8 | 6.4.9.9 | 6.5.1.1 |
| 6.5.1.2 | 6.5.1.3 | 6.5.1.4 | 6.5.1.5 | 6.5.1.6 | 6.5.1.7 | 6.5.1.8 | 6.5.1.9 | 6.5.2.1 | 6.5.2.2 |
| 6.5.2.3 | 6.5.2.4 | 6.5.2.5 | 6.5.2.6 | 6.5.2.7 | 6.5.2.8 | 6.5.2.9 | 6.5.3.1 | 6.5.3.2 | 6.5.3.3 |
| 6.5.3.4 | 6.5.3.5 | 6.5.3.6 | 6.5.3.7 | 6.5.3.8 | 6.5.3.9 | 6.5.4.1 | 6.5.4.2 | 6.5.4.3 | 6.5.4.4 |
| 6.5.4.5 | 6.5.4.6 | 6.5.4.7 | 6.5.4.8 | 6.5.4.9 | 6.5.5.1 | 6.5.5.2 | 6.5.5.3 | 6.5.5.4 | 6.5.5.5 |
| 6.5.5.6 | 6.5.5.7 | 6.5.5.8 | 6.5.5.9 | 6.5.6.1 | 6.5.6.2 | 6.5.6.3 | 6.5.6.4 | 6.5.6.5 | 6.5.6.6 |
| 6.5.6.7 | 6.5.6.8 | 6.5.6.9 | 6.5.7.1 | 6.5.7.2 | 6.5.7.3 | 6.5.7.4 | 6.5.7.5 | 6.5.7.6 | 6.5.7.7 |
| 6.5.7.8 | 6.5.7.9 | 6.5.8.1 | 6.5.8.2 | 6.5.8.3 | 6.5.8.4 | 6.5.8.5 | 6.5.8.6 | 6.5.8.7 | 6.5.8.8 |
| 6.5.8.9 | 6.5.9.1 | 6.5.9.2 | 6.5.9.3 | 6.5.9.4 | 6.5.9.5 | 6.5.9.6 | 6.5.9.7 | 6.5.9.8 | 6.5.9.9 |
| 6.6.1.1 | 6.6.1.2 | 6.6.1.3 | 6.6.1.4 | 6.6.1.5 | 6.6.1.6 | 6.6.1.7 | 6.6.1.8 | 6.6.1.9 | 6.6.2.1 |
| 6.6.2.2 | 6.6.2.3 | 6.6.2.4 | 6.6.2.5 | 6.6.2.6 | 6.6.2.7 | 6.6.2.8 | 6.6.2.9 | 6.6.3.1 | 6.6.3.2 |
| 6.6.3.3 | 6.6.3.4 | 6.6.3.5 | 6.6.3.6 | 6.6.3.7 | 6.6.3.8 | 6.6.3.9 | 6.6.4.1 | 6.6.4.2 | 6.6.4.3 |
| 6.6.4.4 | 6.6.4.5 | 6.6.4.6 | 6.6.4.7 | 6.6.4.8 | 6.6.4.9 | 6.6.5.1 | 6.6.5.2 | 6.6.5.3 | 6.6.5.4 |
| 6.6.5.5 | 6.6.5.6 | 6.6.5.7 | 6.6.5.8 | 6.6.5.9 | 6.6.6.1 | 6.6.6.2 | 6.6.6.3 | 6.6.6.4 | 6.6.6.5 |
| 6.6.6.6 | 6.6.6.7 | 6.6.6.8 | 6.6.6.9 | 6.6.7.1 | 6.6.7.2 | 6.6.7.3 | 6.6.7.4 | 6.6.7.5 | 6.6.7.6 |
| 6.6.7.7 | 6.6.7.8 | 6.6.7.9 | 6.6.8.1 | 6.6.8.2 | 6.6.8.3 | 6.6.8.4 | 6.6.8.5 | 6.6.8.6 | 6.6.8.7 |
| 6.6.8.8 | 6.6.8.9 | 6.6.9.1 | 6.6.9.2 | 6.6.9.3 | 6.6.9.4 | 6.6.9.5 | 6.6.9.6 | 6.6.9.7 | 6.6.9.8 |
| 6.6.9.9 | 6.7.1.1 | 6.7.1.2 | 6.7.1.3 | 6.7.1.4 | 6.7.1.5 | 6.7.1.6 | 6.7.1.7 | 6.7.1.8 | 6.7.1.9 |
| 6.7.2.1 | 6.7.2.2 | 6.7.2.3 | 6.7.2.4 | 6.7.2.5 | 6.7.2.6 | 6.7.2.7 | 6.7.2.8 | 6.7.2.9 | 6.7.3.1 |
| 6.7.3.2 | 6.7.3.3 | 6.7.3.4 | 6.7.3.5 | 6.7.3.6 | 6.7.3.7 | 6.7.3.8 | 6.7.3.9 | 6.7.4.1 | 6.7.4.2 |
| 6.7.4.3 | 6.7.4.4 | 6.7.4.5 | 6.7.4.6 | 6.7.4.7 | 6.7.4.8 | 6.7.4.9 | 6.7.5.1 | 6.7.5.2 | 6.7.5.3 |
| 6.7.5.4 | 6.7.5.5 | 6.7.5.6 | 6.7.5.7 | 6.7.5.8 | 6.7.5.9 | 6.7.6.1 | 6.7.6.2 | 6.7.6.3 | 6.7.6.4 |
| 6.7.6.5 | 6.7.6.6 | 6.7.6.7 | 6.7.6.8 | 6.7.6.9 | 6.7.7.1 | 6.7.7.2 | 6.7.7.3 | 6.7.7.4 | 6.7.7.5 |
| 6.7.7.6 | 6.7.7.7 | 6.7.7.8 | 6.7.7.9 | 6.7.8.1 | 6.7.8.2 | 6.7.8.3 | 6.7.8.4 | 6.7.8.5 | 6.7.8.6 |
| 6.7.8.7 | 6.7.8.8 | 6.7.8.9 | 6.7.9.1 | 6.7.9.2 | 6.7.9.3 | 6.7.9.4 | 6.7.9.5 | 6.7.9.6 | 6.7.9.7 |
| 6.7.9.8 | 6.7.9.9 | 6.8.1.1 | 6.8.1.2 | 6.8.1.3 | 6.8.1.4 | 6.8.1.5 | 6.8.1.6 | 6.8.1.7 | 6.8.1.8 |
| 6.8.1.9 | 6.8.2.1 | 6.8.2.2 | 6.8.2.3 | 6.8.2.4 | 6.8.2.5 | 6.8.2.6 | 6.8.2.7 | 6.8.2.8 | 6.8.2.9 |
| 6.8.3.1 | 6.8.3.2 | 6.8.3.3 | 6.8.3.4 | 6.8.3.5 | 6.8.3.6 | 6.8.3.7 | 6.8.3.8 | 6.8.3.9 | 6.8.4.1 |
| 6.8.4.2 | 6.8.4.3 | 6.8.4.4 | 6.8.4.5 | 6.8.4.6 | 6.8.4.7 | 6.8.4.8 | 6.8.4.9 | 6.8.5.1 | 6.8.5.2 |
| 6.8.5.3 | 6.8.5.4 | 6.8.5.5 | 6.8.5.6 | 6.8.5.7 | 6.8.5.8 | 6.8.5.9 | 6.8.6.1 | 6.8.6.2 | 6.8.6.3 |
| 6.8.6.4 | 6.8.6.5 | 6.8.6.6 | 6.8.6.7 | 6.8.6.8 | 6.8.6.9 | 6.8.7.1 | 6.8.7.2 | 6.8.7.3 | 6.8.7.4 |
| 6.8.7.5 | 6.8.7.6 | 6.8.7.7 | 6.8.7.8 | 6.8.7.9 | 6.8.8.1 | 6.8.8.2 | 6.8.8.3 | 6.8.8.4 | 6.8.8.5 |
| 6.8.8.6 | 6.8.8.7 | 6.8.8.8 | 6.8.8.9 | 6.8.9.1 | 6.8.9.2 | 6.8.9.3 | 6.8.9.4 | 6.8.9.5 | 6.8.9.6 |
| 6.8.9.7 | 6.8.9.8 | 6.8.9.9 | 6.9.1.1 | 6.9.1.2 | 6.9.1.3 | 6.9.1.4 | 6.9.1.5 | 6.9.1.6 | 6.9.1.7 |
| 6.9.1.8 | 6.9.1.9 | 6.9.2.1 | 6.9.2.2 | 6.9.2.3 | 6.9.2.4 | 6.9.2.5 | 6.9.2.6 | 6.9.2.7 | 6.9.2.8 |
| 6.9.2.9 | 6.9.3.1 | 6.9.3.2 | 6.9.3.3 | 6.9.3.4 | 6.9.3.5 | 6.9.3.6 | 6.9.3.7 | 6.9.3.8 | 6.9.3.9 |
| 6.9.4.1 | 6.9.4.2 | 6.9.4.3 | 6.9.4.4 | 6.9.4.5 | 6.9.4.6 | 6.9.4.7 | 6.9.4.8 | 6.9.4.9 | 6.9.5.1 |
| 6.9.5.2 | 6.9.5.3 | 6.9.5.4 | 6.9.5.5 | 6.9.5.6 | 6.9.5.7 | 6.9.5.8 | 6.9.5.9 | 6.9.6.1 | 6.9.6.2 |
| 6.9.6.3 | 6.9.6.4 | 6.9.6.5 | 6.9.6.6 | 6.9.6.7 | 6.9.6.8 | 6.9.6.9 | 6.9.7.1 | 6.9.7.2 | 6.9.7.3 |
| 6.9.7.4 | 6.9.7.5 | 6.9.7.6 | 6.9.7.7 | 6.9.7.8 | 6.9.7.9 | 6.9.8.1 | 6.9.8.2 | 6.9.8.3 | 6.9.8.4 |
| 6.9.8.5 | 6.9.8.6 | 6.9.8.7 | 6.9.8.8 | 6.9.8.9 | 6.9.9.1 | 6.9.9.2 | 6.9.9.3 | 6.9.9.4 | 6.9.9.5 |
| 6.9.9.6 | 6.9.9.7 | 6.9.9.8 | 6.9.9.9 | 7.1.1.1 | 7.1.1.2 | 7.1.1.3 | 7.1.1.4 | 7.1.1.5 | 7.1.1.6 |
| 7.1.1.7 | 7.1.1.8 | 7.1.1.9 | 7.1.2.1 | 7.1.2.2 | 7.1.2.3 | 7.1.2.4 | 7.1.2.5 | 7.1.2.6 | 7.1.2.7 |
| 7.1.2.8 | 7.1.2.9 | 7.1.3.1 | 7.1.3.2 | 7.1.3.3 | 7.1.3.4 | 7.1.3.5 | 7.1.3.6 | 7.1.3.7 | 7.1.3.8 |
| 7.1.3.9 | 7.1.4.1 | 7.1.4.2 | 7.1.4.3 | 7.1.4.4 | 7.1.4.5 | 7.1.4.6 | 7.1.4.7 | 7.1.4.8 | 7.1.4.9 |
| 7.1.5.1 | 7.1.5.2 | 7.1.5.3 | 7.1.5.4 | 7.1.5.5 | 7.1.5.6 | 7.1.5.7 | 7.1.5.8 | 7.1.5.9 | 7.1.6.1 |
| 7.1.6.2 | 7.1.6.3 | 7.1.6.4 | 7.1.6.5 | 7.1.6.6 | 7.1.6.7 | 7.1.6.8 | 7.1.6.9 | 7.1.7.1 | 7.1.7.2 |
| 7.1.7.3 | 7.1.7.4 | 7.1.7.5 | 7.1.7.6 | 7.1.7.7 | 7.1.7.8 | 7.1.7.9 | 7.1.8.1 | 7.1.8.2 | 7.1.8.3 |
| 7.1.8.4 | 7.1.8.5 | 7.1.8.6 | 7.1.8.7 | 7.1.8.8 | 7.1.8.9 | 7.1.9.1 | 7.1.9.2 | 7.1.9.3 | 7.1.9.4 |
| 7.1.9.5 | 7.1.9.6 | 7.1.9.7 | 7.1.9.8 | 7.1.9.9 | 7.2.1.1 | 7.2.1.2 | 7.2.1.3 | 7.2.1.4 | 7.2.1.5 |
| 7.2.1.6 | 7.2.1.7 | 7.2.1.8 | 7.2.1.9 | 7.2.2.1 | 7.2.2.2 | 7.2.2.3 | 7.2.2.4 | 7.2.2.5 | 7.2.2.6 |
| 7.2.2.7 | 7.2.2.8 | 7.2.2.9 | 7.2.3.1 | 7.2.3.2 | 7.2.3.3 | 7.2.3.4 | 7.2.3.5 | 7.2.3.6 | 7.2.3.7 |
| 7.2.3.8 | 7.2.3.9 | 7.2.4.1 | 7.2.4.2 | 7.2.4.3 | 7.2.4.4 | 7.2.4.5 | 7.2.4.6 | 7.2.4.7 | 7.2.4.8 |
| 7.2.4.9 | 7.2.5.1 | 7.2.5.2 | 7.2.5.3 | 7.2.5.4 | 7.2.5.5 | 7.2.5.6 | 7.2.5.7 | 7.2.5.8 | 7.2.5.9 |
| 7.2.6.1 | 7.2.6.2 | 7.2.6.3 | 7.2.6.4 | 7.2.6.5 | 7.2.6.6 | 7.2.6.7 | 7.2.6.8 | 7.2.6.9 | 7.2.7.1 |
| 7.2.7.2 | 7.2.7.3 | 7.2.7.4 | 7.2.7.5 | 7.2.7.6 | 7.2.7.7 | 7.2.7.8 | 7.2.7.9 | 7.2.8.1 | 7.2.8.2 |
| 7.2.8.3 | 7.2.8.4 | 7.2.8.5 | 7.2.8.6 | 7.2.8.7 | 7.2.8.8 | 7.2.8.9 | 7.2.9.1 | 7.2.9.2 | 7.2.9.3 |
| 7.2.9.4 | 7.2.9.5 | 7.2.9.6 | 7.2.9.7 | 7.2.9.8 | 7.2.9.9 | 7.3.1.1 | 7.3.1.2 | 7.3.1.3 | 7.3.1.4 |
| 7.3.1.5 | 7.3.1.6 | 7.3.1.7 | 7.3.1.8 | 7.3.1.9 | 7.3.2.1 | 7.3.2.2 | 7.3.2.3 | 7.3.2.4 | 7.3.2.5 |
| 7.3.2.6 | 7.3.2.7 | 7.3.2.8 | 7.3.2.9 | 7.3.3.1 | 7.3.3.2 | 7.3.3.3 | 7.3.3.4 | 7.3.3.5 | 7.3.3.6 |
| 7.3.3.7 | 7.3.3.8 | 7.3.3.9 | 7.3.4.1 | 7.3.4.2 | 7.3.4.3 | 7.3.4.4 | 7.3.4.5 | 7.3.4.6 | 7.3.4.7 |
| 7.3.4.8 | 7.3.4.9 | 7.3.5.1 | 7.3.5.2 | 7.3.5.3 | 7.3.5.4 | 7.3.5.5 | 7.3.5.6 | 7.3.5.7 | 7.3.5.8 |
| 7.3.5.9 | 7.3.6.1 | 7.3.6.2 | 7.3.6.3 | 7.3.6.4 | 7.3.6.5 | 7.3.6.6 | 7.3.6.7 | 7.3.6.8 | 7.3.6.9 |
| 7.3.7.1 | 7.3.7.2 | 7.3.7.3 | 7.3.7.4 | 7.3.7.5 | 7.3.7.6 | 7.3.7.7 | 7.3.7.8 | 7.3.7.9 | 7.3.8.1 |
| 7.3.8.2 | 7.3.8.3 | 7.3.8.4 | 7.3.8.5 | 7.3.8.6 | 7.3.8.7 | 7.3.8.8 | 7.3.8.9 | 7.3.9.1 | 7.3.9.2 |
| 7.3.9.3 | 7.3.9.4 | 7.3.9.5 | 7.3.9.6 | 7.3.9.7 | 7.3.9.8 | 7.3.9.9 | 7.4.1.1 | 7.4.1.2 | 7.4.1.3 |
| 7.4.1.4 | 7.4.1.5 | 7.4.1.6 | 7.4.1.7 | 7.4.1.8 | 7.4.1.9 | 7.4.2.1 | 7.4.2.2 | 7.4.2.3 | 7.4.2.4 |
| 7.4.2.5 | 7.4.2.6 | 7.4.2.7 | 7.4.2.8 | 7.4.2.9 | 7.4.3.1 | 7.4.3.2 | 7.4.3.3 | 7.4.3.4 | 7.4.3.5 |
| 7.4.3.6 | 7.4.3.7 | 7.4.3.8 | 7.4.3.9 | 7.4.4.1 | 7.4.4.2 | 7.4.4.3 | 7.4.4.4 | 7.4.4.5 | 7.4.4.6 |
| 7.4.4.7 | 7.4.4.8 | 7.4.4.9 | 7.4.5.1 | 7.4.5.2 | 7.4.5.3 | 7.4.5.4 | 7.4.5.5 | 7.4.5.6 | 7.4.5.7 |
| 7.4.5.8 | 7.4.5.9 | 7.4.6.1 | 7.4.6.2 | 7.4.6.3 | 7.4.6.4 | 7.4.6.5 | 7.4.6.6 | 7.4.6.7 | 7.4.6.8 |
| 7.4.6.9 | 7.4.7.1 | 7.4.7.2 | 7.4.7.3 | 7.4.7.4 | 7.4.7.5 | 7.4.7.6 | 7.4.7.7 | 7.4.7.8 | 7.4.7.9 |
| 7.4.8.1 | 7.4.8.2 | 7.4.8.3 | 7.4.8.4 | 7.4.8.5 | 7.4.8.6 | 7.4.8.7 | 7.4.8.8 | 7.4.8.9 | 7.4.9.1 |
| 7.4.9.2 | 7.4.9.3 | 7.4.9.4 | 7.4.9.5 | 7.4.9.6 | 7.4.9.7 | 7.4.9.8 | 7.4.9.9 | 7.5.1.1 | 7.5.1.2 |
| 7.5.1.3 | 7.5.1.4 | 7.5.1.5 | 7.5.1.6 | 7.5.1.7 | 7.5.1.8 | 7.5.1.9 | 7.5.2.1 | 7.5.2.2 | 7.5.2.3 |
| 7.5.2.4 | 7.5.2.5 | 7.5.2.6 | 7.5.2.7 | 7.5.2.8 | 7.5.2.9 | 7.5.3.1 | 7.5.3.2 | 7.5.3.3 | 7.5.3.4 |
| 7.5.3.5 | 7.5.3.6 | 7.5.3.7 | 7.5.3.8 | 7.5.3.9 | 7.5.4.1 | 7.5.4.2 | 7.5.4.3 | 7.5.4.4 | 7.5.4.5 |
| 7.5.4.6 | 7.5.4.7 | 7.5.4.8 | 7.5.4.9 | 7.5.5.1 | 7.5.5.2 | 7.5.5.3 | 7.5.5.4 | 7.5.5.5 | 7.5.5.6 |

TABLE 1-continued

| | | | | | | | | | |
|---|---|---|---|---|---|---|---|---|---|
| 7.5.5.7 | 7.5.5.8 | 7.5.5.9 | 7.5.6.1 | 7.5.6.2 | 7.5.6.3 | 7.5.6.4 | 7.5.6.5 | 7.5.6.6 | 7.5.6.7 |
| 7.5.6.8 | 7.5.6.9 | 7.5.7.1 | 7.5.7.2 | 7.5.7.3 | 7.5.7.4 | 7.5.7.5 | 7.5.7.6 | 7.5.7.7 | 7.5.7.8 |
| 7.5.7.9 | 7.5.8.1 | 7.5.8.2 | 7.5.8.3 | 7.5.8.4 | 7.5.8.5 | 7.5.8.6 | 7.5.8.7 | 7.5.8.8 | 7.5.8.9 |
| 7.5.9.1 | 7.5.9.2 | 7.5.9.3 | 7.5.9.4 | 7.5.9.5 | 7.5.9.6 | 7.5.9.7 | 7.5.9.8 | 7.5.9.9 | 7.6.1.1 |
| 7.6.1.2 | 7.6.1.3 | 7.6.1.4 | 7.6.1.5 | 7.6.1.6 | 7.6.1.7 | 7.6.1.8 | 7.6.1.9 | 7.6.2.1 | 7.6.2.2 |
| 7.6.2.3 | 7.6.2.4 | 7.6.2.5 | 7.6.2.6 | 7.6.2.7 | 7.6.2.8 | 7.6.2.9 | 7.6.3.1 | 7.6.3.2 | 7.6.3.3 |
| 7.6.3.4 | 7.6.3.5 | 7.6.3.6 | 7.6.3.7 | 7.6.3.8 | 7.6.3.9 | 7.6.4.1 | 7.6.4.2 | 7.6.4.3 | 7.6.4.4 |
| 7.6.4.5 | 7.6.4.6 | 7.6.4.7 | 7.6.4.8 | 7.6.4.9 | 7.6.5.1 | 7.6.5.2 | 7.6.5.3 | 7.6.5.4 | 7.6.5.5 |
| 7.6.5.6 | 7.6.5.7 | 7.6.5.8 | 7.6.5.9 | 7.6.6.1 | 7.6.6.2 | 7.6.6.3 | 7.6.6.4 | 7.6.6.5 | 7.6.6.6 |
| 7.6.6.7 | 7.6.6.8 | 7.6.6.9 | 7.6.7.1 | 7.6.7.2 | 7.6.7.3 | 7.6.7.4 | 7.6.7.5 | 7.6.7.6 | 7.6.7.7 |
| 7.6.7.8 | 7.6.7.9 | 7.6.8.1 | 7.6.8.2 | 7.6.8.3 | 7.6.8.4 | 7.6.8.5 | 7.6.8.6 | 7.6.8.7 | 7.6.8.8 |
| 7.6.8.9 | 7.6.9.1 | 7.6.9.2 | 7.6.9.3 | 7.6.9.4 | 7.6.9.5 | 7.6.9.6 | 7.6.9.7 | 7.6.9.8 | 7.6.9.9 |
| 7.7.1.1 | 7.7.1.2 | 7.7.1.3 | 7.7.1.4 | 7.7.1.5 | 7.7.1.6 | 7.7.1.7 | 7.7.1.8 | 7.7.1.9 | 7.7.2.1 |
| 7.7.2.2 | 7.7.2.3 | 7.7.2.4 | 7.7.2.5 | 7.7.2.6 | 7.7.2.7 | 7.7.2.8 | 7.7.2.9 | 7.7.3.1 | 7.7.3.2 |
| 7.7.3.3 | 7.7.3.4 | 7.7.3.5 | 7.7.3.6 | 7.7.3.7 | 7.7.3.8 | 7.7.3.9 | 7.7.4.1 | 7.7.4.2 | 7.7.4.3 |
| 7.7.4.4 | 7.7.4.5 | 7.7.4.6 | 7.7.4.7 | 7.7.4.8 | 7.7.4.9 | 7.7.5.1 | 7.7.5.2 | 7.7.5.3 | 7.7.5.4 |
| 7.7.5.5 | 7.7.5.6 | 7.7.5.7 | 7.7.5.8 | 7.7.5.9 | 7.7.6.1 | 7.7.6.2 | 7.7.6.3 | 7.7.6.4 | 7.7.6.5 |
| 7.7.6.6 | 7.7.6.7 | 7.7.6.8 | 7.7.6.9 | 7.7.7.1 | 7.7.7.2 | 7.7.7.3 | 7.7.7.4 | 7.7.7.5 | 7.7.7.6 |
| 7.7.7.7 | 7.7.7.8 | 7.7.7.9 | 7.7.8.1 | 7.7.8.2 | 7.7.8.3 | 7.7.8.4 | 7.7.8.5 | 7.7.8.6 | 7.7.8.7 |
| 7.7.8.8 | 7.7.8.9 | 7.7.9.1 | 7.7.9.2 | 7.7.9.3 | 7.7.9.4 | 7.7.9.5 | 7.7.9.6 | 7.7.9.7 | 7.7.9.8 |
| 7.7.9.9 | 7.8.1.1 | 7.8.1.2 | 7.8.1.3 | 7.8.1.4 | 7.8.1.5 | 7.8.1.6 | 7.8.1.7 | 7.8.1.8 | 7.8.1.9 |
| 7.8.2.1 | 7.8.2.2 | 7.8.2.3 | 7.8.2.4 | 7.8.2.5 | 7.8.2.6 | 7.8.2.7 | 7.5.2.8 | 7.8.2.9 | 7.8.3.1 |
| 7.8.3.2 | 7.8.3.3 | 7.8.3.4 | 7.8.3.5 | 7.8.3.6 | 7.8.3.7 | 7.8.3.8 | 7.8.3.9 | 7.8.4.1 | 7.8.4.2 |
| 7.8.4.3 | 7.8.4.4 | 7.8.4.5 | 7.8.4.6 | 7.8.4.7 | 7.8.4.8 | 7.8.4.9 | 7.8.5.1 | 7.8.5.2 | 7.8.5.3 |
| 7.8.5.4 | 7.8.5.5 | 7.8.5.6 | 7.8.5.7 | 7.8.5.8 | 7.8.5.9 | 7.8.6.1 | 7.8.6.2 | 7.8.6.3 | 7.8.6.4 |
| 7.8.6.5 | 7.8.6.6 | 7.8.6.7 | 7.8.6.8 | 7.8.6.9 | 7.8.7.1 | 7.8.7.2 | 7.8.7.3 | 7.8.7.4 | 7.8.7.5 |
| 7.8.7.6 | 7.8.7.7 | 7.8.7.8 | 7.8.7.9 | 7.8.8.1 | 7.8.8.2 | 7.8.8.3 | 7.8.8.4 | 7.8.8.5 | 7.8.8.6 |
| 7.8.8.7 | 7.8.8.8 | 7.8.8.9 | 7.8.9.1 | 7.8.9.2 | 7.8.9.3 | 7.8.9.4 | 7.8.9.5 | 7.8.9.6 | 7.8.9.7 |
| 7.8.9.8 | 7.8.9.9 | 7.9.1.1 | 7.9.1.2 | 7.9.1.3 | 7.9.1.4 | 7.9.1.5 | 7.9.1.6 | 7.9.1.7 | 7.9.1.8 |
| 7.9.1.9 | 7.9.2.1 | 7.9.2.2 | 7.9.2.3 | 7.9.2.4 | 7.9.2.5 | 7.9.2.6 | 7.9.2.7 | 7.9.2.8 | 7.9.2.9 |
| 7.9.3.1 | 7.9.3.2 | 7.9.3.3 | 7.9.3.4 | 7.9.3.5 | 7.9.3.6 | 7.9.3.7 | 7.9.3.8 | 7.9.3.9 | 7.9.4.1 |
| 7.9.4.2 | 7.9.4.3 | 7.9.4.4 | 7.9.4.5 | 7.9.4.6 | 7.9.4.7 | 7.9.4.8 | 7.9.4.9 | 7.9.5.1 | 7.9.5.2 |
| 7.9.5.3 | 7.9.5.4 | 7.9.5.5 | 7.9.5.6 | 7.9.5.7 | 7.9.5.8 | 7.9.5.9 | 7.9.6.1 | 7.9.6.2 | 7.9.6.3 |
| 7.9.6.4 | 7.9.6.5 | 7.9.6.6 | 7.9.6.7 | 7.9.6.8 | 7.9.6.9 | 7.9.7.1 | 7.9.7.2 | 7.9.7.3 | 7.9.7.4 |
| 7.9.7.5 | 7.9.7.6 | 7.9.7.7 | 7.9.7.8 | 7.9.7.9 | 7.9.8.1 | 7.9.8.2 | 7.9.8.3 | 7.9.8.4 | 7.9.8.5 |
| 7.9.8.6 | 7.9.8.7 | 7.9.8.8 | 7.9.8.9 | 7.9.9.1 | 7.9.9.2 | 7.9.9.3 | 7.9.9.4 | 7.9.9.5 | 7.9.9.6 |
| 7.9.9.7 | 7.9.9.8 | 7.9.9.9 | 8.1.1.1 | 8.1.1.2 | 8.1.1.3 | 8.1.1.4 | 8.1.1.5 | 8.1.1.6 | 8.1.1.7 |
| 8.1.1.8 | 8.1.1.9 | 8.1.2.1 | 8.1.2.2 | 8.1.2.3 | 8.1.2.4 | 8.1.2.5 | 8.1.2.6 | 8.1.2.7 | 8.1.2.8 |
| 8.1.2.9 | 8.1.3.1 | 8.1.3.2 | 8.1.3.3 | 8.1.3.4 | 8.1.3.5 | 8.1.3.6 | 8.1.3.7 | 8.1.3.8 | 8.1.3.9 |
| 8.1.4.1 | 8.1.4.2 | 8.1.4.3 | 8.1.4.4 | 8.1.4.5 | 8.1.4.6 | 8.1.4.7 | 8.1.4.8 | 8.1.4.9 | 8.1.5.1 |
| 8.1.5.2 | 8.1.5.3 | 8.1.5.4 | 8.1.5.5 | 8.1.5.6 | 8.1.5.7 | 8.1.5.8 | 8.1.5.9 | 8.1.6.1 | 8.1.6.2 |
| 8.1.6.3 | 8.1.6.4 | 8.1.6.5 | 8.1.6.6 | 8.1.6.7 | 8.1.6.8 | 8.1.6.9 | 8.1.7.1 | 8.1.7.2 | 8.1.7.3 |
| 8.1.7.4 | 8.1.7.5 | 8.1.7.6 | 8.1.7.7 | 8.1.7.8 | 8.1.7.9 | 8.1.8.1 | 8.1.8.2 | 8.1.8.3 | 8.1.8.4 |
| 8.1.8.5 | 8.1.8.6 | 8.1.8.7 | 8.1.8.8 | 8.1.8.9 | 8.1.9.1 | 8.1.9.2 | 8.1.9.3 | 8.1.9.4 | 8.1.9.5 |
| 8.1.9.6 | 8.1.9.7 | 8.1.9.8 | 8.1.9.9 | 8.2.1.1 | 8.2.1.2 | 8.2.1.3 | 8.2.1.4 | 8.2.1.5 | 8.2.1.6 |
| 8.2.1.7 | 8.2.1.8 | 8.2.1.9 | 8.2.2.1 | 8.2.2.2 | 8.2.2.3 | 8.2.2.4 | 8.2.2.5 | 8.2.2.6 | 8.2.2.7 |
| 8.2.2.8 | 8.2.2.9 | 8.2.3.1 | 8.2.3.2 | 8.2.3.3 | 8.2.3.4 | 8.2.3.5 | 8.2.3.6 | 8.2.3.7 | 8.2.3.8 |
| 8.2.3.9 | 8.2.4.1 | 8.2.4.2 | 8.2.4.3 | 8.2.4.4 | 8.2.4.5 | 8.2.4.6 | 8.2.4.7 | 8.2.4.8 | 8.2.4.9 |
| 8.2.5.1 | 8.2.5.2 | 8.2.5.3 | 8.2.5.4 | 8.2.5.5 | 8.2.5.6 | 8.2.5.7 | 8.2.5.8 | 8.2.5.9 | 8.2.6.1 |
| 8.2.6.2 | 8.2.6.3 | 8.2.6.4 | 8.2.6.5 | 8.2.6.6 | 8.2.6.7 | 8.2.6.8 | 8.2.6.9 | 8.2.7.1 | 8.2.7.2 |
| 8.2.7.3 | 8.2.7.4 | 8.2.7.5 | 8.2.7.6 | 8.2.7.7 | 8.2.7.8 | 8.2.7.9 | 8.2.8.1 | 8.2.8.2 | 8.2.8.3 |
| 8.2.8.4 | 8.2.8.5 | 8.2.8.6 | 8.2.8.7 | 8.2.8.8 | 8.2.8.9 | 8.2.9.1 | 8.2.9.2 | 8.2.9.3 | 8.2.9.4 |
| 8.2.9.5 | 8.2.9.6 | 8.2.9.7 | 8.2.9.8 | 8.2.9.9 | 8.3.1.1 | 8.3.1.2 | 8.3.1.3 | 8.3.1.4 | 8.3.1.5 |
| 8.3.1.6 | 8.3.1.7 | 8.3.1.8 | 8.3.1.9 | 8.3.2.1 | 8.3.2.2 | 8.3.2.3 | 8.3.2.4 | 8.3.2.5 | 8.3.2.6 |
| 8.3.2.7 | 8.3.2.8 | 8.3.2.9 | 8.3.3.1 | 8.3.3.2 | 8.3.3.3 | 8.3.3.4 | 8.3.3.5 | 8.3.3.6 | 8.3.3.7 |
| 8.3.3.8 | 8.3.3.9 | 8.3.4.1 | 8.3.4.2 | 8.3.4.3 | 8.3.4.4 | 8.3.4.5 | 8.3.4.6 | 8.3.4.7 | 8.3.4.8 |
| 8.3.4.9 | 8.3.5.1 | 8.3.5.2 | 8.3.5.3 | 8.3.5.4 | 8.3.5.5 | 8.3.5.6 | 8.3.5.7 | 8.3.5.8 | 8.3.5.9 |
| 8.3.6.1 | 8.3.6.2 | 8.3.6.3 | 8.3.6.4 | 8.3.6.5 | 8.3.6.6 | 8.3.6.7 | 8.3.6.8 | 8.3.6.9 | 8.3.7.1 |
| 8.3.7.2 | 8.3.7.3 | 8.3.7.4 | 8.3.7.5 | 8.3.7.6 | 8.3.7.7 | 8.3.7.8 | 8.3.7.9 | 8.3.8.1 | 8.3.8.2 |
| 8.3.8.3 | 8.3.8.4 | 8.3.8.5 | 8.3.8.6 | 8.3.8.7 | 8.3.8.8 | 8.3.8.9 | 8.3.9.1 | 8.3.9.2 | 8.3.9.3 |
| 8.3.9.4 | 8.3.9.5 | 8.3.9.6 | 8.3.9.7 | 8.3.9.8 | 8.3.9.9 | 8.4.1.1 | 8.4.1.2 | 8.4.1.3 | 8.4.1.4 |
| 8.4.1.5 | 8.4.1.6 | 8.4.1.7 | 8.4.1.8 | 8.4.1.9 | 8.4.2.1 | 8.4.2.2 | 8.4.2.3 | 8.4.2.4 | 8.4.2.5 |
| 8.4.2.6 | 8.4.2.7 | 8.4.2.8 | 8.4.2.9 | 8.4.3.1 | 8.4.3.2 | 8.4.3.3 | 8.4.3.4 | 8.4.3.5 | 8.4.3.6 |
| 8.4.3.7 | 8.4.3.8 | 8.4.3.9 | 8.4.4.1 | 8.4.4.2 | 8.4.4.3 | 8.4.4.4 | 8.4.4.5 | 8.4.4.6 | 8.4.4.7 |
| 8.4.4.8 | 8.4.4.9 | 8.4.5.1 | 8.4.5.2 | 8.4.5.3 | 8.4.5.4 | 8.4.5.5 | 8.4.5.6 | 8.4.5.7 | 8.4.5.8 |
| 8.4.5.9 | 8.4.6.1 | 8.4.6.2 | 8.4.6.3 | 8.4.6.4 | 8.4.6.5 | 8.4.6.6 | 8.4.6.7 | 8.4.6.8 | 8.4.6.9 |
| 8.4.7.1 | 8.4.7.2 | 8.4.7.3 | 8.4.7.4 | 8.4.7.5 | 8.4.7.6 | 8.4.7.7 | 8.4.7.8 | 8.4.7.9 | 8.4.8.1 |
| 8.4.8.2 | 8.4.8.3 | 8.4.8.4 | 8.4.8.5 | 8.4.8.6 | 8.4.8.7 | 8.4.8.8 | 8.4.8.9 | 8.4.9.1 | 8.4.9.2 |
| 8.4.9.3 | 8.4.9.4 | 8.4.9.5 | 8.4.9.6 | 8.4.9.7 | 8.4.9.8 | 8.4.9.9 | 8.5.1.1 | 8.5.1.2 | 8.5.1.3 |
| 8.5.1.4 | 8.5.1.5 | 8.5.1.6 | 8.5.1.7 | 8.5.1.8 | 8.5.1.9 | 8.5.2.1 | 8.5.2.2 | 8.5.2.3 | 8.5.2.4 |
| 8.5.2.5 | 8.5.2.6 | 8.5.2.7 | 8.5.2.8 | 8.5.2.9 | 8.5.3.1 | 8.5.3.2 | 8.5.3.3 | 8.5.3.4 | 8.5.3.5 |
| 8.5.3.6 | 8.5.3.7 | 8.5.3.8 | 8.5.3.9 | 8.5.4.1 | 8.5.4.2 | 8.5.4.3 | 8.5.4.4 | 8.5.4.5 | 8.5.4.6 |
| 8.5.4.7 | 8.5.4.8 | 8.5.4.9 | 8.5.5.1 | 8.5.5.2 | 8.5.5.3 | 8.5.5.4 | 8.5.5.5 | 8.5.5.6 | 8.5.5.7 |
| 8.5.5.8 | 8.5.5.9 | 8.5.6.1 | 8.5.6.2 | 8.5.6.3 | 8.5.6.4 | 8.5.6.5 | 8.5.6.6 | 8.5.6.7 | 8.5.6.8 |
| 8.5.6.9 | 8.5.7.1 | 8.5.7.2 | 8.5.7.3 | 8.5.7.4 | 8.5.7.5 | 8.5.7.6 | 8.5.7.7 | 8.5.7.8 | 8.5.7.9 |
| 8.5.8.1 | 8.5.8.2 | 8.5.8.3 | 8.5.8.4 | 8.5.8.5 | 8.5.8.6 | 8.5.8.7 | 8.5.8.8 | 8.5.8.9 | 8.5.9.1 |
| 8.5.9.2 | 8.5.9.3 | 8.5.9.4 | 8.5.9.5 | 8.5.9.6 | 8.5.9.7 | 8.5.9.8 | 8.5.9.9 | 8.6.1.1 | 8.6.1.2 |
| 8.6.1.3 | 8.6.1.4 | 8.6.1.5 | 8.6.1.6 | 8.6.1.7 | 8.6.1.8 | 8.6.1.9 | 8.6.2.1 | 8.6.2.2 | 8.6.2.3 |
| 8.6.2.4 | 8.6.2.5 | 8.6.2.6 | 8.6.2.7 | 8.6.2.8 | 8.6.2.9 | 8.6.3.1 | 8.6.3.2 | 8.6.3.3 | 8.6.3.4 |

TABLE 1-continued

| | | | | | | | | | |
|---|---|---|---|---|---|---|---|---|---|
| 8.6.3.5 | 8.6.3.6 | 8.6.3.7 | 8.6.3.8 | 8.6.3.9 | 8.6.4.1 | 8.6.4.2 | 8.6.4.3 | 8.6.4.4 | 8.6.4.5 |
| 8.6.4.6 | 8.6.4.7 | 8.6.4.8 | 8.6.4.9 | 8.6.5.1 | 8.6.5.2 | 8.6.5.3 | 8.6.5.4 | 8.6.5.5 | 8.6.5.6 |
| 8.6.5.7 | 8.6.5.8 | 8.6.5.9 | 8.6.6.1 | 8.6.6.2 | 8.6.6.3 | 8.6.6.4 | 8.6.6.5 | 8.6.6.6 | 8.6.6.7 |
| 8.6.6.8 | 8.6.6.9 | 8.6.7.1 | 8.6.7.2 | 8.6.7.3 | 8.6.7.4 | 8.6.7.5 | 8.6.7.6 | 8.6.7.7 | 8.6.7.8 |
| 8.6.7.9 | 8.6.8.1 | 8.6.8.2 | 8.6.8.3 | 8.6.8.4 | 8.6.8.5 | 8.6.8.6 | 8.6.8.7 | 8.6.8.8 | 8.6.8.9 |
| 8.6.9.1 | 8.6.9.2 | 8.6.9.3 | 8.6.9.4 | 8.6.9.5 | 8.6.9.6 | 8.6.9.7 | 8.6.9.8 | 8.6.9.9 | 8.7.1.1 |
| 8.7.1.2 | 8.7.1.3 | 8.7.1.4 | 8.7.1.5 | 8.7.1.6 | 8.7.1.7 | 8.7.1.8 | 8.7.1.9 | 8.7.2.1 | 8.7.2.2 |
| 8.7.2.3 | 8.7.2.4 | 8.7.2.5 | 8.7.2.6 | 8.7.2.7 | 8.7.2.8 | 8.7.2.9 | 8.7.3.1 | 8.7.3.2 | 8.7.3.3 |
| 8.7.3.4 | 8.7.3.5 | 8.7.3.6 | 8.7.3.7 | 8.7.3.8 | 8.7.3.9 | 8.7.4.1 | 8.7.4.2 | 8.7.4.3 | 8.7.4.4 |
| 8.7.4.5 | 8.7.4.6 | 8.7.4.7 | 8.7.4.8 | 8.7.4.9 | 8.7.5.1 | 8.7.5.2 | 8.7.5.3 | 8.7.5.4 | 8.7.5.5 |
| 8.7.5.6 | 8.7.5.7 | 8.7.5.8 | 8.7.5.9 | 8.7.6.1 | 8.7.6.2 | 8.7.6.3 | 8.7.6.4 | 8.7.6.5 | 8.7.6.6 |
| 8.7.6.7 | 8.7.6.8 | 8.7.6.9 | 8.7.7.1 | 8.7.7.2 | 8.7.7.3 | 8.7.7.4 | 8.7.7.5 | 8.7.7.6 | 8.7.7.7 |
| 8.7.7.8 | 8.7.7.9 | 8.7.8.1 | 8.7.8.2 | 8.7.8.3 | 8.7.8.4 | 8.7.8.5 | 8.7.8.6 | 8.7.8.7 | 8.7.8.8 |
| 8.7.8.9 | 8.7.9.1 | 8.7.9.2 | 8.7.9.3 | 8.7.9.4 | 8.7.9.5 | 8.7.9.6 | 8.7.9.7 | 8.7.9.8 | 8.7.9.9 |
| 8.8.1.1 | 8.8.1.2 | 8.8.1.3 | 8.8.1.4 | 8.8.1.5 | 8.8.1.6 | 8.8.1.7 | 8.8.1.8 | 8.8.1.9 | 8.8.2.1 |
| 8.8.2.2 | 8.8.2.3 | 8.8.2.4 | 8.8.2.5 | 8.8.2.6 | 8.8.2.7 | 8.8.2.8 | 8.8.2.9 | 8.8.3.1 | 8.8.3.2 |
| 8.8.3.3 | 8.8.3.4 | 8.8.3.5 | 8.8.3.6 | 8.8.3.7 | 8.8.3.8 | 8.8.3.9 | 8.8.4.1 | 8.8.4.2 | 8.8.4.3 |
| 8.8.4.4 | 8.8.4.5 | 8.8.4.6 | 8.8.4.7 | 8.8.4.8 | 8.8.4.9 | 8.8.5.1 | 8.8.5.2 | 8.8.5.3 | 8.8.5.4 |
| 8.8.5.5 | 8.8.5.6 | 8.8.5.7 | 8.8.5.8 | 8.8.5.9 | 8.8.6.1 | 8.8.6.2 | 8.8.6.3 | 8.8.6.4 | 8.8.6.5 |
| 8.8.6.6 | 8.8.6.7 | 8.8.6.8 | 8.8.6.9 | 8.8.7.1 | 8.8.7.2 | 8.8.7.3 | 8.8.7.4 | 8.8.7.5 | 8.8.7.6 |
| 8.8.7.7 | 8.8.7.8 | 8.8.7.9 | 8.8.8.1 | 8.8.8.2 | 8.8.8.3 | 8.8.8.4 | 8.8.8.5 | 8.8.8.6 | 8.8.8.7 |
| 8.8.8.8 | 8.8.8.9 | 8.8.9.1 | 8.8.9.2 | 8.8.9.3 | 8.8.9.4 | 8.8.9.5 | 8.8.9.6 | 8.8.9.7 | 8.8.9.8 |
| 8.8.9.9 | 8.9.1.1 | 8.9.1.2 | 8.9.1.3 | 8.9.1.4 | 8.9.1.5 | 8.9.1.6 | 8.9.1.7 | 8.9.1.8 | 8.9.1.9 |
| 8.9.2.1 | 8.9.2.2 | 8.9.2.3 | 8.9.2.4 | 8.9.2.5 | 8.9.2.6 | 8.9.2.7 | 8.9.2.8 | 8.9.2.9 | 8.9.3.1 |
| 8.9.3.2 | 8.9.3.3 | 8.9.3.4 | 8.9.3.5 | 8.9.3.6 | 8.9.3.7 | 8.9.3.8 | 8.9.3.9 | 8.9.4.1 | 8.9.4.2 |
| 8.9.4.3 | 8.9.4.4 | 8.9.4.5 | 8.9.4.6 | 8.9.4.7 | 8.9.4.8 | 8.9.4.9 | 8.9.5.1 | 8.9.5.2 | 8.9.5.3 |
| 8.9.5.4 | 8.9.5.5 | 8.9.5.6 | 8.9.5.7 | 8.9.5.8 | 8.9.5.9 | 8.9.6.1 | 8.9.6.2 | 8.9.6.3 | 8.9.6.4 |
| 8.9.6.5 | 8.9.6.6 | 8.9.6.7 | 8.9.6.8 | 8.9.6.9 | 8.9.7.1 | 8.9.7.2 | 8.9.7.3 | 8.9.7.4 | 8.9.7.5 |
| 8.9.7.6 | 8.9.7.7 | 8.9.7.8 | 8.9.7.9 | 8.9.8.1 | 8.9.8.2 | 8.9.8.3 | 8.9.8.4 | 8.9.8.5 | 8.9.8.6 |
| 8.9.8.7 | 8.9.8.8 | 8.9.8.9 | 8.9.9.1 | 8.9.9.2 | 8.9.9.3 | 8.9.9.4 | 8.9.9.5 | 8.9.9.6 | 8.9.9.7 |
| 8.9.9.8 | 8.9.9.9 | 9.1.1.1 | 9.1.1.2 | 9.1.1.3 | 9.1.1.4 | 9.1.1.5 | 9.1.1.6 | 9.1.1.7 | 9.1.1.8 |
| 9.1.1.9 | 9.1.2.1 | 9.1.2.2 | 9.1.2.3 | 9.1.2.4 | 9.1.2.5 | 9.1.2.6 | 9.1.2.7 | 9.1.2.8 | 9.1.2.9 |
| 9.1.3.1 | 9.1.3.2 | 9.1.3.3 | 9.1.3.4 | 9.1.3.5 | 9.1.3.6 | 9.1.3.7 | 9.1.3.8 | 9.1.3.9 | 9.1.4.1 |
| 9.1.4.2 | 9.1.4.3 | 9.1.4.4 | 9.1.4.5 | 9.1.4.6 | 9.1.4.7 | 9.1.4.8 | 9.1.4.9 | 9.1.5.1 | 9.1.5.2 |
| 9.1.5.3 | 9.1.5.4 | 9.1.5.5 | 9.1.5.6 | 9.1.5.7 | 9.1.5.8 | 9.1.5.9 | 9.1.6.1 | 9.1.6.2 | 9.1.6.3 |
| 9.1.6.4 | 9.1.6.5 | 9.1.6.6 | 9.1.6.7 | 9.1.6.8 | 9.1.6.9 | 9.1.7.1 | 9.1.7.2 | 9.1.7.3 | 9.1.7.4 |
| 9.1.7.5 | 9.1.7.6 | 9.1.7.7 | 9.1.7.8 | 9.1.7.9 | 9.1.8.1 | 9.1.8.2 | 9.1.8.3 | 9.1.8.4 | 9.1.8.5 |
| 9.1.8.6 | 9.1.8.7 | 9.1.8.8 | 9.1.8.9 | 9.1.9.1 | 9.1.9.2 | 9.1.9.3 | 9.1.9.4 | 9.1.9.5 | 9.1.9.6 |
| 9.1.9.7 | 9.1.9.8 | 9.1.9.9 | 9.2.1.1 | 9.2.1.2 | 9.2.1.3 | 9.2.1.4 | 9.2.1.5 | 9.2.1.6 | 9.2.1.7 |
| 9.2.1.8 | 9.2.1.9 | 9.2.2.1 | 9.2.2.2 | 9.2.2.3 | 9.2.2.4 | 9.2.2.5 | 9.2.2.6 | 9.2.2.7 | 9.2.2.8 |
| 9.2.2.9 | 9.2.3.1 | 9.2.3.2 | 9.2.3.3 | 9.2.3.4 | 9.2.3.5 | 9.2.3.6 | 9.2.3.7 | 9.2.3.8 | 9.2.3.9 |
| 9.2.4.1 | 9.2.4.2 | 9.2.4.3 | 9.2.4.4 | 9.2.4.5 | 9.2.4.6 | 9.2.4.7 | 9.2.4.8 | 9.2.4.9 | 9.2.5.1 |
| 9.2.5.2 | 9.2.5.3 | 9.2.5.4 | 9.2.5.5 | 9.2.5.6 | 9.2.5.7 | 9.2.5.8 | 9.2.5.9 | 9.2.6.1 | 9.2.6.2 |
| 9.2.6.3 | 9.2.6.4 | 9.2.6.5 | 9.2.6.6 | 9.2.6.7 | 9.2.6.8 | 9.2.6.9 | 9.2.7.1 | 9.2.7.2 | 9.2.7.3 |
| 9.2.7.4 | 9.2.7.5 | 9.2.7.6 | 9.2.7.7 | 9.2.7.8 | 9.2.7.9 | 9.2.8.1 | 9.2.8.2 | 9.2.8.3 | 9.2.8.4 |
| 9.2.8.5 | 9.2.8.6 | 9.2.8.7 | 9.2.8.8 | 9.2.8.9 | 9.2.9.1 | 9.2.9.2 | 9.2.9.3 | 9.2.9.4 | 9.2.9.5 |
| 9.2.9.6 | 9.2.9.7 | 9.2.9.8 | 9.2.9.9 | 9.3.1.1 | 9.3.1.2 | 9.3.1.3 | 9.3.1.4 | 9.3.1.5 | 9.3.1.6 |
| 9.3.1.7 | 9.3.1.8 | 9.3.1.9 | 9.3.2.1 | 9.3.2.2 | 9.3.2.3 | 9.3.2.4 | 9.3.2.5 | 9.3.2.6 | 9.3.2.7 |
| 9.3.2.8 | 9.3.2.9 | 9.3.3.1 | 9.3.3.2 | 9.3.3.3 | 9.3.3.4 | 9.3.3.5 | 9.3.3.6 | 9.3.3.7 | 9.3.3.8 |
| 9.3.3.9 | 9.3.4.1 | 9.3.4.2 | 9.3.4.3 | 9.3.4.4 | 9.3.4.5 | 9.3.4.6 | 9.3.4.7 | 9.3.4.8 | 9.3.4.9 |
| 9.3.5.1 | 9.3.5.2 | 9.3.5.3 | 9.3.5.4 | 9.3.5.5 | 9.3.5.6 | 9.3.5.7 | 9.3.5.8 | 9.3.5.9 | 9.3.6.1 |
| 9.3.6.2 | 9.3.6.3 | 9.3.6.4 | 9.3.6.5 | 9.3.6.6 | 9.3.6.7 | 9.3.6.8 | 9.3.6.9 | 9.3.7.1 | 9.3.7.2 |
| 9.3.7.3 | 9.3.7.4 | 9.3.7.5 | 9.3.7.6 | 9.3.7.7 | 9.3.7.8 | 9.3.7.9 | 9.3.8.1 | 9.3.8.2 | 9.3.8.3 |
| 9.3.8.4 | 9.3.8.5 | 9.3.8.6 | 9.3.8.7 | 9.3.8.8 | 9.3.8.9 | 9.3.9.1 | 9.3.9.2 | 9.3.9.3 | 9.3.9.4 |
| 9.3.9.5 | 9.3.9.6 | 9.3.9.7 | 9.3.9.8 | 9.3.9.9 | 9.4.1.1 | 9.4.1.2 | 9.4.1.3 | 9.4.1.4 | 9.4.1.5 |
| 9.4.1.6 | 9.4.1.7 | 9.4.1.8 | 9.4.1.9 | 9.4.2.1 | 9.4.2.2 | 9.4.2.3 | 9.4.2.4 | 9.4.2.5 | 9.4.2.6 |
| 9.4.2.7 | 9.4.2.8 | 9.4.2.9 | 9.4.3.1 | 9.4.3.2 | 9.4.3.3 | 9.4.3.4 | 9.4.3.5 | 9.4.3.6 | 9.4.3.7 |
| 9.4.3.8 | 9.4.3.9 | 9.4.4.1 | 9.4.4.2 | 9.4.4.3 | 9.4.4.4 | 9.4.4.5 | 9.4.4.6 | 9.4.4.7 | 9.4.4.8 |
| 9.4.4.9 | 9.4.5.1 | 9.4.5.2 | 9.4.5.3 | 9.4.5.4 | 9.4.5.5 | 9.4.5.6 | 9.4.5.7 | 9.4.5.8 | 9.4.5.9 |
| 9.4.6.1 | 9.4.6.2 | 9.4.6.3 | 9.4.6.4 | 9.4.6.5 | 9.4.6.6 | 9.4.6.7 | 9.4.6.8 | 9.4.6.9 | 9.4.7.1 |
| 9.4.7.2 | 9.4.7.3 | 9.4.7.4 | 9.4.7.5 | 9.4.7.6 | 9.4.7.7 | 9.4.7.8 | 9.4.7.9 | 9.4.8.1 | 9.4.8.2 |
| 9.4.8.3 | 9.4.8.4 | 9.4.8.5 | 9.4.8.6 | 9.4.8.7 | 9.4.8.8 | 9.4.8.9 | 9.4.9.1 | 9.4.9.2 | 9.4.9.3 |
| 9.4.9.4 | 9.4.9.5 | 9.4.9.6 | 9.4.9.7 | 9.4.9.8 | 9.4.9.9 | 9.5.1.1 | 9.5.1.2 | 9.5.1.3 | 9.5.1.4 |
| 9.5.1.5 | 9.5.1.6 | 9.5.1.7 | 9.5.1.8 | 9.5.1.9 | 9.5.2.1 | 9.5.2.2 | 9.5.2.3 | 9.5.2.4 | 9.5.2.5 |
| 9.5.2.6 | 9.5.2.7 | 9.5.2.8 | 9.5.2.9 | 9.5.3.1 | 9.5.3.2 | 9.5.3.3 | 9.5.3.4 | 9.5.3.5 | 9.5.3.6 |
| 9.5.3.7 | 9.5.3.8 | 9.5.3.9 | 9.5.4.1 | 9.5.4.2 | 9.5.4.3 | 9.5.4.4 | 9.5.4.5 | 9.5.4.6 | 9.5.4.7 |
| 9.5.4.8 | 9.5.4.9 | 9.5.5.1 | 9.5.5.2 | 9.5.5.3 | 9.5.5.4 | 9.5.5.5 | 9.5.5.6 | 9.5.5.7 | 9.5.5.8 |
| 9.5.5.9 | 9.5.6.1 | 9.5.6.2 | 9.5.6.3 | 9.5.6.4 | 9.5.6.5 | 9.5.6.6 | 9.5.6.7 | 9.5.6.8 | 9.5.6.9 |
| 9.5.7.1 | 9.5.7.2 | 9.5.7.3 | 9.5.7.4 | 9.5.7.5 | 9.5.7.6 | 9.5.7.7 | 9.5.7.8 | 9.5.7.9 | 9.5.8.1 |
| 9.5.8.2 | 9.5.8.3 | 9.5.8.4 | 9.5.8.5 | 9.5.8.6 | 9.5.8.7 | 9.5.8.8 | 9.5.8.9 | 9.5.9.1 | 9.5.9.2 |
| 9.5.9.3 | 9.5.9.4 | 9.5.9.5 | 9.5.9.6 | 9.5.9.7 | 9.5.9.8 | 9.5.9.9 | 9.6.1.1 | 9.6.1.2 | 9.6.1.3 |
| 9.6.1.4 | 9.6.1.5 | 9.6.1.6 | 9.6.1.7 | 9.6.1.8 | 9.6.1.9 | 9.6.2.1 | 9.6.2.2 | 9.6.2.3 | 9.6.2.4 |
| 9.6.2.5 | 9.6.2.6 | 9.6.2.7 | 9.6.2.8 | 9.6.2.9 | 9.6.3.1 | 9.6.3.2 | 9.6.3.3 | 9.6.3.4 | 9.6.3.5 |
| 9.6.3.6 | 9.6.3.7 | 9.6.3.8 | 9.6.3.9 | 9.6.4.1 | 9.6.4.2 | 9.6.4.3 | 9.6.4.4 | 9.6.4.5 | 9.6.4.6 |
| 9.6.4.7 | 9.6.4.8 | 9.6.4.9 | 9.6.5.1 | 9.6.5.2 | 9.6.5.3 | 9.6.5.4 | 9.6.5.5 | 9.6.5.6 | 9.6.5.7 |
| 9.6.5.8 | 9.6.5.9 | 9.6.6.1 | 9.6.6.2 | 9.6.6.3 | 9.6.6.4 | 9.6.6.5 | 9.6.6.6 | 9.6.6.7 | 9.6.6.8 |
| 9.6.6.9 | 9.6.7.1 | 9.6.7.2 | 9.6.7.3 | 9.6.7.4 | 9.6.7.5 | 9.6.7.6 | 9.6.7.7 | 9.6.7.8 | 9.6.7.9 |
| 9.6.8.1 | 9.6.8.2 | 9.6.8.3 | 9.6.8.4 | 9.6.8.5 | 9.6.8.6 | 9.6.8.7 | 9.6.8.8 | 9.6.8.9 | 9.6.9.1 |
| 9.6.9.2 | 9.6.9.3 | 9.6.9.4 | 9.6.9.5 | 9.6.9.6 | 9.6.9.7 | 9.6.9.8 | 9.6.9.9 | 9.7.1.1 | 9.7.1.2 |

TABLE 1-continued

| | | | | | | | | | |
|---|---|---|---|---|---|---|---|---|---|
| 9.7.1.3 | 9.7.1.4 | 9.7.1.5 | 9.7.1.6 | 9.7.1.7 | 9.7.1.8 | 9.7.1.9 | 9.7.2.1 | 9.7.2.2 | 9.7.2.3 |
| 9.7.2.4 | 9.7.2.5 | 9.7.2.6 | 9.7.2.7 | 9.7.2.8 | 9.7.2.9 | 9.7.3.1 | 9.7.3.2 | 9.7.3.3 | 9.7.3.4 |
| 9.7.3.5 | 9.7.3.6 | 9.7.3.7 | 9.7.3.8 | 9.7.3.9 | 9.7.4.1 | 9.7.4.2 | 9.7.4.3 | 9.7.4.4 | 9.7.4.5 |
| 9.7.4.6 | 9.7.4.7 | 9.7.4.8 | 9.7.4.9 | 9.7.5.1 | 9.7.5.2 | 9.7.5.3 | 9.7.5.4 | 9.7.5.5 | 9.7.5.6 |
| 9.7.5.7 | 9.7.5.8 | 9.7.5.9 | 9.7.6.1 | 9.7.6.2 | 9.7.6.3 | 9.7.6.4 | 9.7.6.5 | 9.7.6.6 | 9.7.6.7 |
| 9.7.6.8 | 9.7.6.9 | 9.7.7.1 | 9.7.7.2 | 9.7.7.3 | 9.7.7.4 | 9.7.7.5 | 9.7.7.6 | 9.7.7.7 | 9.7.7.8 |
| 9.7.7.9 | 9.7.8.1 | 9.7.8.2 | 9.7.8.3 | 9.7.8.4 | 9.7.8.5 | 9.7.8.6 | 9.7.8.7 | 9.7.8.8 | 9.7.8.9 |
| 9.7.9.1 | 9.7.9.2 | 9.7.9.3 | 9.7.9.4 | 9.7.9.5 | 9.7.9.6 | 9.7.9.7 | 9.7.9.8 | 9.7.9.9 | 9.8.1.1 |
| 9.8.1.2 | 9.8.1.3 | 9.8.1.4 | 9.8.1.5 | 9.8.1.6 | 9.8.1.7 | 9.8.1.8 | 9.8.1.9 | 9.8.2.1 | 9.8.2.2 |
| 9.8.2.3 | 9.8.2.4 | 9.8.2.5 | 9.8.2.6 | 9.8.2.7 | 9.8.2.8 | 9.8.2.9 | 9.8.3.1 | 9.8.3.2 | 9.8.3.3 |
| 9.8.3.4 | 9.8.3.5 | 9.8.3.6 | 9.8.3.7 | 9.8.3.8 | 9.8.3.9 | 9.8.4.1 | 9.8.4.2 | 9.8.4.3 | 9.8.4.4 |
| 9.8.4.5 | 9.8.4.6 | 9.8.4.7 | 9.8.4.8 | 9.8.4.9 | 9.8.5.1 | 9.8.5.2 | 9.8.5.3 | 9.8.5.4 | 9.8.5.5 |
| 9.8.5.6 | 9.8.5.7 | 9.8.5.8 | 9.8.5.9 | 9.8.6.1 | 9.8.6.2 | 9.8.6.3 | 9.8.6.4 | 9.8.6.5 | 9.8.6.6 |
| 9.8.6.7 | 9.8.6.8 | 9.8.6.9 | 9.8.7.1 | 9.8.7.2 | 9.8.7.3 | 9.8.7.4 | 9.8.7.5 | 9.8.7.6 | 9.8.7.7 |
| 9.8.7.8 | 9.8.7.9 | 9.8.8.1 | 9.8.8.2 | 9.8.8.3 | 9.8.8.4 | 9.8.8.5 | 9.8.8.6 | 9.8.8.7 | 9.8.8.8 |
| 9.8.8.9 | 9.8.9.1 | 9.8.9.2 | 9.8.9.3 | 9.8.9.4 | 9.8.9.5 | 9.8.9.6 | 9.8.9.7 | 9.8.9.8 | 9.8.9.9 |
| 9.9.1.1 | 9.9.1.2 | 9.9.1.3 | 9.9.1.4 | 9.9.1.5 | 9.9.1.6 | 9.9.1.7 | 9.9.1.8 | 9.9.1.9 | 9.9.2.1 |
| 9.9.2.2 | 9.9.2.3 | 9.9.2.4 | 9.9.2.5 | 9.9.2.6 | 9.9.2.7 | 9.9.2.8 | 9.9.2.9 | 9.9.3.1 | 9.9.3.2 |
| 9.9.3.3 | 9.9.3.4 | 9.9.3.5 | 9.9.3.6 | 9.9.3.7 | 9.9.3.8 | 9.9.3.9 | 9.9.4.1 | 9.9.4.2 | 9.9.4.3 |
| 9.9.4.4 | 9.9.4.5 | 9.9.4.6 | 9.9.4.7 | 9.9.4.8 | 9.9.4.9 | 9.9.5.1 | 9.9.5.2 | 9.9.5.3 | 9.9.5.4 |
| 9.9.5.5 | 9.9.5.6 | 9.9.5.7 | 9.9.5.8 | 9.9.5.9 | 9.9.6.1 | 9.9.6.2 | 9.9.6.3 | 9.9.6.4 | 9.9.6.5 |
| 9.9.6.6 | 9.9.6.7 | 9.9.6.8 | 9.9.6.9 | 9.9.7.1 | 9.9.7.2 | 9.9.7.3 | 9.9.7.4 | 9.9.7.5 | 9.9.7.6 |
| 9.9.7.7 | 9.9.7.8 | 9.9.7.9 | 9.9.8.1 | 9.9.8.2 | 9.9.8.3 | 9.9.8.4 | 9.9.8.5 | 9.9.8.6 | 9.9.8.7 |
| 9.9.8.8 | 9.9.8.9 | 9.9.9.1 | 9.9.9.2 | 9.9.9.3 | 9.9.9.4 | 9.9.9.5 | 9.9.9.6 | 9.9.9.7 | 9.9.9.8 |
| 9.9.9.9 | | | | | | | | | |

Another group of preferred compounds are named in Table 2 and designated by numbers assigned to the variables of formula I using the following convention: $M^1.Y/Y'.V/Z/W$. The compounds are shown without depiction of stereochemistry since the compounds are biologically active as the diastereomeric mixture or as a single stereoisomer. $M^1$ is a variable that represents compounds of the formula M—H which have a specific hydroxyl group that is phosphorylated with a group $P(O)[Y$—$CH(V)CH(Z)CH(W)$—$Y']$ to make compounds of formula I.

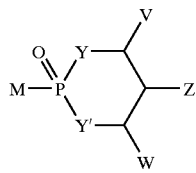

The structures for variable $M^1$ are the same as described above.

VI. VARIABLE Y/Y'

1) Y=Y'=oxygen
2) Y=NH; Y'=oxygen
3) Y=oxygen; Y'=NH
4) Y=NH; Y'=NH
5) Y=N—CH3; Y'=oxygen
6) Y=oxygen; Y'=NCH3
7) Y=N—CH2CH3; Y'=oxygen
8) Y=N-phenyl; Y'=oxygen
9) Y=Ni-propyl; Y'=oxygen Variable V/Z/W: Group V/Z/W1

1) V=phenyl; Z=methyl; W=hydrogen
2) V=3,5-dichlorophenyl; Z=methyl; W=hydrogen
3) V=4-pyridyl; Z=methyl; W=hydrogen
4) V=phenyl; Z=methoxy; W=hydrogen
5) V=3,5-dichlorophenyl; Z=methoxy; W=hydrogen
6) V=4-pyridyl; Z=methoxy; W=hydrogen
7) V=phenyl; Z=hydrogen; W=phenyl
8) V=3,5-dichlorophenyl; Z=hydrogen; W=3,5-dichlorophenyl
9) V=4-pyridyl; Z=hydrogen; W=4-pyridyl Variable V/Z/W: Group V/Z/W2

1) V=phenyl; Z=NHAc; W=hydrogen
2) V=3,5-dichlorophenyl; Z=NHAc; W=hydrogen
3) V=4-pyridyl; Z=NHAc; W=hydrogen
4) V=phenyl; Z=hydrogen; W=methyl
5) V=3,5-dichlorophenyl; Z=hydrogen; W=methyl
6) V=4-pyridyl; Z=hydrogen; W=methyl
7) V=phenyl; Z=hydroxy; W=hydrogen
8) V=3,5-dichlorophenyl; Z=hydroxy; W=hydrogen
9) V=4-pyridyl; Z=hydroxy; W=hydrogen Variable V/Z/W: Group V/Z/W3

1) V=hydrogen; Z=CH2OH; W=hydrogen
2) V=hydrogen; Z=CH2OC(O)CH3; W=hydrogen
3) V=hydrogen; Z=CH2OC(O)OCH3; W=hydrogen
4) V=methyl; Z=CH2OH; W=hydrogen
5) V=methyl; Z=CH2OC(O)CH3; W=hydrogen
6) V=methyl; Z=CH2OC(O)OCH3; W=hydrogen
7) Z=hydrogen; V and W=—CH2-CH(OH)CH2-
8) Z=hydrogen; V and W=—CH2-CH(OAc)CH2-
9) Z=hydrogen; V and W=—CH2-CH(OCO2CH2CH3)CH2-

Preferred compounds are compounds listed in Table 2 using groups $M^1$1 and V/Z/W1. For example, compound 1.1.3 represents structure 1 of group M1, i.e. etoposide; structure 1 of the variable Y/Y', i.e. both Y and Y'=oxygen; structure 3 of group V/Z/W1, i.e. V=4-pyridyl, Z=methyl and W=hydrogen. The compound 1.1.3. therefore is etoposide with the P(O)(O—CH(4-pyridyl)CH(CH3)CH2O) attached to the 4'phenolic hydroxyl.

Preferred compounds are also compounds listed in Table 2 using groups $M^1$1 and V/Z/W2.

Preferred compounds are also compounds listed in Table 2 using groups $M^1$1 and V/Z/W3.

Preferred compounds are also compounds listed in Table 2 using groups $M^1$2 and V/Z/W 1.

Preferred compounds are also compounds listed in Table 2 using groups $M^1 2$ and V/Z/W 2.

Preferred compounds are also compounds listed in Table 2 using groups $M^1 2$ and V/Z/W 3.

Preferred compounds are also compounds listed in Table 2 using groups $M^1 4$ and V/Z/W 2.

Preferred compounds are also compounds listed in Table 2 using groups $M^1 4$ and V/Z/W 3.

TABLE 2

| | | | | | | | | | | | |
|---|---|---|---|---|---|---|---|---|---|---|---|
| 1.1.1 | 1.1.2 | 1.1.3 | 1.1.4 | 1.1.5 | 1.1.6 | 1.1.7 | 1.1.8 | 1.1.9 | 1.2.1 | 1.2.2 | 1.2.3 |
| 1.2.4 | 1.2.5 | 1.2.6 | 1.2.7 | 1.2.8 | 1.2.9 | 1.3.1 | 1.3.2 | 1.3.3 | 1.3.4 | 1.3.5 | 1.3.6 |
| 1.3.7 | 1.3.8 | 1.3.9 | 1.4.1 | 1.4.2 | 1.4.3 | 1.4.4 | 1.4.5 | 1.4.6 | 1.4.7 | 1.4.8 | 1.4.9 |
| 1.5.1 | 1.5.2 | 1.5.3 | 1.5.4 | 1.5.5 | 1.5.6 | 1.5.7 | 1.5.8 | 1.5.9 | 1.6.1 | 1.6.2 | 1.6.3 |
| 1.6.4 | 1.6.5 | 1.6.6 | 1.6.7 | 1.6.8 | 1.6.9 | 1.7.1 | 1.7.2 | 1.7.3 | 1.7.4 | 1.7.5 | 1.7.6 |
| 1.7.7 | 1.7.8 | 1.7.9 | 1.8.1 | 1.8.2 | 1.8.3 | 1.8.4 | 1.8.5 | 1.8.6 | 1.8.7 | 1.8.8 | 1.8.9 |
| 1.9.1 | 1.9.2 | 1.9.3 | 1.9.4 | 1.9.5 | 1.9.6 | 1.9.7 | 1.9.8 | 1.9.9 | 2.1.1 | 2.1.2 | 2.1.3 |
| 2.1.4 | 2.1.5 | 2.1.6 | 2.1.7 | 2.1.8 | 2.1.9 | 2.2.1 | 2.2.2 | 2.2.3 | 2.2.4 | 2.2.5 | 2.2.6 |
| 2.2.7 | 2.2.8 | 2.2.9 | 2.3.1 | 2.3.2 | 2.3.3 | 2.3.4 | 2.3.5 | 2.3.6 | 2.3.7 | 2.3.8 | 2.3.9 |
| 2.4.1 | 2.4.2 | 2.4.3 | 2.4.4 | 2.4.5 | 2.4.6 | 2.4.7 | 2.4.8 | 2.4.9 | 2.5.1 | 2.5.2 | 2.5.3 |
| 2.5.4 | 2.5.5 | 2.5.6 | 2.5.7 | 2.5.8 | 2.5.9 | 2.6.1 | 2.6.2 | 2.6.3 | 2.6.4 | 2.6.5 | 2.6.6 |
| 2.6.7 | 2.6.8 | 2.6.9 | 2.7.1 | 2.7.2 | 2.7.3 | 2.7.4 | 2.7.5 | 2.7.6 | 2.7.7 | 2.7.8 | 2.7.9 |
| 2.8.1 | 2.8.2 | 2.8.3 | 2.8.4 | 2.8.5 | 2.8.6 | 2.8.7 | 2.8.8 | 2.8.9 | 2.9.1 | 2.9.2 | 2.9.3 |
| 2.9.4 | 2.9.5 | 2.9.6 | 2.9.7 | 2.9.8 | 2.9.9 | 3.1.1 | 3.1.2 | 3.1.3 | 3.1.4 | 3.1.5 | 3.1.6 |
| 3.1.7 | 3.1.8 | 3.1.9 | 3.2.1 | 3.2.2 | 3.2.3 | 3.2.4 | 3.2.5 | 3.2.6 | 3.2.7 | 3.2.8 | 3.2.9 |
| 3.3.1 | 3.3.2 | 3.3.3 | 3.3.4 | 3.3.5 | 3.3.6 | 3.3.7 | 3.3.8 | 3.3.9 | 3.4.1 | 3.4.2 | 3.4.3 |
| 3.4.4 | 3.4.5 | 3.4.6 | 3.4.7 | 3.4.8 | 3.4.9 | 3.5.1 | 3.5.2 | 3.5.3 | 3.5.4 | 3.5.5 | 3.5.6 |
| 3.5.7 | 3.5.8 | 3.5.9 | 3.6.1 | 3.6.2 | 3.6.3 | 3.6.4 | 3.6.5 | 3.6.6 | 3.6.7 | 3.6.8 | 3.6.9 |
| 3.7.1 | 3.7.2 | 3.7.3 | 3.7.4 | 3.7.5 | 3.7.6 | 3.7.7 | 3.7.8 | 3.7.9 | 3.8.1 | 3.8.2 | 3.8.3 |
| 3.8.4 | 3.8.5 | 3.8.6 | 3.8.7 | 3.8.8 | 3.8.9 | 3.9.1 | 3.9.2 | 3.9.3 | 3.9.4 | 3.9.5 | 3.9.6 |
| 3.9.7 | 3.9.8 | 3.9.9 | 4.1.1 | 4.1.2 | 4.1.3 | 4.1.4 | 4.1.5 | 4.1.6 | 4.1.7 | 4.1.8 | 4.1.9 |
| 4.2.1 | 4.2.2 | 4.2.3 | 4.2.4 | 4.2.5 | 4.2.6 | 4.2.7 | 4.2.8 | 4.2.9 | 4.3.1 | 4.3.2 | 4.3.3 |
| 4.3.4 | 4.3.5 | 4.3.6 | 4.3.7 | 4.3.8 | 4.3.9 | 4.4.1 | 4.4.2 | 4.4.3 | 4.4.4 | 4.4.5 | 4.4.6 |
| 4.4.7 | 4.4.8 | 4.4.9 | 4.5.1 | 4.5.2 | 4.5.3 | 4.5.4 | 4.5.5 | 4.5.6 | 4.5.7 | 4.5.8 | 4.5.9 |
| 4.6.1 | 4.6.2 | 4.6.3 | 4.6.4 | 4.6.5 | 4.6.6 | 4.6.7 | 4.6.8 | 4.6.9 | 4.7.1 | 4.7.2 | 4.7.3 |
| 4.7.4 | 4.7.5 | 4.7.6 | 4.7.7 | 4.7.8 | 4.7.9 | 4.8.1 | 4.8.2 | 4.8.3 | 4.8.4 | 4.8.5 | 4.8.6 |
| 4.8.7 | 4.8.8 | 4.8.9 | 4.9.1 | 4.9.2 | 4.9.3 | 4.9.4 | 4.9.5 | 4.9.6 | 4.9.7 | 4.9.8 | 4.9.9 |
| 5.1.1 | 5.1.2 | 5.1.3 | 5.1.4 | 5.1.5 | 5.1.6 | 5.1.7 | 5.1.8 | 5.1.9 | 5.2.1 | 5.2.2 | 5.2.3 |
| 5.2.4 | 5.2.5 | 5.2.6 | 5.2.7 | 5.2.8 | 5.2.9 | 5.3.1 | 5.3.2 | 5.3.3 | 5.3.4 | 5.3.5 | 5.3.6 |
| 5.3.7 | 5.3.8 | 5.3.9 | 5.4.1 | 5.4.2 | 5.4.3 | 5.4.4 | 5.4.5 | 5.4.6 | 5.4.7 | 5.4.8 | 5.4.9 |
| 5.5.1 | 5.5.2 | 5.5.3 | 5.5.4 | 5.5.5 | 5.5.6 | 5.5.7 | 5.5.8 | 5.5.9 | 5.6.1 | 5.6.2 | 5.6.3 |
| 5.6.4 | 5.6.5 | 5.6.6 | 5.6.7 | 5.6.8 | 5.6.9 | 5.7.1 | 5.7.2 | 5.7.3 | 5.7.4 | 5.7.5 | 5.7.6 |
| 5.7.7 | 5.7.8 | 5.7.9 | 5.8.1 | 5.8.2 | 5.8.3 | 5.8.4 | 5.8.5 | 5.8.6 | 5.8.7 | 5.8.8 | 5.8.9 |
| 5.9.1 | 5.9.2 | 5.9.3 | 5.9.4 | 5.9.5 | 5.9.6 | 5.9.7 | 5.9.8 | 5.9.9 | 6.1.1 | 6.1.2 | 6.1.3 |
| 6.1.4 | 6.1.5 | 6.1.6 | 6.1.7 | 6.1.8 | 6.1.9 | 6.2.1 | 6.2.2 | 6.2.3 | 6.2.4 | 6.2.5 | 6.2.6 |
| 6.2.7 | 6.2.8 | 6.2.9 | 6.3.1 | 6.3.2 | 6.3.3 | 6.3.4 | 6.3.5 | 6.3.6 | 6.3.7 | 6.3.8 | 6.3.9 |
| 6.4.1 | 6.4.2 | 6.4.3 | 6.4.4 | 6.4.5 | 6.4.6 | 6.4.7 | 6.4.8 | 6.4.9 | 6.5.1 | 6.5.2 | 6.5.3 |
| 6.5.4 | 6.5.5 | 6.5.6 | 6.5.7 | 6.5.8 | 6.5.9 | 6.6.1 | 6.6.2 | 6.6.3 | 6.6.4 | 6.6.5 | 6.6.6 |
| 6.6.7 | 6.6.8 | 6.6.9 | 6.7.1 | 6.7.2 | 6.7.3 | 6.7.4 | 6.7.5 | 6.7.6 | 6.7.7 | 6.7.8 | 6.7.9 |
| 6.8.1 | 6.8.2 | 6.8.3 | 6.8.4 | 6.8.5 | 6.8.6 | 6.8.7 | 6.8.8 | 6.8.9 | 6.9.1 | 6.9.2 | 6.9.3 |
| 6.9.4 | 6.9.5 | 6.9.6 | 6.9.7 | 6.9.8 | 6.9.9 | 7.1.1 | 7.1.2 | 7.1.3 | 7.1.4 | 7.1.5 | 7.1.6 |
| 7.1.7 | 7.1.8 | 7.1.9 | 7.2.1 | 7.2.2 | 7.2.3 | 7.2.4 | 7.2.5 | 7.2.6 | 7.2.7 | 7.2.8 | 7.2.9 |
| 7.3.1 | 7.3.2 | 7.3.3 | 7.3.4 | 7.3.5 | 7.3.6 | 7.3.7 | 7.3.8 | 7.3.9 | 7.4.1 | 7.4.2 | 7.4.3 |
| 7.4.4 | 7.4.5 | 7.4.6 | 7.4.7 | 7.4.8 | 7.4.9 | 7.5.1 | 7.5.2 | 7.5.3 | 7.5.4 | 7.5.5 | 7.5.6 |
| 7.5.7 | 7.5.8 | 7.5.9 | 7.6.1 | 7.6.2 | 7.6.3 | 7.6.4 | 7.6.5 | 7.6.6 | 7.6.7 | 7.6.8 | 7.6.9 |
| 7.7.1 | 7.7.2 | 7.7.3 | 7.7.4 | 7.7.5 | 7.7.6 | 7.7.7 | 7.7.8 | 7.7.9 | 7.8.1 | 7.8.2 | 7.8.3 |
| 7.8.4 | 7.8.5 | 7.8.6 | 7.8.7 | 7.8.8 | 7.8.9 | 7.9.1 | 7.9.2 | 7.9.3 | 7.9.4 | 7.9.5 | 7.9.6 |
| 7.9.7 | 7.9.8 | 7.9.9 | 8.1.1 | 8.1.2 | 8.1.3 | 8.1.4 | 8.1.5 | 8.1.6 | 8.1.7 | 8.1.8 | 8.1.9 |
| 8.2.1 | 8.2.2 | 8.2.3 | 8.2.4 | 8.2.5 | 8.2.6 | 8.2.7 | 8.2.8 | 8.2.9 | 8.3.1 | 8.3.2 | 8.3.3 |
| 8.3.4 | 8.3.5 | 8.3.6 | 8.3.7 | 8.3.8 | 8.3.9 | 8.4.1 | 8.4.2 | 8.4.3 | 8.4.4 | 8.4.5 | 8.4.6 |
| 8.4.7 | 8.4.8 | 8.4.9 | 8.5.1 | 8.5.2 | 8.5.3 | 8.5.4 | 8.5.5 | 8.5.6 | 8.5.7 | 8.5.8 | 8.5.9 |
| 8.6.1 | 8.6.2 | 8.6.3 | 8.6.4 | 8.6.5 | 8.6.6 | 8.6.7 | 8.6.8 | 8.6.9 | 8.7.1 | 8.7.2 | 8.7.3 |
| 8.7.4 | 8.7.5 | 8.7.6 | 8.7.7 | 8.7.8 | 8.7.9 | 8.8.1 | 8.8.2 | 8.8.3 | 8.8.4 | 8.8.5 | 8.8.6 |
| 8.8.7 | 8.8.8 | 8.8.9 | 8.9.1 | 8.9.2 | 8.9.3 | 8.9.4 | 8.9.5 | 8.9.6 | 8.9.7 | 8.9.8 | 8.9.9 |
| 9.1.1 | 9.1.2 | 9.1.3 | 9.1.4 | 9.1.5 | 9.1.6 | 9.1.7 | 9.1.8 | 9.1.9 | 9.2.1 | 9.2.2 | 9.2.3 |
| 9.2.4 | 9.2.5 | 9.2.6 | 9.2.7 | 9.2.8 | 9.2.9 | 9.3.1 | 9.3.2 | 9.3.3 | 9.3.4 | 9.3.5 | 9.3.6 |
| 9.3.7 | 9.3.8 | 9.3.9 | 9.4.1 | 9.4.2 | 9.4.3 | 9.4.4 | 9.4.5 | 9.4.6 | 9.4.7 | 9.4.8 | 9.4.9 |
| 9.5.1 | 9.5.2 | 9.5.3 | 9.5.4 | 9.5.5 | 9.5.6 | 9.5.7 | 9.5.8 | 9.5.9 | 9.6.1 | 9.6.2 | 9.6.3 |
| 9.6.4 | 9.6.5 | 9.6.6 | 9.6.7 | 9.6.8 | 9.6.9 | 9.7.1 | 9.7.2 | 9.7.3 | 9.7.4 | 9.7.5 | 9.7.6 |
| 9.7.7 | 9.7.8 | 9.7.9 | 9.8.1 | 9.8.2 | 9.8.3 | 9.8.4 | 9.8.5 | 9.8.6 | 9.8.7 | 9.8.8 | 9.8.9 |
| 9.9.1 | 9.9.2 | 9.9.3 | 9.9.4 | 9.9.5 | 9.9.6 | 9.9.7 | 9.9.8 | 9.9.9 | | | |

Preferred compounds are also compounds listed in Table 2 using groups $M^1 3$ and V/Z/W 1.

Preferred compounds are also compounds listed in Table 2 using groups $M^1 3$ and V/Z/W 2.

Preferred compounds are also compounds listed in Table 2 using groups $M^1 3$ and V/Z/W 3.

Preferred compounds are also compounds listed in Table 2 using groups $M^1 4$ and V/Z/W 1.

For best mode purposes, it is believed that the best prodrugs are those where V is phenyl substituted with 1–3 halogens or 4-pyridyl, and Z, W and W' are H, and both Y groups are oxygen. More preferred are such prodrugs in which V is selected from the group of 3-chlorophenyl, 3-bromophenyl, 2-bromphenyl, phenyl, and 4-pyridyl. When M is PMEA, at this point in time, the best prodrug is where V is 3-chlorophenyl, and Z, W and W' are H, and both Y groups are oxygen.

Synthesis of Compounds of Formula I

Synthesis of the compounds encompassed by the present invention includes: I). synthesis of prodrugs; II). and synthesis of substituted-1,3-diols; III.) synthesis of substituted-1,3-amino alcohols and substituted-1,3-diamines.

I) Synthesis of Prodrugs

The following procedures on the preparation of prodrugs illustrate the general procedures used to prepare the prodrugs of the invention which apply to all hydroxy, thiol, and amine-containing drugs. Prodrugs can be introduced at different stages of synthesis of a drug. Most often they are made at a later stage, because of the general sensitivity of these groups to various reaction conditions. Optically pure prodrugs containing a single isomer at phosphorus center can be made either by separation of the diastereomers by a combination of column chromatography and/or crystallization, or by enantioselective synthesis of chiral activated phosph(oramid)ate intermediates. All the procedures described herein, where Y and Y' are oxygen, are also applicable for the preparation of the prodrugs when Y and/or Y' are —NR$^6$ by appropriate substitution or protection of nitrogen.

The preparation of prodrugs is further organized into 1) synthesis via activated P(V) intermediates:, 2) synthesis via activated P(III) intermediates, and 3) miscellaneous methods.

I.1 Synthesis via Activated P(V) Intermediate

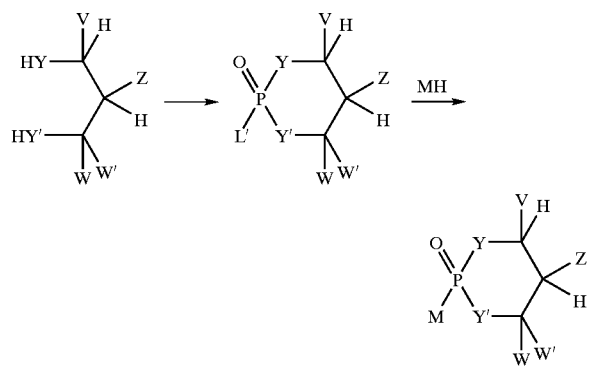

I.1.a Synthesis of Activated P(V) Intermediates

In general, synthesis of phosph(oramid)ate esters is achieved by coupling the amine, thiol, or alcohol of MH, with the corresponding activated phosphate precursor for example, Chlorophosphate (L'=chloro) addition onto hydroxy or amino or thiol-containing drug molecules is one preferred method for preparation of prodrugs. The activated precursor can be prepared by several well known methods. Chlorophosphates useful for synthesis of the prodrugs are prepared from the substituted-1,3-propanediols (Wissner, et al., *J. Med Chem.*, 1992, 35, 1650). Chlorophosphates are made by oxidation of the corresponding chlorophospholanes (Anderson, et al., *J. Org. Chem.*, 1984, 49, 1304) which are obtained by reaction of the substituted diol with phosphorus trichloride. Alternatively, the chlorophosphate agent is made by treating substituted-1,3-diols with phosphorusoxychloride (Patois, et al., *J. Chem. Soc. Perkin Trans. I*, 1990, 1577). Chlorophosphate species may also be generated in situ from corresponding cyclic phosphites by treatment with carbon tetrachloride in the presence of a base (Silverburg, et al., *Tetrahedron lett.*, 1996, 37, 771), which in turn can be either made from chlorophospholane or phosphoramidite intermediate by treatment with a mild acid. Phosphorofluoridate intermediate prepared either from pyrophosphate or phosphoric acid may also act as precursor in preparation of cyclic prodrugs (Watanabe et al., *Tetrahedron Lett.*, 1988, 29, 5763). Similar procedures can be used where Y and/or Y' are —NR$^6$—.

Phosph(oramid)ates where L'=NRR' are also well known intermediates for the synthesis of phosphate esters. Monoalkyl or dialkylphosphoramidate (Watanabe, et al., *Chem Pharm Bull.*, 1990, 38, 562), triazolophosphoramidate (Yamakage, et al., *Tetrahedron ,*1989, 45, 5459) and pyrrolidinophosphoramidate (Nakayama, et al., *J. Am. Chem. Soc.*, 1990, 112, 6936) are some of the known intermediates used for the preparation of phosphate esters. Another effective phosphorylating procedure is a metal catalyzed addition of the cyclic chlorophosphate adduct with 2-oxazolone. This intermediate attains high selectivity in phosphorylation of primary hydroxy group in presence of secondary hydroxyl group (Nagamatsu, et al., *Tetrahedron Lett.*, 1987, 28, 2375). These agents are obtained by reaction of a chlorophosphate with the amine or alternatively by formation of the corresponding phosphoramidite followed by oxidation. Similar reactions are possible where Y and/or Y' are —NR$^6$—.

I.1.b. Synthesis of Chiral Activated Phosph(oramid)ate

Phosphorylation of an enantiomerically pure substituted diol with for example, a commercially available phosphorodichloridate R—OP(O)Cl$_2$, where RO is a leaving group, preferably aryl substituted with electron withdrawing groups, such as a nitro or a chloro, produces two diastereomeric intermediates that can be separated by a combination of column chromatography and/or crystallization. Such a method may also be utilized in preparing chiral chloro phosphonates. Chiral phosphoramidate intermediates can be obtained by utilization of optically pure amine as the chiral auxiliary. This type of intermediate are known to undergo stereospecific substitution (Nakayama, et al. *J. Am. Chem. Soc.*,1990, 112, 6936). The relative configuration of the phosphorus atom is easily determined by comparison of the $^{31}$P NMR spectra. The chemical shift of the equatorial phosphoryloxy moiety (trans-isomer) is always more upfield than the one of the axial isomer (cis-isomer) (Verkade, et al., *J. Org. Chem.*, 1977, 42, 1549).

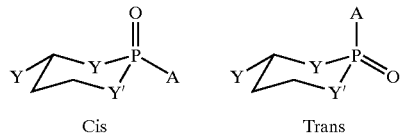

Cis          Trans

Similar methods are possible where Y and/or Y' are —NR$^6$—.

I.1.c. Synthesis of Prodrugs Using Activated Phosphates

Coupling of activated phosphates with alcohols or amines (MH) is accomplished in the presence of an organic base. For example, Chlorophosphates synthesized as described in the earlier section react with an alcohol in the presence of a base such as pyridines or N-methylimidazole. In some cases phosphorylation is enhanced by in situ generation of iodophosphate from the chlorophosphate (Stomberg, et al., *Nucleosides & Nucleotides.*, 1987, 5: 815). Phosphoroflouridate intermediates have also been used in phosphorylation reactions in the presence of a base such as CsF or n-BuLi to generate cyclic prodrugs (Watanabe et al., *Tetrahedron Lett.*, 1988, 29, 5763). Phosphoramidate intermediates are shown to couple by transition metal catalysis (Nagamatsu, et al., *Tetrahedron Lett.*, 1987, 28, 2375).

Reaction of the optically pure diastereomer of a phosphoramidate intermediate with the hydroxyl of the drug in the presence of an acid produces the optically pure phosphate prodrug by direct $S_N2(P)$ reaction (Nakayama, et al. *J. Am. Chem. Soc.,*1990, 112, 6936). Alternatively, reaction of the optically pure phosphate precursor with a fluoride source, preferably cesium fluoride or tetrabutylammonium fluoride, produces the more reactive phosphorofluoridate which reacts with the hydroxyl of the drug to give the optically pure prodrug by overall retention of configuration at the phosphorus atom (Ogilvie, et al., *J. Am. Chem. Soc.,*1977, 99, 1277). Chiral phosphonate prodrugs can be synthesized by either resolution of phosphates (Pogatnic, et al., *Tetrahedron Lett.,* 1997, 38, 3495) or by chirality induction (Taapken, et al., *Tetrahedron Lett.,* 1995, 36, 6659; *J. Org. Chem.,* 1998, 63, 8284).

Similar procedures where Y and/or Y' are —NR$^6$— are possible.

I.2 Synthesis Via Phosphite Intermediate P(III)

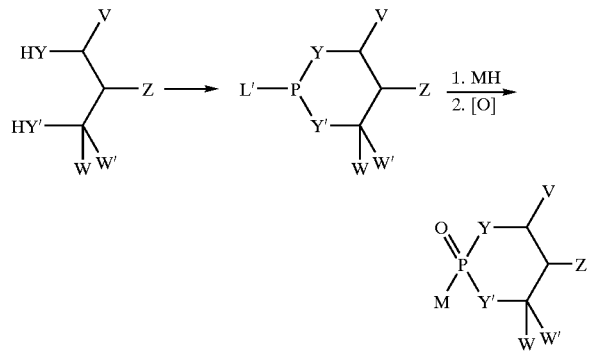

I.2.a. Synthesis of Activated P(III) Intermediates

Phosphorylation of hydroxy, thiol, and amino groups is achieved using cyclic 1',3'-propanyl esters of phosphorylating agents where the agent is at the P(III) oxidation state. One preferred phosphorylating agent is a chloro phospholane (L'=chloro). Cyclic chlorophospholanes are prepared under mild conditions by reaction of phosphorus trichloride with substituted 1,3-diols (Wissner, et al.,*J. Med. Chem.,* 1992, 35, 1650). Alternatively phosphoramidites can be used as the phosphorylating agent (Beaucage, et al., *Tetrahedron,* 1993, 49, 6123). Appropriately substituted phoshoramidites can be prepared by reacting cyclic chlorophospholanes with N,N-dialkylamine (Perich, et al.,*Aust. J. Chem.,* 1990, 43, 1623. Perich, et al., *Synthesis,* 1988, 2, 142) or by reaction of commercially available dialkylaminophosphorodichloridate with substituted propyl-1,3-diols. Similar procedures may be used where Y and/or Y' are —NR$^6$—.

I.2.b. Synthesis of Chiral Activated P(III) Intermediate

In the cases where unsymmetrical diols are used, the cyclic phosphite is expected to form a mixture of chiral isomers. When an optically active pure diol is used a chromatographically separable mixture of two stable diastereomers with the leaving group (NRR') axial and equatorial on the phosphorous atom is expected. Pure diasteromers can usually be obtained by chromatographic separation. Chiral induction may also be attained by utilizing chiral amine precursors.

I.2.c. Synthesis of Prodrugs Using Activated Phosphites

Chlorophospholanes are used to phosphorylate alcohols on drug molecules in the presence of an organic base (e.g., triethylamine, pyridine). Alternatively, the phosphite can be obtained by coupling the drug molecule with a phosphoramidate in the presence of a coupling promoter such as tetrazole or benzimidazolium triflate (Hayakawa et al., *J. Org. Chem.,* 1996, 61, 7996). Phosphite diastereomers may be isolated by column chromatography or crystallization (Wang, et al., *Tetrahedron Lett,* 1997, 38, 3797; Bentridge et al., *J. Am. Chem. Soc.,* 1989, 111, 3981). Since condensation of alcohols with chlorophospholanes or phosphoramidites is an $S_N2(P)$ reaction, the product is expected to have an inverted configuration. This allows for the stereoselective synthesis of cyclic phosphites. Stereospecific synthesis of a thermodynamically more stable phosphite is attained by equilibration (e.g., thermal equilibration) reaction, when a mixture of two phosphites are obtained starting from a chiral diol.

The resulting phosphites are subsequently oxidized to the corresponding phosphate prodrugs using an oxidant such as molecular oxygen or t-butylhydroperoxide (Meier et al., *Bioorg. Med. Chem. Lett.,* 1997, 7, 1577). Oxidation of optically pure phosphites is expected to stereoselectively provide optically active prodrugs (Mikolajczyk, et al., *J. Org. Chem.,* 1978, 43, 2132. Cullis, P. M. *J. Chem. Soc., Chem Commun.,* 1984, 1510, Verfurth, et al., *Chem. Ber.,* 1991, 129, 1627). Hence, a combination of thermodynamic equilibration of phosphite and stereoselective oxidation results in chiral prodrugs by starting from chiral diols. Chiral prodrugs may also be obtained starting from chiral drug and a P(V) or P(III) intermediate, when the drug has an imposing topology at the reaction site and has a certain facial selectivity.

I.3. Miscellaneous Methods

Prodrugs are also prepared from the free acid and substituted 1,3-diols by Mitsunobu reactions (Mitsunobu, *Synthesis,* 1981, 1; Campbell, *J. Org. Chem.,* 1992, 52: 6331), and other acid coupling reagents including, but not limited to, carbodiimides (Alexander, et al., *Collect. Czech. Chem. Commun.,* 1994, 59: 1853; Casara, et al., *Bioorg. Med. Chem. Lett.,* 1992, 2: 145; Ohashi, et al., *Tetrahedron Lett.,* 1988, 29: 1189; Hoffman, M., *Synthesis,* 1988, 62), and benzotriazolyloxytris-(dimethylamino)phosphonium salts (Campagne, et al., *Tetrahedron Lett.,* 1993, 34: 6743).

Phosphorylation of an alcohol thiol or an amine is also achieved under Mitsunobu reaction conditions using the cyclic 1',3'-propanyl ester of phosphoric acid in the presence of triphenylphosphine and diethylazodicarboxylate (Kimura et al., *Bull. Chem. Soc. Jpn.,* 1979, 52, 1191). The procedure can be extended to prepare chiral phosphates from enantiomerically pure phosphoric acids.

Prodrugs can be prepared by an alkylation reaction between the phosphonate corresponding tetrabutylammonium salts and substituted-1,3-diiodo propanes made from 1,3-diols (Farquhar, et al., *Tetrahedron Lett.,* 1995 36, 655). Furthermore, phosphate prodrugs can be made by conversion of drug molecule to the dichloridate intermediate with phosphoryl chloride in presence of triethylphosphite and quenching with substituted-1,3-propane diols (Farquhar et al., *J. Org. Chem.,* 1983, 26, 1153).

Phosphorylation can also be achieved by making the mixed anhydride of the cyclic diester of phosphoric acid and a sulfonyl chloride, preferably 8-quinolinesulfonyl chloride, and reacting the hydroxyl of the drug in the presence of a base, preferably methylimidazole (Takaku, et al., *J. Org. Chem.,* 1982, 47, 4937). In addition, starting from a chiral cyclic diester of a phosphoric acid, obtained by chiral resolution (Wynberg, et al.,*J. Org. Chem.,* 1985, 50, 4508), one can obtain optically pure phosphates.

Similar procedures may be used where Y and/or Y' are —NR$^6$—.

II.1) Synthesis of 1,3-Diols

A variety of synthetic methods are known to prepare the following types of 1,3-diols: a) 1-substituted; b)

2-substituted; and c) 1,2- or 1,3-annulated in their racemic or chiral form. Substitution of V, W, Z groups of formula I, can be introduced or modified either during synthesis of diols or after the synthesis of prodrugs.

II.1) 1-Substituted 1,3-Diols 1,3-Dihydroxy compounds can be synthesized by several well known methods in literature. Aryl Grignard additions to 1-hydroxy propan-3-al give 1-aryl-substituted propan-1,3-diols (path a). This method will enable conversion of various substituted aryl halides to 1-arylsubstituted-1,3-propane diols (Coppi, et al., *J. Org. Chem.,* 1988, 53, 911). Aryl halides can also be used to synthesize 1-substituted propanediols by Heck coupling of 1,3-diox-4-ene followed by reduction and hydrolysis (Sakamoto, et al., *Tetrahedron Lett.,* 1992, 33, 6845). Substituted 1,3-diols can be generated enanatioselective reduction of vinyl ketone and hydoboration or by kinetic resolution of allylic alcohol (path b). Variety of aromatic aldehydes can be converted to 1-substituted-1,3-diols by vinyl Grignard addition followed by hydroboration (path b). Substituted aromatic aldehydes are also utilized by lithium-t-butylacetate addition followed by ester reduction (path e) (Turner., *J. Org. Chem.,* 1990, 55 4744). In another method, commercially available cinnamyl alcohols can be converted to epoxy alcohols under catalytic asymmetric epoxidation conditions. These epoxy alcohols are reduced by Red-Al to result in enantiomerically pure 1,3-diols (path c) (Gao, et al., *J. Org. Chem.,* 1980, 53, 4081). Alternatively, enantiomerically pure 1,3-diols can be obtained by chiral borane reduction of hydroxyethyl aryl ketone derivatives (Ramachandran, et al., *Tetrahedron Lett.,* 1997, 38 761). Pyridyl, quinoline, isoquinoline propan-3-ol derivatives can be oxygenated to 1-substituted-1,3-diol by N-oxide formation followed by rearrangement in acetic anhydride conditions (path d) (Yamamoto, et al., *Tetrahedron,* 1981, 37, 1871). Aldol condensation is another well described method for synthesis of the 1,3-oxygenated functionality (Mukaiyama, *Org. React.,* 1982, 28, 203). Chiral substituted diols can also be made by enantioselective reduction of carbonyl compounds, by chiral aldol condensation or by enzyme promoted kinetic resolution.

II.2) 2-Substituted 1,3-Diols

Various 2-substituted-1,3-diols can be made from commercially available 2-(hydroxymethyl)-1,3-propane diol. Pentaerythritol can be converted to triol via decarboxylation of diacid followed by reduction (path a) (Werle, et al., *Liebigs. Ann. Chem.,* 1986, 944) or diol-monocarboxylic acid derivatives can also be obtained by decarboxylation under known conditions (Iwata, et al., *Tetrahedron lett.* 1987, 28, 3131). Nitrotriol is also known to give triol by reductive elimination (path b) (Latour, et al., *Synthesis,* 1987, 8, 742). The triol can be derivatised by mono acetylation or carbonate formation by treatment with alkanoyl chloride, or alkylchloroformate(path d) (Greene and Wuts, *Protective groups in organic synthesis,* John Wiley, New York, 1990). Aryl substitution can be affected by oxidation to aldehyde and aryl Grignard additions (path c) Aldehydes can also be converted to substituted amines by reductive amination reaction(path e).

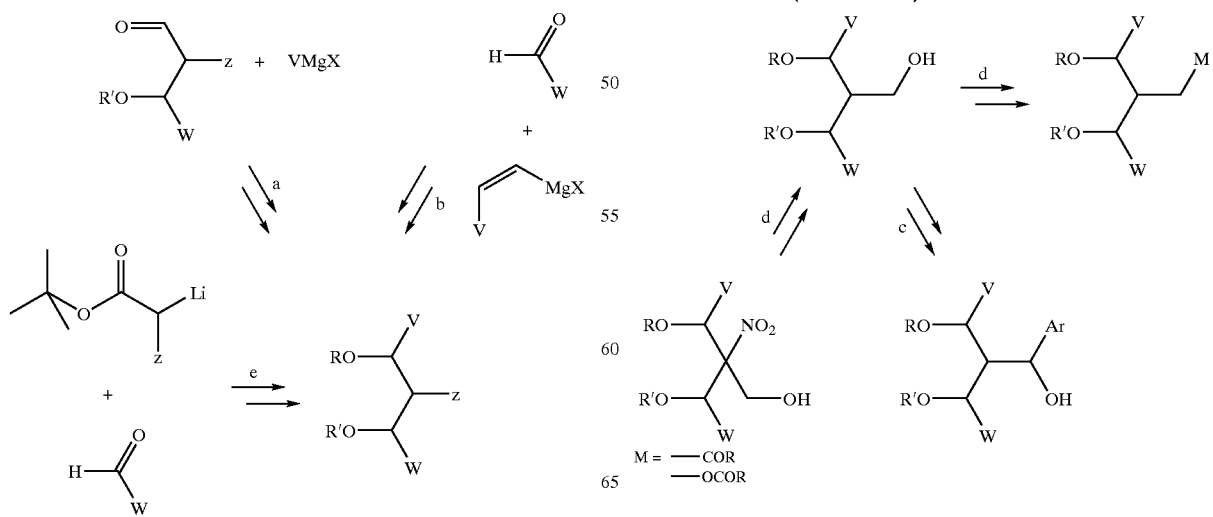

I.3.c) Cyclic-1,3-diols

Compounds of formula 1 where V—Z or V—W are fused by four carbons are made from Cyclohexane diol derivatives. Commercially available cis, cis-1,3,5-cyclohexane triol can be used as is or modified as described in case of 2-substituted propan-1,3-diols to give various analogues. These modifications can either be made before or after ester formation. Various 1,3-cyclohexane diols can be made by Diels-Alder methodology using pyrone as diene (Posner, et al., *Tetrahedron Lett.*, 1991, 32, 5295). Cyclohexyl diol derivatives are also made by nitrile oxide-olefin additions (Curran, et al., *J. Am. Chem. Soc.*, 1985, 107, 6023). Alternatively, cyclohexyl precursors are also made from commercially available quinic acid (Rao, et al., *Tetrahedron Lett.*, 1991, 32, 547.)

III. Synthesis of Substituted 1,3-Hydroxyamines and 1,3-Diamines

A large number of synthetic methods are available for the preparation of substituted 1,3-hydroxyamines and 1,3-diamines due to the ubiquitous nature of these functionalities in naturally occurring compounds. Following are some of these methods organized into: 1. synthesis of substituted 1,3-hydroxy amines; 2. synthesis of substituted 1,3-diamines and 3. Synthesis of chiral substituted 1,3-hydroxyamines and 1,3-diamines.

III.1. Synthesis of Substituted 1,3-hydroxy Amines 1,3-Diols described in the earlier section can be converted selectively to either hydroxy amines or to corresponding diamines by converting hydroxy functionality to a leaving group and treating with anhydrous ammonia or required primary or secondary amines (Corey, et al., *Tetrahedron Lett.*, 1989, 30, 5207: Gao, et al., *J. Org. Chem.*, 1988, 53, 4081). A similar transformation may also be achieved directly from alcohols in Mitsunobu type of reaction conditions (Hughes, D. L., *Org. React.*, 1992, 42).

A general synthetic procedure for 3-aryl-3-hydroxy-propan-1-amine type of prodrug moiety involves aldol type condensation of aryl esters with alkyl nitrites followed by reduction of resulting substituted benzoylacetonitrile (Shih et al., *Heterocycles*, 1986, 24, 1599). The procedure can also be adapted for formation 2-substitutedaminopropanols by using substituted alkylnitrile. In another approach, 3-aryl-3-amino-propan-1-ol type of prodrug groups are synthesized from aryl aldehydes by condensation of malonic acid in presence of ammonium acetate followed by reduction of resulting substituted β-amino acids. Both these methods enable to introduce wide variety of substitution of aryl group (Shih, et al., *Heterocycles.*, 1978, 9, 1277). In an alternate approach, β-substituted organolithium compounds of 1-amino-1-aryl ethyl dianion generated from styrene type of compounds undergo addition with carbonyl compounds to give variety of W, W' substitution by variation of the carbonyl compounds (Barluenga, et al., *J.Org. Chem.*, 1979, 44, 4798).

III.2. Synthesis of Substituted 1,3-diamines

Substituted 1,3-diamines are synthesized starting from variety of substrates. Arylglutaronitriles can be transformed to 1-substituted diamines by hydrolysis to amide and Hoffman rearrangement conditions (Bertochio, et al., *Bull. Soc. Chim. Fr*, 1962, 1809). Whereas, malononitrile substitution will enable variety of Z substitution by electrophile introduction followed by hydride reduction to corresponding diamines. In another approach, cinnamaldehydes react with hydrazines or substituted hydrazines to give corresponding pyrazolines which upon catalytic hydrogenation result in substituted 1,3-diamines (Weinhardt, et al., *J. Med. Chem.*, 1985, 28, 694). High trans-diastereoselectivity of 1,3-substitution is also attainable by aryl Grignard addition on to pyrazolines followed by reduction (Alexakis, et al., *J. Org. Chem.*, 1992, 576, 4563). 1-Aryl-1,3-diaminopropanes are also prepared by diborane reduction of 3-amino-3-arylacrylonitriles which in turn are made from nitrile substituted aromatic compounds (Dornow, et al., *Chem Ber.*, 1949, 82, 254). Reduction of 1,3-diimines obtained from corresponding 1,3-carbonyl compounds are another source of 1,3-diamine prodrug moiety which allows a wide variety of activating groups V and/or Z (Barluenga, et al., *J. Org. Chem.*, 1983, 48, 2255).

III.3. Synthesis of Chiral Substituted 1,3-hydroxyamines and 1,3-diamines

Enantiomerically pure 3-aryl-3-hydroxypropan-1-amines are synthesized by CBS enantioselective catalytic reaction of β-chloropropiophenone followed by displacement of halo group to make secondary or primary amines as required (Corey, et al., Tetrahedron Lett., 1989, 30, 5207). Chiral 3-aryl-3-amino propan-1-ol type of prodrug moiety may be obtained by 1,3-dipolar addition of chirally pure olefin and substituted nitrone of arylaldehyde followed by reduction of resulting isoxazolidine (Koizumi, et al., *J. Org. Chem.*, 1982, 47, 4005). Chiral induction in 1,3-polar additions to form substituted isoxazolidines is also attained by chiral phosphine palladium complexes resulting in enatioselective formation of amino alcohols (Hori, et al., *J. Org. Chem.*, 1999, 64, 5017). Alternatively, optically pure 1-aryl substituted amino alcohols are obtained by selective ring opening of corresponding chiral epoxy alcohols with desired amines (Canas et al., *Tetrahedron Lett.*, 1991, 32, 6931).

Several methods are known for diastereoselective synthesis of 1,3-disubstituted aminoalcohols. For example, treatment of (E)-N-cinnamyltrichloroacetamide with hypochlorus acid results in trans-dihydrooxazine which is readily hydrolysed to erythro-β-chloro-γ-hydroxy-γ-phenylpropanamine in high diastereoselectivity (Commercon et al., *Tetrahedron Lett.*, 1990, 31, 3871). Diastereoselective formation of 1,3-aminoalcohols is also achieved by reductive amination of optically pure 3-hydroxy ketones (Haddad et al., *Tetrahedron Lett.*, 1997, 38, 5981). In an alternate approach, 3-amninoketones are transformed to 1,3-disubstituted aminoalcohols in high stereoselectivity by a selective hydride reduction (Barluenga et al., *J. Org. Chem.*, 1992, 57, 1219).

All the above mentioned methods may also be applied to prepare corresponding V—Z or V—W annulated chiral aminoalcohols. Furthermore, such optically pure amino alcohols are also a source to obtain optically pure diamines by the procedures described earlier in the section.

Formulations

Dose of the prodrugs of the present invention depend on the activity of the parent drug, the disease being treated, the oral bioavailability of the prodrug, and the physical characteristics of the patient.

Compounds of the invention may be administered orally in a total daily dose of about 0.1 mg/kg/dose to about 100 mg/kg/dose, preferably from about 0.3 mg/kg/dose to about 30 mg/kg/dose. The most preferred dose range is from 0.5 to 10 mg/kg (approximately 1 to 20 nmoles/kg/dose). The use of time-release preparations to control the rate of release of the active ingredient may be preferred. The dose may be administered in as many divided doses as is convenient. When other methods are used (e.g. intravenous administration), compounds may be administered to the affected tissue at a rate from 0.3 to 300 nmol/kg/min, preferably from 3 to 100 nmoles/kg/min. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 μmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion may contain from about 0.05 to about 50 μmol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular

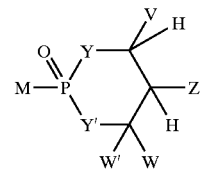

disease undergoing therapy, as is well understood by those skilled in the art.

Formula 1

EXAMPLES

The prodrug compounds of this invention, their intermediates, and their preparation can be understood further by the examples which illustrate some of the processes by which these compounds are prepared. These examples should not however be construed as specifically limiting the invention and variations of the compounds, now known or later developed, are considered to fall within the scope of the present invention as hereinafter claimed.

Compounds of formula I are prepared using procedures detailed in the following examples.

Compounds of Formula 1:

Formula 1

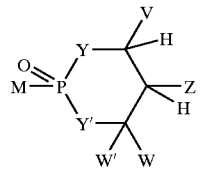

| Example # | M | V | Z | W | W' | Y | Y |
|---|---|---|---|---|---|---|---|
| 1.1 | 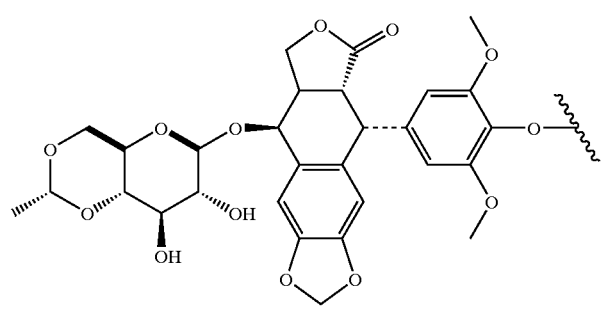 | 4-Pyridyl | H | H | H | O | O |

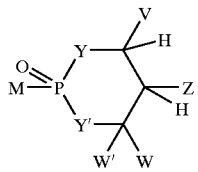

Formula 1

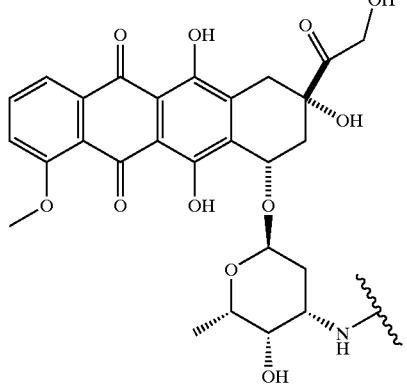

| Example # | M | V | Z | W | W' | Y | Y |
|---|---|---|---|---|---|---|---|
| 2.1 | OH | (R)-phenyl | H | H | H | O | O |

Example 1

General Procedure for Formation of Etoposide Prodrugs

To a solution of 1(4-pyridyl)-propane-1,3-diol (321 mg, 2.1 mmol) (prepared as in Example 5) in dichloromethane (20 mL) was added phosphorus trichloride at 0° C. The reaction was warmed to room temperature and allowed to stir for 3 h. Reaction mixture was concentrated, azeotroped with toluene (2×10 mL) and dried. The crude chlorophospholane was used in the next step without further purification.

To a solution of etoposide (250 mg, 0.42 mmol) in DMF (10 mL) was added diisopropylethylamine (1.09 mL, 6.3 mmol) at −40° C. To this mixture was added crude cyclic chlorophospholane (455 mg, 2.1 mmole) in 2 mL of DMF. The mixture was warmed to room temperature and stirred for 2 h. The reaction was cooled back to −40° C. and 5–6M t-butylhydroperoxide in decane (0.84 mL, 4.2 mmol) was added and left at room temperature overnight. The reaction was concentrated and crude mixture was chromatographed by eluting with 5% methanol-dichloromethane on a silica gel column to give pure product (160 mg, 48%).

1.1: 4'-O-(2-oxo-4-pyridyl-1,3,2-dioxaphosphorinan-2-yl)-etoposide Rf=0.38 in 10%MeOH-dichloromethane: mp=>210° C.; Anal. Cald. for $C_{37}H_{40}NO_{16}P+2H_2O+1CH_2Cl_2$: C, 50.34; H, 5.11; N, 1.54. Found: C, 50.00; H, 4.74; N, 1.61.

Example 2

General Procedure for the Formation of Doxorubicin Prodrugs

Step A

A mixture of 1.201 g (7.9 mmol) of (R)-1-phenyl-1,3-propanediol and 50 mL of $CH_2Cl_2$ was heated to reflux and a solution of $POCl_3$ (0.8 mL, 8.6 mmol) in 50 mL of $CH_2Cl_2$ was added dropwise. After the addition was complete, the mixture was heated to reflux for further 3 h. The reaction mixture was poured over a mixture of ice and saturated sodium bicarbonate solution. The organic phase was separated, rinsed with water and saturated sodium chloride and dried over $MgSO_4$. Evaporation of the solvent left a white semisolid, which was treated with ether. The white precipitate formed was filtered, rinsed with more ether and dried under vacuum at room temperature to get 767 mg (42%) of product as a white solid.

Step B

Reaction of doxorubicin with cyclic phosphochloridate

A mixture of doxorubicin hydrochloride (58.5 mg, 0.10 mmol), phosphorylating agent (26.7 mg, 0.12 mmol) and diisopropylethylamine (45.5 μL, 0.26 mmol) in 3.0 mL of DMF was stirred for 19 h at room temperature. Treated with additional diisopropylethylamine (60 μL, 0.34 mmol) and phosphorylating agent (31.8 mg, 0.14 mmol) and stirred for an additional 31 h. The solvent was removed under reduced pressure and the residue was chromatographed on a short silica column eluting with 5% methanol in dichloromethane. The product obtained was treated with $CH_3OH/CH_2Cl_2$ and precipitated with ether. The red solid was filtered, rinsed with ether and dried under vacuum at room temperature.

2.1: 4'-O-(2-oxo-4-(R)-phenyl-1,3,2-dioxaphosphorinan-2-yl)-doxorubicin mp=172–175° C.; Anal. Cald. for $C_{36}H_{38}NO_{14}P+(1.75)H_2O$: C, 56.07; H, 5.42; N, 1.82. Found: C, 55.70; H, 4.93; N, 1.71; Mass cald [M+Na]+:762. Found: 762; 31PNMR (202 MHz, DMSO): +6.59 (s).

Example 3

General Procedure for Formation of Camptothecin Prodrugs

To a solution of 1(4-pyridyl)-propane-1,3-diol (1 mmol) in dichloromethane (10 mL) is added phosphorus trichloride at 0° C. The reaction is warmed to room temperature and allowed to stir for 3 h. Reaction mixture is concentrated, azeotroped with toluene (2×10 mL) and dried. Crude chlorophospholane is used in next step without further purification.

To a solution of camptothecin (1 mmol) in DMF (10 mL) is added diisopropylethylamine (2 mmol) at −40° C. To this mixture is added crude cyclic chlorophospholane (1 mmole) in 2 mL of DMF. The mixture is warmed to room temperature and stirred for 2 h. The reaction is cooled back to −40° C. and 5–6M t-butylhydroperoxide in decane (2 mmol) is added and left at room temperature. After overnight stirring, the reaction is concentrated and the crude mixture is chromatographed.

Example 4

Preparation of (1-Aryl)Propane-1,3-Diols from Aryl Aldehydes

To a solution of 1-arylaldehyde (30 mmol) in THF (60 mL) is added 1M vinyl magnesium bromide in THF (34 mL) at 0° C. After stirring for an hour, a solution of 1M BH3.THF complex in THF (40 mL) is added to the reaction mixture dropwise. The reaction is quenched with 3N NaOH (20 mL) and 30% hydrogen peroxide (10 mL) at 0° C. The organic fraction is separated and concentrated. The crude product is chromatographed to give 1-arylpropane-1,3-diol.

Example 5

Preparation of 1(4-Pyridyl)-1,3-Propanediol

Step A (J. Org. Chem., 1957, 22, 589)

To a solution of 3-(4-pyridine)propanol (10 g, 73 mmol) in acetic acid (75 mL) was added 30% hydrogen peroxide (10 mL) slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of reaction. Chromatography of the mixture by eluting with methanol-methylene chloride (1:9) resulted in pure diacetate (10.5 g, 60%).

Step B

To a solution of diacetate (5 g, 21.1 mmol) in methanol-water (3:1, 40 mL) was added potassium carbonate (14.6 g, 105 mmol). After stirring for 3 h at room temperature, the reaction mixture was concentrated. The residue was chromatographed on a silicagel column by eluting with methanol-methylene chloride (2:8) to obtain pure diol (2.2 g, 68%).

Example 6

Preparation of (1-Aryl)Propane-1,3-Diols from Propane-1,3-Diol

Step A (J. Org. Chem., 1988, 53, 911)

To a solution of oxalyl chloride (100 mmol) in dichloromethane (200 mL) at −78° C. is added dimethyl sulfoxide (130 mmol). The reaction mixture is stirred at −78° C. for 20 min before addition of 3-(benzyloxy)propan-1-ol (65 mmol) in dichloromethane (25 mL). After an hour at −78° C., reaction is quenched with triethylamine (260 mmol) and warmed to room temperature. Work-up and column chromatography by elution with dichloromethane results in 3-(benzyloxy)propan-1-al.

Step B

To a solution of 3-(benzyloxy)propan-1-al (6 mmol) in THF at 0° C. is added a 1M solution of arylmagnesium bromide in THF (6.7 mmol). The reaction is warmed to room temperature and stirred for 1 h. Work-up and column chromatography by elution with dichloromethane results in 1(aryl)-3-benzyloxy propanol.

Step C

To a solution of benzyl ether (500 mg) in ethyl acetate (10 mL) is added 10%Pd(OH)$_2$—C (100 mg). The reaction is stirred under hydrogen gas for 16 h. The reaction mixture is filtered through celite and concentrated. Chromatography of the residue by elution on a silicagel column results in product.

Example 7

Preparation of 1-Aryl Substituted-1,3-Propane Diols by Aldol Condensation

Step A (J. Org. Chem., 1990, 55, 4744)

To a solution of diisopropylamine (30 mmol) in ether (40 mL) at −78° C. is added 2.5M n-butyl lithium (30 mmol). The reaction is stirred for 15 min before adding t-butyl acetate (30 mmol) in ether (10 mL). After 20 min, aryl aldehyde (14 mmol) in ether (10 mL) is added and warmed to room temperature where it is stirred for 16 h. Work-up and column chromatography results in addition product.

Step B

To a solution of t-butyl ester (4.5 mmol) in THF (20 mL) is added 1M lithium aluminum hydride (7 mL) at 0° C. The reaction mixture is warmed to room temperature and stirred for 2 h. The reaction is quenched with ethyl acetate and saturated aq.sodium sulfate is added to precipitate the salts. Filtration, concentration of solvent and column chromatography results in pure diol.

Example 8

Preparation of 2-Substituted -1,3-Propanediols

Monoacetylation of 2-(Hydroxymethyl)-1,3-Propanediol

To a solution of 2-(hydroxymethyl)-1,3-propanediol (10 mmol) in pyridine (7.5 mL) at 0° C. is added acetic anhydride (10 mmol) slowly. The resulting solution is warmed to room temperature and stirred for 16 h. The reaction is concentrated under reduced pressure and chromatographed to obtain corresponding pure acetate.

Carbonate Formation of 2-(Hydroxymethyl)-1,3-Propanediol

To a solution of 2-(hydroxymethyl)-1,3-propanediol (10 mmol) in dichloromethane (20 mL) and pyridine (7.5 mL) at 0° C. is added methyl chloroformate (10 mmol) slowly. The resulting solution is warmed to room temperature and stirred for 16 h. The reaction is concentrated under reduced pressure and chromatographed to obtain pure carbonate.

Example 9

General Procedure for Preparation of 3-Aryl-3-Aminopropanols from Aryl Aldehydes (Shih, et al., *Heterocycles*, 1978, 9,1277)

Step A

A mixture of an appropriate aryl aldehyde (10 mmol), malonic acid (10 mmol), ammonium acetate (10 mmol) and 50 mL of 95% ethanol is heated in a water bath at 80° C. Carbon dioxide begins to evolve at 55° and the reaction is complete in 5–7 h. The white solid is collected by suction and recrystallized from aqueous ethanol to obtain the 3-aryl-3-aminopropionic acid.

Step B

To a suspension of lithium aluminum hydride (50 mmol) in anhydrous tetrahydrofuran (40 mL) is added a 3-aryl-3-aminopropionic acid (20 mmol) with cooling and stirring. The mixture is refluxed for 3 hours, allowed to stand overnight, and treated with moist ether and then with water to decompose the excess of lithium aluminum hyride. The organic layer is decanted, and the material left in the flask is extracted with hot ethylacetate. The organic solutions are combined and rotary evaporated. The residue is vacuum distilled or recrystallized to obtain 3-aryl-3-aminopropanol.

Example 10

General Procedure for Preparation of Chiral 1-Aryl Propane-1,3-Diols and 3-Aryl-3-Hydroxypropylamines from Epoxy Cinnamyl Alcohols (Gao, et al., *J. Org. Chem.*, 1988, 53, 4084)

Step A

To a solution of commercial (−)-(2S,3S)-2,3-epoxycinnamyl alcohol (10.0 mmol) in dimethoxyethane (50 mL) is added a 3.4 M solution of sodium bis(2-methoxyethoxy)aluminum hydride (Red-Al) in toluene (10.5 mmol) dropwise under nitrogen at 0° C. After stirring at room temperature for 3 h, the solution is diluted with ether and quenched with 5% HCl solution. After further stirring at room temperature for 30 min, the white precipitate formed is removed by filtration and boiled with ethyl acetate and filtered again. The combined organic extracts are dried and concentrated to give (R)-1-phenyl-1,3-dihydroxypropane.

Step B

To a solution of (R)-3-phenyl-1,3-dihydroxypropane (17.8 mmol) and triethylamine (25.6 mmol) in ether (90 mL) is added dropwise MsCl (18.7 mmol) under nitrogen at −10° C. After stirring at −10 to 0° C. for 3 h, the mixture is poured into ice water (30 mL), washed with 20% $H_2SO_4$, saturated aqueous $NaHCO_3$, and brine, and dried over magnesium sulfate. The crude product is purified by chromatography on silica gel column.

Step C

A solution of (R)-3-phenyl-3-(hydroxy)-propyl methanesulfonate (3 mmol) and methylamine (10 mL, 40% in water) in THF (10 mL) is heated at 65° C. for 3 h. After cooling, the solution is diluted with ether, washed with saturated aqueous sodium bicarbonate and brine, and dried with anhydrous potassium carbonate. Concentration results in (R)-3-phenyl-3-(hydroxy)-propyl amine.

Example 11

General Procedure for Preparation of 1-Aryl-Propylene-1,3-diamines from Cinnamyl Aldehydes (Weinhardt, et al., *J. Med. Chem.*, 1985, 28, 694)

Step A

To a solution of cinnamaldehyde (10 mmol) in 100 mL of EtOH is added substituted hydrazine (10 mmol). The reaction is stirred at room temperature for 45 min. Solvents are removed on a rotatory evaporator and saturated $NaHCO_3$ is added to the residue. The crude product is extracted into ether and the ether is removed under vacuum. Crude product following chromatography resulted in pure pyrazoline adduct.

Step B

A solution of 3-phenylpyrazoline (10 mmol) in 50 mL of AcOH and 10 mL of 10% HCl is hydrogenated at atmospheric pressure over 500 mg of 5% Pt/C. The reaction is stirred under hydrogen for 6 h. The catalyst is removed by filtration and the filtrate is concentrated. The crude product is purified by column to give pure 1-Aryl-propylene-1,3-diamines derivative.

Example 12

General Procedure for Formation of Cyclic Prodrugs from Phosphoramidite Intermediates Step A Synthesis of 1,3-diols, 1,3-aminoalcohols and 1,3-diamines is attained as described in Examples 4–11.

Step B

Preparation of Cyclic Phosphoramidite from Substituted Diols (*Tet.*, 1993, 49, 6123)

To a commercially available diisopropyl phosphoramidousdichloride (1 mmol) in THF (5 mL) is added substituted-1,3-diol (1 mmol) and triethylamine (4 mmol) in THF (5 mL) at −78° C. over 30 min. The reaction is slowly warmed to room temperature and allowed to stir overnight. The reaction mixture is filtered to remove salts and the filtrate is concentrated to give crude amidite. Chromatography on a silica column provides with pure cyclic diisopropyl phosphoramidite of 1,3-diol.

Step C

Addition of Cyclic Phosphoramidite and Oxidation (*J. Org. Chem.*, 1996, 61, 7996)

To a solution of drug containing alcohol or amine (1 mmol) and cyclic phosphoramidite (1 mmol) in DMF (10 mL) is added benzimidazolium triflate (1 mmol). The reaction is stirred for 30 min at room temperature. The mixture is cooled to −40° C. before addition of t-butylhydroperoxide (2 mmol) and left at room temperature overnight. Concentration and chromatography gives pure prodrug.

Example 13

General Procedure for Formation of Cyclohexanol Prodrugs

Step A

To a solution of cis, cis-1,3,5-cyclohexane triol (1 mmol) in methylene chloride (10 mL) is added phosphorusoxychloride (1.2 mmol) in 10 mL of methylene chloride dropwise at reflux temperature. The reaction mixture is stirred at reflux overnight and poured onto a mixture of ice and sodium bicarbonate. Extraction with additional methylene chloride, washing and evaporation gave crude chlorophosphate.

Step B

To a solution of crude chlorophosphate of cyclohexanetriol (1 mmol) in pyridine (10 mL) is added an alcohol or amine containing drug (1 mmol). The reaction is warmed to 60° C. and stirred overnight. After the completion of reaction, the mixture is concentrated and chromatographed to give pure cyclohexanol prodrug.

Examples of use of the method of the invention includes the following. It will be understood that these examples are exemplary and that the method of the invention is not limited solely to these examples.

For the purposes of clarity and brevity, chemical compounds are referred to as synthetic example numbers in the biological examples below.

BIOLOGICAL EXAMPLES

Example A

Activation of Compound 1.1 to Etoposide in Rat Hepatocytes

Compound 1.1, a prodrug of Etoposide, was tested for activation to etoposide phosphate and free etoposide in rat hepatocytes.

Methods:

Hepatocytes were prepared from fed Sprague-Dawley rats (250–300 g) according to the procedure of Berry and Friend (Berry, M. N., Friend, D. S. J. Cell Biol. 43, 506–520 (1969)) as modified by Groen (Groen, A. K. et al. Eur J. Biochem 122, 87–93 (1982)). Hepatocytes (75 mg wet weight/ml) were incubated in 1 ml Krebs-bicarbonate buffer containing 10 mM glucose, and 1 mg/ml BSA. Incubations were carried out in a 95% oxygen, 5% carbon dioxide atmosphere in closed, 50-ml Falcon tubes submerged in a rapidly shaking water bath (37° C.). A 10 mM stock solution of Compound 1.1 was prepared in methanol, and then diluted into the cell suspension or Krebs-bicarbonate buffer to yield a final concentration of 100 $\mu$M. At appropriate time points over the course of one hour, aliquots of the cell suspension were removed and spun through a silicon/mineral oil layer into 10% perchloric acid. The cell extracts in the acid layers were neutralized, and the intracellular prodrug metabolite content analyzed by reverse phase HPLC with use of a Beckman Ultrasphere ODS column (4.6×150 mm). The column was equilibrated with 20 mM potassium phosphate buffer, pH 6.3, and eluted with a gradient to 100% methanol. Detection was at 284 nm. Peaks on the chromatograms were identified by comparison to the retention times and spectra of standards of prodrug and parent compound.

Results:

Both Etoposide phosphate and free Etoposide were generated in rat hepatocytes. At the 2-hour time point, intracellular levels of Etoposide of approximately 40 nmoles/gram of cells were achieved. Additional Etoposide metabolites were also observed. Etoposide metabolites are associated with oncolytic activity. Compound 1.1 was stable in cell-free incubations, consistent with an enzyme-catalyzed mechanism of activation.

These studies demonstrate Compound 1.1 is activated to Etoposide in rat hepatocytes.

Example B

Activation of Compound 1.1 in vitro by Recombinant CYP3A4

Activation of Compound 1.1 was evaluated in reactions containing microsomes from baculovirus-infected insect cells co-expressing recombinant human P450-isozyme, CYP3A4, and cytochrome P450 reductase (Panvera Corp., Madison, Wis.).

Methods:

Reaction mixtures (0.5 ml @ 37° C.) consisted of 1 mg/ml Baculosomes, 100 $\mu$M Compound 1.1, 2mM NADPH and 100 mM $KH_2PO_4$ buffer. Reactions were incubated for 30 minutes in an Eppendorf Thermomixer 5436 at 37° C., and reciprocal shaking speed setting 6. 100 $\mu$l aliquots were collected at 0, 10, 20 and 30 minutes and quenched with 1.5 volumes of methanol. These extracts were spun for 10 minutes at 14,000 rpm in an Eppendorf microfuge and the supernatants were lyophilized to remove the methanol. The dried supernatant pellets were resuspended in 100 $\mu$l 20 mM potassium phosphate buffer, pH 6.3, clarified by centrifugation, and analyzed by HPLC as described in Example A.

Results:

CYP3A4 catalyzed the activation of Compound 1.1 to Etoposide phosphate. The rate of Etoposide phosphate formation observed was 386 nmoles Etoposide phosphate/nmole CYP3A4/h. The identity of Etoposide phosphate was confirmed by addition of alkaline phosphatase to the reaction mixtures. As expected, a new peak with the same retention time as Etoposide was formed.

The results indicate that Compound 1.1 is metabolized by CYP3A to generate Etoposide phosphate. The data also suggest that the conversion of Compound 1.1 to Etoposide described in Example A takes place via a two-step reaction: cytochrome P450-catalyzed cleavage to Etoposide phosphate followed by dephosphorylation to Etoposide potentially by means of an alkaline phosphatase-catalyzed reaction.

Example C

Compound 1.1Activity in Lymphoblastoid cells (+/−CYP3A4)

The degree of oncolytic activity of Compound 1.1 relative to free Etoposide is determined in a human leukemic cell line (AHH-1 TK +/−, Gentest) engineered to express human recombinant CYP3A4, and a parent cell line which does not express this activity.

Methods:

Compound 1.1 and etoposide are incubated with cells for 24 hours at doses ranging from 1 nm to 100 $\mu$M. Following drug exposure, cells are diluted to 10 cells/ml and cultured for 14 days to determine colony forming ability.

Results:

Compound 1.1 is shown to be cytotoxic in lymphoblastoid cells which express CYP3A4, as evidenced by its inhibition of cell colony formation. In the non-CYP3A4 expressing cells lines, a substantial reduction cytotoxic activity is found for Compound 1.1 Results of this nature suggest that Compound 1.1 is relatively safe in cells/organs which do not express CYP3A4 activity, but that its cytotoxic activity is unmasked in cells or organs such as the liver which express CYP3A4 activity. Etoposide exhibited cytotoxicity independent of CYP3A4 expression. Compound 1.1 is thus expected to exhibit an improved therapeutic index relative to etoposide in vivo.

Example D

Tissue Homogenate Activity

Compound 1.1 is tested for activation in homogenates from various tissues to assess the specificity of liver activation.

Methods:

Rats are anesthetized under halothane and tissues including liver, kidney, brain, heart, stomach, spleen, muscle, lung, and testis are excised and frozen in liquid nitrogen. Tissues are then homogenized in 1 to 3 volumes of 50 mM Tris-HCl, 154 mM KCL, 1 mM EGTA, pH 7.4. The homogenates are centrifuged at 10,000 rpm and 4° C. for 30 minutes and the supernatant recovered. Liver cytosol is prepared by centrifuging the crude liver extract for 1 hour at 40,000 rpm and 48° C. Reaction mixtures consist of 50 mM $KH_2PO_4$ pH 7.4, 13 mM glucose-6-phosphate, 2 mM NADP+, 10 units of glucose-6-phosphate dehydrogenase, 100 $\mu$M Compound 1.1 and tissue homogenate or liver cytosol at a protein concentration of 8.5 mg/ml. Reactions are incubated at 37° C. Aliquots are taken after 0 and 1 hour of incubation, and extracted with 60% methanol. The methanolic extracts are centrifuged at 14,000 rpm, and filtered prior to analysis by HPLC. The activation of Compound 1.1 to Etoposide phosphate and Etoposide is quantified as described in Example A.

Results:

Activation of Compound 1.1 is expected in crude rat liver homogenate resulting in the depletion of the prodrug and formation of parent compound, Etoposide. Incubation of Compound 1.1 with liver cytosol, which does not contain microsomal P450 enzymes, does not result in activation. Incubation with all of the other tissue homogenates fails to result in appreciable activation. Results of this nature indicate liver specific action of Compound 1.1 and suggest that liver will have the highest levels of etoposide since activation of Compound 1.1 occurs almost exclusively in the liver.

Example E

Enhanced Liver Delivery of Etoposide Following Administration of Compound 1.1 to Rat The temporal profiles of Etoposide in liver following administration of Compound 1.1 and free Etoposide to rat are compared.

Method:

Compound 1.1 and Etoposide are administered to normal, fasted rats orally by gavage (e.g. in PEG 4000) or intravenously (e.g. in saline) via tail vein catheters. At appropriate time points following drug administration, animals are lightly anesthetized with halothane. The peritoneal cavity is then opened and a blood sample is obtained from the abdominal vena cava and the liver freeze-clamped and excised.

The blood samples are heparinized and plasma is prepared. Plasma samples (100 $\mu$L) are mixed with perchloric acid or methanol, vortexed, and then clarified by centrifugation. The supernatants are analyzed for Etoposide by HPLC as described in Example A.

Livers are immediately homogenized in 3 volumes of 10% perchloric acid (w/w), and the extracts clarified by centrifugation at 2500×g (5 minutes). The resulting supernatants are removed and neutralized with 0.3 volumes of 3M KOH/3M KHCO$_3$. The neutralized liver extracts are then spun in an Eppendorf microfuge at 10,000 rpm (20 minutes, 4° C.). The supernatants are analyzed for Etoposide as described above.

Results:

The area under the curve of Etoposide in liver is expected to be higher following administration of Compound 1.1 compared to administration of free Etoposide. Reduced levels of Etoposide in plasma are found with Compound 1.1. Results of this nature suggest that administration of Compound 1.1 enhances the delivery of Etoposide to liver and reduces Etoposide exposure of peripheral tissues. Compound 1.1 is thus expected to have an enhanced therapeutic index relative to free Etoposide.

Example F

Identification of the P450 Isozyme Involved in the Activation

Prodrugs are evaluated for human microsome-catalyzed conversion to parent compound in the absence and presence of specific inhibitors of three major P450 isozymes: ketoconazole (CYP3A4), furafylline (CYP1A2), and sulfaphenazole (CYP2C9).

Methods:

Reactions (0.5 ml @ 37° C.) consist of 0.2 M KH$_2$PO$_4$, 13 mM glucose-6-phosphate, 2.2 mM NADP$^+$, 1 unit of glucose-6-phosphate dehydrogenase, 0–2.5 mg/ml human microsomal protein (In Vitro Technologies, Inc.), 250 $\mu$M prodrug, and 0–100 $\mu$M P450 isozyme inhibitor. Reactions are stopped by addition of methanol to a concentration of 60%, filtered (0.2 $\mu$M filter), and lyophilized. Samples are resuspended in HPLC buffer (10 mM phosphate pH 5.5, 2.5 mM octyl-triethyl-ammonium), loaded onto a YMC C8 HPLC column (250×4.6 mm), and eluted with a methanol gradient to 80%. Formation of parent drug is confirmed by co-elution with an authentic parent drug standard.

Results:

Prodrugs are converted readily to parent drug in human liver microsomes. Ketoconazole will inhibit the formation parent drug in a dose-dependent fashion. The other inhibitors, furafylline and sulfaphenazole, will show no significant inhibition. The results indicate that CYP3A4 is the primary P450 isoform responsible for activation of prodrugs in human liver.

Example G

Identification of Active Diastereomers

P450 enzyme-catalyzed oxidation of prodrug isomers are evaluated in reactions containing microsomes from baculovirus-infected insect cells co-expressing recombinant CYP3A4 and cytochrome P450 reductase (Panvera Corp., Madison, Wis.).

Methods:

Reaction mixtures are similar to those described in Example B. Prodrug stock solutions are prepared in methanol and added to the reaction mixture to a final concentration of 100 $\mu$M. Reactions are terminated by addition of methanol to 60% (v/v), evaporated, and redissolved in methanol. Prodrug isomers are separated and quantified by HPLC, for example with use of a YMC reverse phase C8 column (250×4.6 mm) equilibrated with mobile phase A (0.1% TFA) and eluted with a gradient to 80% mobile phase B (methanol) over 15 minutes.

Results:

Separation of the prodrug isomers by HPLC will allow determination of an oxidation rate for each individual isomer. Some or all of the isomers may be substrates for microsomal CYP3A4. A particular isomer may be oxidized to parent compound at a faster rate than another. Selection of single purified isomers aids optimization of pharmacokinetic and pharmacodynamic parameters.

Example H:

Identification of Prodrug Cleavage Products

Prodrugs are evaluated for microsome-catalyzed conversion to parent compound and phenol, an expected by-product of the reaction.

Methods:

Rat liver microsomes are purchased from Gentest, Inc. Reaction conditions, sample processing, and HPLC analysis are as described in Example D. Phenyl vinyl ketone or phenol, for example, can be identified by HPLC by its retention time and spectral characteristics relative to an authentic standard.

Results:

Parent compound and phenyl vinyl ketone or phenol are generated in an equimolar fashion in the reaction. This result supports an oxidative/β-elimination mechanism of prodrug activation.

Example I

Oral Bioavailability

The oral bioavailability (OBAV) of prodrugs is estimated by comparison of the area under the curve of parent drug generated in liver following oral administration to that generated following intravenous administration. The oral bioavailability of prodrugs where at least one Y' is —NR$^{15}$— is estimated by a urinary excretion method in rat.

Methods:

Fasted rats are dosed orally and intravenously with a prodrug. Liver samples are obtained, processed, and analyzed for parent drug content as described in Example D.

Prodrugs where at least one Y' is —NR$^6$— are administered by oral gavage to fasted, Sprague Dawley rats (220–240 g). The rats are subsequently placed in metabolic cages and urine is collected for 24 hours. The quantity of parent compound excreted into urine is determined by HPLC analysis. An ODS column eluted with a gradient from potassium phosphate buffer, pH 5.5 to acetonitrile may be employed for these measurements. The percentage oral bioavailability was estimated by comparison of the recovery in urine of the parent compound generated from the prodrug, to that recovered in urine 24 hours after intravenous administration of unsubstituted parent compound.

Results:

Oral bioavailability of the prodrugs is higher than that of their respective parent compound.

Example J

Evaluation of Prodrugs of Antifibrotic Agents in Rat Models of Liver Fibrosis

Agents are tested either in the carbon tetrachloride-induced or the bile duct ligation-induced model of liver fibrosis in the rat. Fibrosis is induced in male Sprague-Dawley rats (150–200 g) with carbon tetrachloride by twice- or three times-weekly subcutaneous injections of 0.1–0.2 ml/100 g body weight for 3 to 8 weeks as described (e.g. Hernandez-Munoz R, Diaz-Munoz M, Suarez J, Chagoya de Sanchez V, *Hepatology* 12: 242–248, 1990).

Bile duct ligations are performed in adult female Sprague-Dawley rats (225–250 g) according to the procedure described by Boigk et al. (Boigk G, Stroedter L, Herbst H, Aldschmidt J, Riecken E O, Schuppan D, *Hepatology* 26: 643–649, 1997). Antifibrotic agents are administered once or multiple times per day for 1 or more weeks by the subcutaneous, intraperitoneal, or oral route. In the carbon tetrachloride model, treatment may be initiated either concurrent with carbon tetrachloride treatment or following 1 or multiple weeks of carbon tetrachloride injection. In the bile duct ligation model, treatment is generally initiated 1 week post surgery but may also be initiated at later stages in the disease.

Efficacy in the fibrosis models is assessed by a variety of endpoints. Histological methods may, for example, be used to assess the degree of inflammation and necrosis in the liver (Knodell R G, Ishak K G, Black W C, Chen T S, Kaplowitz N, Kieman T W et al., *Hepatology* 1: 431–435, 1981). Collagen content may be determined by analysis of hepatic hydroxyproline content using a modification of the method of Jamall et al. (Gerling B, Becker M, Waldschmidt J, Schuppan D, *J. Hepatol.* 25: 79–84, 1996). Serum markers such as liver enzymes, bilirubin, creatinine, albumin and the aminoterminal propeptide of procollagen type III may also be quantified by the methods described for instance by Hernandez-Munoz et al., 1990 and Boigk et al., 1997. Liver adenylate content may also be measured as an indication of tissue viability by standard HPLC methods as described, for instance, by Erion et al. (Erion M D, Kasibhatla S R, Bookser B C, van Poelje P D, Reddy M R, Gruber H E, Appleman J R, *J. Am. Chem. Soc.*, 121, 308–319,1999). Reduced inflammation and necrosis, reduced collagen content, reduced elevation of serum markers, and increases in tissue adenylates are potential indications of antifibrotic activity in the animals models described.

Example K

Chemosensitization of Tumor Cells to Oncolytic Produgs by Transduction of a Prodrug-activating P450 Gene As certain tumor cells have reduced or no endogenous P450 activity (Wacher V J, Wu C-Y, Benet L Z, *Molecular Carcinogenesis* 13, 129–134, 1995 and references therein), the sensitivity of tumors to prodrugs of oncolytic agents may be increased by transducing the appropriate P450 gene into tumor cells. Gene transfer may be accomplished by means of Adenovirus, a vector capable of infecting a broad spectrum of dividing and nondividing cells. A recombinant, replication-defective Adenovirus is engineered carrying the appropriate P450 gene under control of a cytomegalovirus promoter as described, for example, by Chen et al. (Chen, L, Waxman D J, Chen D, Kufe D W, *Cancer Res.*, 56, 1331–1339, 1996). The modified vector is then used to transfer the gene to the tumor cells, where it is subsequently expressed. The expressed gene will activate the oncolytic prodrug and thus render the tumor sensitive to treatment. Other vectors including retroviruses, herpes simplex viruses and adeno-associated viruses may also be used, as well as non-viral vectors such as cationic liposomes and nonviral T7 autogene vectors (Waxman D J, Chen L, Hecht J E D, Jounaidi Y, *Drug Metabolism Reviews*, 31, 503–522, 1999 and references therein). In some instances it may be useful to co-transfer the P450 reductase gene, as the expressed protein may significantly increase the efficiency of P450-catalyzed prodrug activation (Chen L, Yu L, Waxman D J, *Cancer Res.*, 57, 4830, 1997). Specificity of the P450 gene-carrying vector for tumor cells may be accomplished through a variety of methods. For instance, tumor-specific DNA enhancer sequences may be incorporated into the vector that selectively activate expression of the gene exclusively within the tumor cell (Dachs G U, Dougherty G J, Stratford I J, Chaplin D J, *Oncol. Res.* 9, 313, 1997). Synthetic gene regulation systems may also be incorporated (Miller N, Whelan J, *Hum. Gene Ther.* 8:803, 1997).

Example L

Effect of Oncolytic Prodrug on Growth of Cyp3a4-Transfected Hepatoma Cells in Livers of Nude Mice The human hepatocellular carcinoma-derived cell line HepG2 (ATCC HB 8065) is well suited for xenografts in nude mice (Ain et al., *J. Surg. Res.* 57:366 (1994)). The CYP3A4 cytochrome P450 isoenzyme is expressed in HepG2 cells using a vaccinia virus system, as described in detail in Gonzalez et al., *Methods Enzymol.* 206:85 (1991). The resulting transfected line HepG2/CYP3A4 is maintained in cell culture. Male nude mice (Harlan Sprague Dawley, Indianapolis, Ind.) are used at the age of 6–8 weeks and anesthetized using halothane. A small incision is made in the left flank to explose the spleen. Using a 27 G needle, 0.05 ml of culture medium containing $5 \times 10^6$ HepG2/CYP3A4 cells are injected under the spleen capsule. A visible paling of the spleen and lack of bleeding are the criteria for a successful injection. The incision is closed with sutures (peritoneum) and wound clips (skin) and mice are allowed to recover from surgery. The intra-splenic injection results in a primary tumor in the spleen and metastases to the liver (Giavazzi et al., *Cancer Res.* 46:1928 (1986)). In some cases, the spleen is excised one minute following intra-splenic injection to allow flushing of the tumor cells into the splenic vein, thereby reducing the risk of rupture of the primary tumor before the liver metastases have developed (Adler et al., *Hepatology* 22:1482 (1995)).

The mice are treated with a prodrug of an oncolytic compound by intravenous injection twice weekly, using physiological saline or dimethylsulfoxide or polyethylene glycol-400 or some combination thereof as the vehicle. At various time intervals between 30 and 90 days after tumor cell injection, mice are weighed and sacrificed, and livers are excised and weighed. The liver/body weight ratio is used as a parameter for intrahepatic tumor growth. A statistically significant decrease in the liver/body weight ratio in livers from prodrug-treated animals, compared to vehicle-treated animals, is indicative of oncolytic activity.

Example M

Effect of Oncolytic Prodrug on Experimental Hepatocellular Carcinoma in the Rat

The Novikoff hepatoma is maintained as ascites in rats of type SA (Simonsen Laboratories, Gilroy, Calif.) according to Birns, *J. Natl. Cancer Inst.* 25:547 (1960). Male SA rats with body weights around 250 g are used for tumor cell implantation in the liver. On the day of the experiment, rats are anesthetized by an intraperitoneal injection of 23.3 mg ketamine, 1.6 mg xylazine, and 0.8 mg morphine in 0.3 ml physiological saline. When deep anesthesia has been obtained, a small laparotomy is performed, and $8.5 \times 10^6$ hepatoma cells in 0.1 ml physiological saline are injected under the capsule of the central liver lobe (Kurth et al., *J. Cancer Res. Clin. Oncol.* 122:421 (1996)). The incision is closed with sutures (peritoneum) and wound clips (skin) and rats are allowed to recover from surgery.

Rats are treated daily with a prodrug of an oncolytic compound administered either by intraperitoneal or intravenous injection, using physiological saline or dimethylsulfoxide or polyethylene glycol-400 or some combination thereof as the vehicle. Alternatively, rats are treated daily with a prodrug of an oncolytic compound administered by oral gavage, using polyethylene glycol-400 as the vehicle. On day 12 after tumor cell implantation, the rats are sacrificed by an overdose of anesthesia, and the tumor volume (V) is measured in situ with calipers by taking the largest (a) and the smallest (b) diameter and using the formula $V = a \times b^2/2$ (Carlsson et al., *J. Cancer Res. Clin. Oncol.* 105:20 (1983)). A statistically significant decrease in tumor volume in rats receiving oncolytic prodrugs, compared to vehicle-treated animals, is indicative of oncolytic activity.

Example N

Effect of Oncolytic Prodrug on Growth of Human Colorectal Tumor Cells Metastasized to the Liver of Nude Mice A human colorectal tumor line which preferentially invades the liver, such as the one described in Watson et al., *Eur. J. Cancer* 29A:1740 (1993) is maintained in cell culture. Male nude mice of 6–8 weeks of age (Harlan Sprague Dawley, Indianapolis, Ind.) receive an intraperitoneal injection of $10^6$ tumor cells in 1 ml physiological saline.

Ten days following inoculation, treatment with a prodrug of an oncolytic compound is commenced. Mice are treated daily with a prodrug of an oncolytic compound administered either by intraperitoneal or intravenous injection, using physiological saline or dimethylsulfoxide or polyethylene glycol-400 or some combination thereof as the vehicle. Alternatively, mice are treated daily with a prodrug of an oncolytic compound administered by oral gavage, using polyethylene glycol-400 as the vehicle. On day 40 after the tumor cell injection, mice are sacrificed and their livers excised. Visible liver metastases are counted, and the cross-sectional area of each metastatic lesion is determined using a dissection microscope fitted with a reticule in one of the oculars (Rohlff et al., *Cancer Res.* 59:1268, 1999). Alternatively, the liver/body weight ratio is used as an index of tumor burden according to the procedure described under Example H. Significant decreases in the number of metastases, the cross-sectional area and/or the liver/body weight ratio are indicative of oncolytic activity.

Example O

Chemical Stability

The stability of prodrugs of oncolytics is assessed in isotonic saline and in phosphate buffer (pH 3, 7, and 9).

Methods:

Aliquots of a 10 $\mu$g/mL prodrug solution in isotonic saline and in 100 mM potassium phosphate buffers at pH 3, 7, and 9 are sampled after 1, 2, 5, and 7 days of incubation at room temperature and analyzed by HPLC. A Beckman Ultrasphere C8 column (4.6×150 mm) is employed for example, and eluted with a gradient from 0.1% v/v trifluoroacetic acid to 80% methanol at a flow rate of 1.0 mL/min. Detection is by uv absorption at wavelengths corresponding to the absorbance maxima of the parent oncolytic and prodrug. Quantitation is performed relative to authentic prodrug and parent oncolytic standards.

Results:

No decomposition of the prodrugs to parent compound or other products is observed either in saline or buffer throughout the 7-day evaluation period. The results demonstrate that the prodrugs are stable for a minimum of seven days.

Example P

Stability to Esterases, Phosphatases, and Plasma

The stability of prodrugs of oncolytics to cleavage by purified esterase and phosphatase as well as plasma preparations is assessed.

Methods:

Carboxylesterase (porcine liver) and alkaline phosphatase (calf intestinal mucose) preparations are purchased from Sigma Chemical Co. (St. Louis, Mo.). Carboxyl esterase activity is measured in 0.1 M Tris-HCl buffer at pH 8.0. Activity towards p-nitrophenyl acetate, a known substrate and positive control in the reactions is measured as described for example by Matsushima M., et al. [*FEBS Lett.* (1991) 293(1–2): 37–41]. Alkaline phosphatase activity is measured in a 0.1 M diethanolamine buffer, pH 9.8, containing 0.5 mM MgCl2. Activity towards p-nitrophenyl phosphate, a known substrate and positive control in the reactions, is measured as described [e.g. Brenna O., et al., *Biochem J.* (1975) 151(2): 291–6]. Plasma is prepared by centrifugation of fresh, heparinized rat or human blood. Prodrugs of oncolytics are incubated at a concentration of, for example, 25 $\mu$M in appropriate reaction mixtures containing carboxylesterase, alkaline phosphatase, or rat or human plasma. In the case of the esterase and phosphatase assays, parallel reactions are run with known substrates of the enzymes as described above. Aliquots are removed from the reaction mixture at various time points and the reaction stopped by addition of methanol to 60%. Following centrifugation and filtration, the methanolic aliquots are analyzed for generation of parent compound by HPLC as described in Example O.

Results:

Parent compound is not detected following exposure of the prodrugs to carboxylesterase, alkaline phosphatase or plasma. The prodrugs are thus resistant to cleavage by the enzyme preparations.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound of formula I:

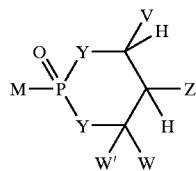

I wherein:
V, W, and W' are independently selected from the group of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group of hydroxy, acyloxy, alkoxycarbonyloxy, alkylthiocarbonyloxy, and aryloxycarbonyloxy, attached to one of said additional carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group of —CHR$^2$OH , —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡R$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{12}$, and —(CH$_2$)$_p$—SR$^{12}$;

p is an integer 2 or 3;

with the provisos that:
a) V, Z, W, W' are not all —H;
b) when Z is —R$^2$ or —OR$^2$, then V is not —H, alkyl, aralkyl, or alicyclic;
c) when Z is CHR$^2$OH, then M is not —NH(lower alkyl), —N(lower alkyl)$_2$, —NH(lower alkylhalide), —N(lower alkylhalide)$_2$ or —N(lower alkyl)(lower alkylhalide); and
d) when V is aryl or substituted aryl, then M is not —O(D) where D is hydrogen, a metal ion or an ammonium ion;

R$^2$ is selected from the group of R$^3$ and —H;
R$^3$ is selected from the group of alkyl, aryl, alicyclic, and aralkyl;
R$^6$ is selected from the group of —H, lower alkyl, acyloxyalkyl, alkoxycarbonyloxyalkyl, and lower acyl;
R$^{12}$ is selected from the group of —H, and lower acyl;
each Y is independently selected from the group of —O—, and —NR$^6$—;
M is selected from the group of drugs MH containing an —OH, —NHR$^2$, or —SH group, and that is attached to the phosphorus in formula I via O, N, or S of said OH, —NHR$^2$, or SH group;

and pharmaceutically acceptable prodrugs and salts thereof.

2. A compound according to claim 1, with the further proviso that when Z is CHR$^2$OH and V, W, and W' are H, then M does not include within its structure adenine, cytosine, guanine, thymine, uracil, 2,6-diamino purine, hypoxanthine, or a compound of the formula:

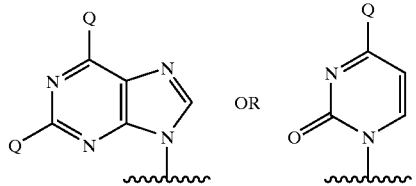

wherein Q is independently H, Cl, NHR$^Q$, NR$^Q$$_2$, NHC(O)R$^Q$, N(C(O)R$^Q$)$_2$, OH or NCHN(R$^Q$)$_2$; and
R$^Q$ is C$_1$–C$_{20}$ alkyl, aryl or aralkyl all optionally substituted with hydroxy or halogen.

3. A compound according claim 1, with the further proviso that when Z, W, and W' are H and V is aryl, substituted aryl, heteroaryl or substituted heteroaryl, then M does not include within its structure a group of the following formula:

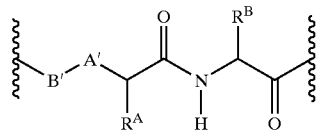

wherein:
R$^A$ and R$^B$ are independently hydrogen, optionally substituted alkyl having from 1 to about 14 carbons, or

87 optionally substituted cycloalkyl having from 3 to about 10 carbons;

A' is NH or $(CH_2)_k$ where k is an integer from 0 to 3; and B' is carbonyl or $SO_2$.

4. A compound according to claim 1 wherein MH is selected from the group of antiviral, anticancer, antihyperlipidemic, anti-inflammatory, antifibrotic, anti-diabetic and antiparasitic agents, with the proviso that said anti-diabetic agent is not an FBPase ihnibitor.

5. A compound according to claim 4 wherein MH is selected from the group of etoposide, teniposide, NK-611, GL-331, camptothecin, irinotecan, 9-aminocamptothecin, GG-211, topotecan, lurtotecan, DX-8951F, SKF 107874, SKF 108025, docetaxel, FCE-28161, paclitaxel, mitoxantrone, combretastatin A-4, Azatoxin, mycophenolic acid, coformycin, deoxycoformycin, S,S-dioxolane Combretastatin A-4, doxorubicin, daunorubicin, idarubicin, epirubicin, pirarubicin, mitomycin, eflornithine, piroxantrone, mitoxantrone, neocarzinostatin, esperamicin, calicheamicin theta, and losoxantrone.

6. A compound according to claim 5 wherein MH is selected from the group of etoposide, teniposide, doxorubicin, pirarubicin, mitoxantrone, topotecan, irinotecan, combretastatin A-4, S,S-dioxolane combretastatin, neocarzinostatin, and calicheamicin.

7. A compound according to claim 1 wherein at least one Y group is —O—.

8. A compound according to claim 7 wherein both Y groups are —O—, or when one Y group is —O—, then it is located closest to the W' and W groups.

9. A compound according to claim 8 wherein both Y groups are —O—.

10. A compound according to claim 1 wherein

V is selected from the group of aryl, substituted aryl, heteroaryl, and substituted heteroaryl;

W, and W' are independently selected from the group of —H, alkyl, aralkyl, alicyclic, aryl, substituted aryl, heteroaryl, substituted heteroaryl, 1-alkenyl, and 1-alkynyl; or together V and W are connected via an additional 3 carbon atoms to form an optionally substituted cyclic group containing 6 carbon atoms and substituted with one substituent selected from the group of hydroxy, acyloxy, alkoxycarbonyloxy, alkylthiocarbonyloxy, and aryloxycarbonyloxy, attached to one of said carbon atoms that is three atoms from a Y attached to the phosphorus; or together Z and W are connected via an additional 3–5 atoms to form a cyclic group, optionally containing one heteroatom; or together W and W' are connected via an additional 2–5 atoms to form a cyclic group, optionally containing 0–2 heteroatoms.

11. A compound according to claim 1, wherein

V, W and W' are independently selected from the group of aryl, substituted aryl, heteroaryl, substituted heteroaryl, 1-alkenyl and 1-alkynyl, and Z is selected from the group of —$OR^2$, —$SR^2$, —$R^2$, —$NR^2_2$, —$OCOR^3$, —$OCO_2R^3$, —$SCOR^3$, —$SCO_2R^3$, —$NHCOR^2$, —$NHCO_2R^3$, —$(CH_2)_p$—$OR^{12}$, and —$(CH_2)_p$—$SR^{12}$; or V, W, and W' are independently selected from the group of H, alkyl, aralkyl and alicyclic, and Z is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —$SR^2$, —$CH_2aryl$, —CH

88

(aryl)OH, —$CH(CH=CR^2_2)OH$, —$CH(C\equiv CR^2)OH$; and —$CH_2NHaryl$; or together V and W are connected via an additional 3 carbon atoms to form a cyclic substituted group containing 6 carbon atoms and mono-substituted with a substituent selected from the group of hydroxyl, acyloxy, alkoxycarbonyloxy, alkylthiocarbonyloxy, and aryloxycarbonyloxy attached to one of said additional carbon atoms that is three atoms from an Y attached to the phosphorus.

12. A compound according to claim 11, wherein V is selected from the group of aryl, substituted aryl, heteroaryl, substituted heteroaryl, 1-alkenyl and 1-alkynyl, and Z is selected from the group of —$OR^2$, —$SR^2$, —$R^2$, —$NR^2_2$, —$OCOR^3$, —$OCO_2R^3$, —$SCOR^3$, —$SCO_2R^3$, —$NHCOR^2$, —$NHCO_2R^3$, —$(CH_2)_p$—$OR^{12}$, and —$(CH_2)_p$—$SR^{12}$.

13. A compound according to claim 11, wherein V, W and W' are independently selected from the group of H, alkyl, aralkyl and alicyclic, and Z is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —$SR^2$, —$CH_2aryl$, —$CH(aryl)OH$, —$CH(CH=CR^2_2)OH$, —$CH(C\equiv CR^2)OH$; and —$CH_2NHaryl$.

14. A compound according to claim 11, wherein together V and W are connected via an additional 3 carbon atoms to form a cyclic group containing 6 carbon atoms and mono-substituted with a substituent selected from the group of hydroxyl, acyloxy, alkoxycarbonyloxy, alkylthiocarbonyloxy, and aryloxycarbonyloxy attached to one of said additional carbon atoms that is three atoms from an Y attached to the phosphorus.

15. A compound according to claim 12 wherein Z, W, and W' are H; and $R^6$ is selected from the group of —H and lower alkyl.

16. A compound according to claim 15 wherein V is selected from the group of aryl and substituted aryl.

17. A compound according to claim 16 wherein V is selected from the group of phenyl and substituted phenyl.

18. A compound according to claim 17 wherein V is selected from the group of phenyl, 3,5-dichlorophenyl, 3-bromo-4-fluorophenyl, 3-chlorophenyl, 2-bromophenyl, and 3-bromophenyl.

19. A compound according to claim 15 wherein V is selected from the group of heteroaryl and substituted heteroaryl.

20. A compound according to claim 19 wherein V is 4-pyridyl.

21. A compound according to claim 1 wherein together V and Z are connected via an additional 3–5 atoms to form a cyclic group, optionally containing 1 heteroatom, that is fused to an aryl group at the beta and gamma positions to the Y attached to phosphorus.

22. A compound according to claim 21 wherein said aryl group is an optionally substituted monocyclic aryl group and the connection between Z and the aryl group is selected from the group of O, $CH_2$, $CH_2CH_2$, $OCH_2$ or $CH_2O$.

23. A compound according to claim 11 wherein together V and W are connected via an additional 3 carbon atoms to form an optionally substituted cyclic group containing 6 carbon atoms and mono-substituted with one substituent selected from the group of hydroxy, acyloxy, alkoxycarbonyloxy, alkylthiocarbonyloxy, and aryloxycarbonyloxy attached to one of said additional carbon atoms that is three atoms from an Y attached to the phosphorus.

24. A compound according to claim 23 wherein together V and W form a cyclic group selected from the group of —CH₂—CH(OH)—CH₂—, —CH₂CH(OCOR³)—CH₂—, and —CH₂CH(OCO₂R³)—CH₂—.

25. A compound according to claim 13 wherein W, W' and V are —H.

26. A compound according to claim 12 wherein Z is selected from the group of —OR², —R², —OCOR³, —OCO₂R³, —NHCOR², —(CH₂)$_p$—OR¹², and —(CH₂)$_p$—SR¹².

27. A compound according to claim 26 wherein Z is selected from the group of —OR², —R², —OCOR³, —OCO₂R³, and —NHCOR².

28. A compound according to claim 27 wherein Z is selected from the group of H and lower alkyl.

29. A compound according to claim 10 wherein W and W' are independently selected from the group of H, alkyl, aralkyl, alicyclic, aryl, substituted aryl, heteroaryl, substituted heteroaryl, 1-alkenyl and 1-alkynyl.

30. A compound according to claim 29 wherein W and W' are the same group.

31. A compound according to claim 30 wherein W and W' are H.

32. A compound according to claim 12 wherein M is attached to phosphorus via an oxygen or nitrogen atom.

33. A compound according to claim 32 wherein V is selected from the group of aryl and substituted aryl.

34. A compound according to claim 33 wherein V is selected from the group of phenyl, 3,5-dichlorophenyl, 3-bromo-4-fluorophenyl, 3-chlorophenyl, 2-bromophenyl, and 3-bromophenyl.

35. A compound according to claim 32 wherein V is selected from the group of heteroaryl and substituted heteroaryl.

36. A compound according to claim 35 wherein V is 4-pyridyl.

37. A compound according to claim 13 wherein M is attached to the phosphorus via a nitrogen or oxygen atom.

38. A compound according to claim 37 wherein Z is selected from the group of —CHR²OH, —CHR²OC(O)R³, and —CHR²OCO₂R³, and wherein R² is H or aryl.

39. A compound according to claim 38 wherein R² is —H.

40. A compound according to claim 12 wherein W' and Z are —H, W and V are both the same aryl, substituted aryl, heteroaryl, or substituted heteroaryl, and V and W are cis to each other.

41. A compound according to claim 12 wherein W and W' are H, V is selected from the group of aryl, substituted aryl, heteroaryl, substituted heteroaryl, and Z is selected from the group of —H, OR², and —NHCOR².

42. A compound according to claim 41 wherein Z is —H.

43. A compound according to claim 42 wherein V is selected from the group of phenyl and substituted phenyl.

44. A compound according to claim 42 wherein V is an optionally substituted monocyclic heteroaryl containing at least one nitrogen atom.

45. A compound according to claim 44 wherein V is 4-pyridyl.

46. A compound according to claim 41 wherein V is selected from the group of phenyl, phenyl substituted with 1–3 halogens, and 4-pyridyl and MH is selected from the group of etoposide, doxorubicin, and taxol.

47. A compound according to claim 42 wherein M is attached to the phosphorus via an oxygen atom.

48. A compound according to claim 1 wherein MH is from the class epipodophyllotoxins.

49. A compound according to claim 48 wherein MH is selected from the group of Etoposide, Teniposide, NK-611, GL-331, and Azatoxin.

50. A compound of formula I:

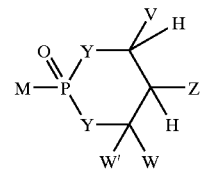

wherein

W and W' are independently selected from the group of —H, alkyl, aryl, substituted aryl, heteroaryl, and substituted heteroaryl;

V is selected from the group of aryl, substituted aryl, heteroaryl, substituted heteroaryl, 1-alkenyl and 1-alkynyl;

Z is selected from the group of —OR², —SR², —R², —NR²₂, —OCOR³, —OCO₂, R³, —SCOR³— SCO₂R³, —NHCOR², —NHCO₂R³, —(CH₂)$_p$— OR¹², and —(CH₂)$_p$—SR¹²;

p is an integer 2 or 3;

with the provisos that:
a) when V is aryl or substituted aryl, then M is not —O(D) where D is hydrogen, a metal ion or an ammonium ion; and
b) when Z is CHR²OH, then M is not —NH(lower alkyl), —N(lower alkyl)₂, —NH(lower alkylhalide), —N(lower alkylhalide)₂ or —N(lower alkyl)(lower alkylhalide);

R² is selected from the group of R³ and —H;

R³ is selected from the group of alkyl, aryl, alicyclic, and aralkyl;

R⁶ is selected from the group of —H, lower alkyl, acyloxyalkyl, alkoxycarbonyloxyalkyl, and lower acyl;

R¹² is selected from the group of —H, and lower acyl;

each Y is independently selected from the group of —O—, and —NR⁶—;

M is selected from the group of drugs MH having an —OH, —NHR², or —SH group, and that is attached to the phosphorus in formula I via O, N, or S of said OH, —NHR², or SH group;

and pharmaceutically acceptable prodrugs and salts thereof.

51. A compound according to claim 50 wherein MH is selected from the group of antiviral, anticancer, antihyperlipidemic, anti-inflammatory, antifibrotic, antidiabetic and antiparasitic agents, with the proviso that said anti-diabetic agent is not an FBPase ihnibitor.

52. A compound according to claim 51 wherein MH is selected from the group of etoposide, teniposide, NK-611, GL-331, camptothecin, irinotecan, 9-aminocamptothecin, GG-211, topotecan, lurtotecan, DX-8951F, SKF 107874, SKF 108025, docetaxel, FCE-28161, paclitaxel, mitoxantrone, combretastatin A-4, Azatoxin, mycophenolic acid, coformycin, deoxycoformycin, S,S-dioxolane Combretastatin A-4, doxorubicin, daunorubicin, idarubicin, epirubicin, pirarubicin, mitomycin, eflornithine, piroxantrone, mitoxantrone, neocarzinostatin, esperamicin, calicheamicin theta, and losoxantrone.

53. A compound according to claim 52 wherein MH is selected from the group of etoposide, teniposide, doxorubicin, pirarubicin, mitoxantrone, topotecan, irinotecan, combretastatin A-4, S,S-dioxolane combretastatin, neocarzinostatin, and calicheamicin.

54. A compound according to claim 54 wherein at least one Y group is —O—.

55. A compound according to claim 56 wherein both Y groups are —O—, or when one Y group is —O—, then it is located closest to the W' and W groups.

56. A compound according to claim 55 wherein both Y groups are —O—.

57. A compound according to claim 56 wherein Z, W, and W' are H; and V is selected from the group of aryl, substituted aryl, heteroaryl, and substituted heteroaryl.

58. A compound according to claim 50 wherein Z, W, and W' are H; and $R^6$ is selected from the group of —H and lower alkyl.

59. A compound according to claim 58 wherein V is selected from the group of aryl and substituted aryl.

60. A compound according to claim 59 wherein V is selected from the group of phenyl, 3,5-dichlorophenyl, 3-bromo-4-fluorophenyl, 3-chlorophenyl, 2-romophenyl, and 3-bromophenyl.

61. A compound according to claim 58 wherein V is selected from the group of heteroaryl and substituted heteroaryl.

62. A compound according to claim 61 wherein V is 4-pyridyl.

63. A compound according to claim 50 wherein Z is selected from the group of —$OR^2$, —$R^2$, —$OCOR^3$, —$OCO_2R^3$, —$NHCOR^2$, —$(CH_2)_p$—$OR^{12}$, and —$(CH_2)_p$—$SR^{12}$.

64. A compound according to claim 50 wherein W and W' are the same group.

65. A compound according to claim 64 wherein Z, W, and W' are H.

66. A compound according to claim 51 wherein M is attached to phosphorus via an oxygen or nitrogen atom.

67. A compound according to claim 66 wherein V is selected from the group of aryl and substituted aryl.

68. A compound according to claim 67 wherein V is selected from the group of phenyl, 3,5-dichlorophenyl, 3-bromo-4-fluorophenyl, 3-chlorophenyl, 2-bromophenyl, and 3-bromophenyl.

69. A compound according to claim 66 wherein V is selected from the group of heteroaryl and substituted heteroaryl.

70. A compound according to claim 69 wherein V is 4-pyridyl.

71. A compound according to claim 66 wherein V is selected from the group of phenyl, phenyl substituted with 1–2 halogens and 4-pyridyl and MH is selected from the group of etoposide, doxorubicin, and taxol.

72. A compound according to claim 50 wherein MH is from the class epipodophyllotoxins.

73. A compound according to claim 72 wherein MH is selected from the group of Etoposide, Teniposide, NK-611, GL-331, and Azatoxin.

74. A compound of formula I:

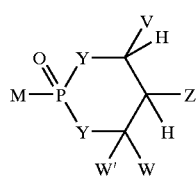

I wherein
Z is selected from the group of: —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —$SR^2$, —$CH_2aryl$, —$CH(aryl)OH$, —$CH(CH=CR^2{}_2)OH$, —$CH(C≡CR^2)OH$; and —$CH_2NHaryl$;

V, W and W' are independently selected from the group of —H, alkyl, aralkyl, and alicyclic;
with the provisos that:
a) when Z is $CHR^2OH$, then M is not —NH(lower alkyl), —N(lower alkyl)$_2$, —NH(lower alkylhalide), —N(lower alkylhalide)$_2$ or —N(lower alkyl)(lower alkylhalide);
b) when V is aryl or substituted aryl, then M is not —O(D) where D is hydrogen, a metal ion or an ammonium ion; and
$R^2$ is selected from the group of $R^3$ and —H;
$R^3$ is selected from the group of alkyl, aryl, alicyclic, and aralkyl;
$R^6$ is selected from the group of —H, lower alkyl, acyloxyalkyl, alkoxycarbonyloxyalkyl, and lower acyl;
each Y is independently selected from the group of —O—, and —$NR^6$—;
M is selected from the group of drugs MH containing an —OH, —$NHR^2$, or —SH group, and that is attached to the phosphorus in formula I via O, N, or S of said OH, —$NHR^2$, or SH group;
and pharmaceutically acceptable prodrugs and salts thereof.

75. A compound according to claim 74 wherein MH is selected from the group of antiviral, anticancer, antihyperlipidemic, anti-inflammatory, antifibrotic, anti-diabetic and antiparasitic agents, with the proviso that said anti-diabetic agent is not an FBPase ihnibitor.

76. A compound according to claim 75 wherein MH is selected from the group of etoposide, teniposide, NK-611, GL-331, camptothecin, irinotecan, 9-aminocamptothecin, GG-211, topotecan, lurtotecan, DX-8951F, SKF 107874, SKF 108025, docetaxel, FCE-28161, paclitaxel, mitoxantrone, combretastatin A-4, Azatoxin, mycophenolic acid, coformycin, deoxycoformycin, S,S-dioxolane Combretastatin A-4, doxorubicin, daunorubicin, idarubicin, epirubicin, pirarubicin, mitomycin, eflornithine, piroxantrone, mitoxantrone, neocarzinostatin, esperamicin, calicheamicin theta, and losoxantrone.

77. A compound according to claim 76 wherein MH is selected from the group of etoposide, teniposide, doxorubicin, pirarubicin, mitoxantrone, topotecan, irinotecan, combretastatin A-4, S,S-dioxolane combretastatin, neocarzinostatin, and calicheamicin.

78. A compound according to claim 74 wherein at least one Y group is —O—.

79. A compound according to claim 78 wherein both Y groups are —O—, or when one Y group is —O—, then it is located closest to the W' and W groups.

80. A compound according to claim 77 wherein both Y groups are —O—.

81. A compound according to claim 74 wherein V, W, and W' are —H.

82. A compound according to claim 74 wherein W and W' are the same group.

83. A compound according to claim 82 wherein V, W, and W' are H.

84. A compound according to claim 74 wherein M is attached to phosphorus via an oxygen or nitrogen atom.

85. A compound according to claim 81 wherein Z is selected from the group of —$CHR^2OH$, —$CHR^2OC(O)R^3$, and —$CHR^2OCO_2R^3$, and wherein $R^2$ is H or aryl.

86. A compound according to claim 85 wherein $R^2$ is —H, and Y is —O—.

87. A compound according to claim 74 wherein MH is from the class epipodophyllotoxins.

88. A compound according to claim 87 wherein MH is selected from the group of Etoposide, Teniposide, NK-611, GL-331, and Azatoxin.

89. A compound according to claim 12, wherein the hydrogen geminal to V and the oxygen attached to the phosphorus via a double bond are in a cis configuration with respect to each other.

90. A compound according to claim 50, wherein the hydrogen geminal to V and the oxygen attached to the phosphorus via a double bond are in a cis configuration with respect to each other.

91. A compound according to claim 12 wherein W' and Z are H; W and V are both the same aryl, substituted aryl, heteroaryl, or substituted heteroaryl, and V and W are trans to each other.

92. A method of treating diseases of the liver or metabolic diseases where the liver is responsible for the overproduction of a biochemical end product by administering to an animal a pharmaceutically effective amount of a compound of formula I:

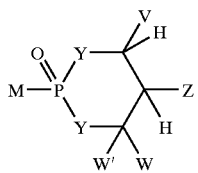

I wherein:
V, W, and W' are independently selected from the group of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group of hydroxy, acyloxy, alkoxycarbonyloxy, alkylthiocarbonyloxy, and aryloxycarbonyloxy, attached to one of said additional carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group of —$CHR^2OH$, —$CHR^2OC(O)R^3$, —$HR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2_2)OH$, —$CH(C\equiv CR^2)OH$, —$R^2$, —$NR^2_2$, —$OCOR^3$, —$OCO_2R^3$, —$SCOR^3$, $SCO_2R^3$, —$NHCOR^2$, —$NHCO_2R^3$, —$CH_2NHaryl$, —$(CH_2)_p$—$OR^{12}$, and —$(CH_2)_p$—$SR^{12}$;

p is an integer 2 or 3;

with the provisos that:
a) V, Z, W, W' are not all —H;
b) when Z is —$R^2$ or —$OR^2$, then V is not —H, alkyl, aralkyl, or alicyclic;
c) when Z is $CHR^2OH$, then M is not —NH(lower alkyl), —N(lower alkyl)$_2$, —NH(lower alkylhalide), —N(lower alkylhalide)$_2$ or —N(lower alkyl)(lower alkylhalide); and
d) when V is aryl or substituted aryl, then M is not —O(D) where D is hydrogen, a metal ion or an ammonium ion;

$R^2$ is selected from the group of $R^3$ and —H;
$R^3$ is selected from the group of alkyl, aryl, alicyclic, and aralkyl;
$R^6$ is selected from the group of —H, lower alkyl, acyloxyalkyl, alkoxycarbonyloxyalkyl, and lower acyl;
$R^{12}$ is selected from the group of —H, and lower acyl;
each Y is independently selected from the group of —O—, and —$NR^6$—;
M is selected from the group of drugs MH containing an —OH, —$NHR^2$, or —SH group, and that is attached to the phosphorus in formula I via O, N or S of said OH, —$NHR^2$, or —SH group;
and pharmaceutically acceptable prodrugs and salts thereof.

* * * * *